United States Patent
Benhida et al.

(10) Patent No.: US 11,440,906 B2
(45) Date of Patent: Sep. 13, 2022

(54) BIGUANIDE DERIVATIVES AND THEIR REARRANGEMENT PRODUCTS FOR USE IN THE TREATMENT OF CANCER

(71) Applicants: CENTRE NATIONAL DE LA RECHERCHE SCIENTIFIQUE, Paris (FR); INSTITUT NATIONAL DE LA SANTÉ ET DE LA RECHERCHE MÉDICALE, Paris (FR); UNIVERSITE COTE D'AZUR, Nice (FR)

(72) Inventors: Rachid Benhida, Nice (FR); Stephane Rocchi, Villefranche sur Mer (FR); Cyril Ronco, Nice (FR); Emile Jaune, Saint-Cannat (FR); Oleksandr Grytsai, Nice (FR); Nedra Tekaya, Nice (FR)

(73) Assignees: Centre National de la Recherche Scientifique, Paris (FR); INSERM (Institut National de la Santé et de la Recherche Médicale), Paris (FR); Université Côte d'Azur, Nice (FR)

( * ) Notice: Subject to any disclaimer, the term of this patent is extended or adjusted under 35 U.S.C. 154(b) by 0 days.

(21) Appl. No.: 16/956,003

(22) PCT Filed: Dec. 21, 2018

(86) PCT No.: PCT/EP2018/086772
§ 371 (c)(1),
(2) Date: Jun. 19, 2020

(87) PCT Pub. No.: WO2019/122418
PCT Pub. Date: Jun. 27, 2019

(65) Prior Publication Data
US 2020/0308156 A1 Oct. 1, 2020

(30) Foreign Application Priority Data
Dec. 22, 2017 (EP) .................................. 17306912

(51) Int. Cl.
| | |
|---|---|
| *C07D 251/48* | (2006.01) |
| *C07D 401/04* | (2006.01) |
| *C07D 403/04* | (2006.01) |
| *C07D 405/04* | (2006.01) |
| *C07D 409/04* | (2006.01) |
| *A61P 35/00* | (2006.01) |
| *C07D 409/14* | (2006.01) |
| *C07D 277/48* | (2006.01) |
| *C07D 277/82* | (2006.01) |
| *C07D 403/12* | (2006.01) |
| *C07D 403/14* | (2006.01) |
| *C07D 417/12* | (2006.01) |

(52) U.S. Cl.
CPC ............ *C07D 409/14* (2013.01); *A61P 35/00* (2018.01); *C07D 251/48* (2013.01); *C07D 277/48* (2013.01); *C07D 277/82* (2013.01); *C07D 401/04* (2013.01); *C07D 403/04* (2013.01); *C07D 403/12* (2013.01); *C07D 403/14* (2013.01); *C07D 405/04* (2013.01); *C07D 409/04* (2013.01); *C07D 417/12* (2013.01)

(58) Field of Classification Search
CPC .. C07D 251/48; C07D 401/04; C07D 403/04; C07D 405/04; C07D 409/04; A61P 35/00
See application file for complete search history.

(56) References Cited

FOREIGN PATENT DOCUMENTS

| | | |
|---|---|---|
| JP | 49 69688 A | 7/1974 |
| SU | 162 150 A1 | 4/1964 |
| WO | 2013/188452 A1 | 12/2013 |
| WO | 2015/155272 A1 | 10/2015 |

OTHER PUBLICATIONS

Chemical Abstracts Registry No. 53530-76-0, indexed in the Registry file on STIN CAS Online on Nov. 16, 1984. (Year: 1984).*
Rowe, Raymond C, Paul J. Sheskey, and Marian E Quinn. Handbook of Pharmaceutical Excipients. London: Pharmaceutical Press, 6th Edition, 2009, pp. 238, 239 and 766. (Year: 2009).*
El-Kerdawy et al., Zhonghua Yaoxue Zazhi (1991), 43(5), pp. 355-364. (Year: 1991).*
Cerezo et al: "Metformin Blocks Melanoma Invasion and Metastasis Development in AMPK/p53-Dependent Manner", Molecula Cancer Therapeutics, Jun. 5, 2013.
Tomic et al: "Metformin inhibits melanoma development through autophagy and apoptosis mechanisms", Cell Death and Disease, vol. 2, 2011.

* cited by examiner

*Primary Examiner* — Laura L Stockton
(74) *Attorney, Agent, or Firm* — WCF IP

(57) ABSTRACT

The present disclosure relates to biguanide derivatives of formula (I) and their rearrangement products. The present disclosure also relates to the use of these compounds in a method for treating cancer, in particular melanoma.

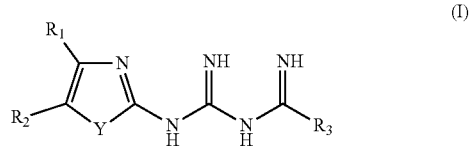

5 Claims, 8 Drawing Sheets

A.

B.

E.

A.

B.

A.

B.

BIGUANIDE DERIVATIVES AND THEIR REARRANGEMENT PRODUCTS FOR USE IN THE TREATMENT OF CANCER

TECHNICAL FIELD

The present disclosure relates to biguanide derivatives and their rearrangement products. The present disclosure also relates to the use of these compounds in a method for treating cancer, in particular melanoma.

BACKGROUND

Cancers represent one of the most important causes of death in France. Among cancers, melanoma is a skin cancer that is widespread in France, with about 8000 new cases diagnosed each year and more than 1000 deaths. This cancer is therefore a major public health problem. Melanoma is a malignant tumor developed from melanocytes that are responsible for the synthesis of melanin, which are photo-protective pigments. Melanoma is an extremely aggressive tumor with a high metastatic potential towards lymph nodes, liver, lungs, central nervous system and skin. As soon as metastases appear, the vital prognosis becomes unfavorable because of the poor efficiency of all current treatments.

Recently, encouraging results have been obtained with BRAF inhibitors (vemurafenib (PLX 4032) and dabrafenib), which target only B-Raf mutant melanomas (approximately 50% of the metastatic melanoma). Unfortunately, after a short period of remission, melanoma, in almost all cases, gains resistance against these drugs and metastases develop again, increasing the patient's life expectancy by about 2 months. Immunotherapies have also been developed recently. They are based on anti-CTLA4 and Anti-PD1 antibodies that reactivate the immune response. However, immunotherapies give an objective response in only 15 to 30% of patients.

It has also been reported that metformin, a drug normally used to treat diabetes, is able to inhibit the growth of melanoma cells (Tomic et al., Cell Death and Disease, 1; 2: e199, 2011) and the development of metastasis (Cerezo et al, Molecular Cancer Therapeutics, 12 (8): 1605-15, 2013). Nevertheless, a high dose of metformin is likely to be required to induce cell death (IC50=10 mM, ten millimolar).

Thus, there is a need for compounds and compositions with anti-proliferative properties, which could be used in particular to treat patients with melanoma and for example, patients with BRAF inhibitor-resistant melanoma.

SUMMARY

The inventors surprisingly found that biguanide derivatives comprising a heteroaryl moiety, and their rearrangement products, have a high biological activity towards cancer lines such melanoma cell lines, including melanoma cell lines resistant to BRAF inhibitors.

Consequently, in a first aspect, the disclosure relates to a compound of formula (I)

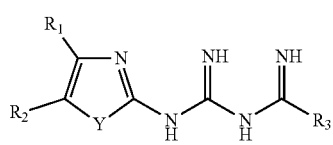

wherein
$R_1$ and $R_2$ are independently selected from H, halogen, $C_1$-$C_6$ alkyl, $C_3$-$C_6$ cycloalkyl, $C_1$-$C_6$ haloalkyl, $C_2$-$C_6$ alkenyl, $C_2$-$C_6$ alkynyl, heterocyclyl having 5 to 10 ring atoms, aryl having 6 to 10 ring atoms, heteroaryl having 5 to 10 ring atoms, and $C_7$-$C_{16}$ aralkyl, said alkyl, cycloalkyl, haloalkyl, alkenyl, alkynyl, heterocyclyl, aryl, heteroaryl and aralkyl being optionally substituted with one or more substituents independently selected from oxo, halogen, $C_1$-$C_6$ alkyl, $C_1$-$C_6$ alkoxy, $C_1$-$C_6$ haloalkyl, —OH, —NR"R'", —NO$_2$, —CN and —(CO)—R;

or $R_1$ and $R_2$, together with the carbon-carbon double bond between them, form a 6 to 10 membered aryl or heteroaryl ring, said aryl and heteroaryl being optionally substituted with one or more substituents independently selected from oxo, halogen, $C_1$-$C_6$ alkyl, $C_1$-$C_6$ alkoxy, $C_1$-$C_6$ haloalkyl, —OH, —NR"R'", —NO$_2$, —CN and —(CO)—R;

Y is —O— or —S—;

$R_3$ is selected from $C_1$-$C_6$ alkyl, $C_3$-$C_6$ cycloalkyl, $C_1$-$C_6$ haloalkyl, $C_2$-$C_6$ alkenyl, $C_2$-$C_6$ alkynyl, heterocyclyl having 5 to 10 ring atoms, aryl having 6 to 10 ring atoms, heteroaryl having 5 to 10 ring atoms and $C_7$-$C_{16}$ aralkyl, said alkyl, cycloalkyl, haloalkyl, alkenyl, alkynyl, heterocyclyl, aryl, heteroaryl and aralkyl being optionally substituted with one or more substituents independently selected from oxo, halogen, $C_1$-$C_6$ alkyl, $C_1$-$C_6$ alkoxy, $C_1$-$C_6$ haloalkyl, —OH, —NR"R'", —NO$_2$, —CN and —(CO)—R;

each R is independently selected from H, $C_1$-$C_6$ alkyl, $C_1$-$C_6$ alkoxy and —NR"R'";

each R" and R'" is independently selected from H and $C_1$-$C_6$ alkyl.

In a second aspect, the disclosure relates to a compound of formula (II) or (III)

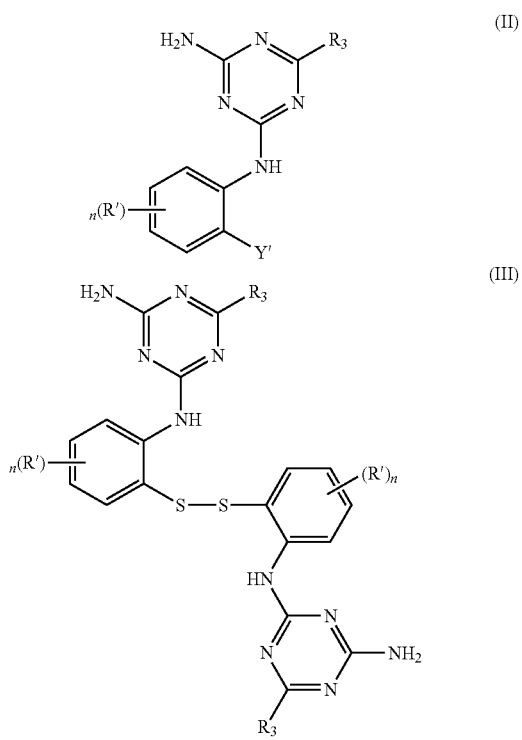

wherein

Y' is —SR$_4$ or —OR$_5$,

R$_4$ is selected from H, C$_1$-C$_6$ alkyl and protecting groups;

R$_5$ is selected from H and protecting groups;

each R' is independently selected from halogen, C$_1$-C$_6$ alkyl, C$_1$-C$_6$ alkoxy, C$_1$-C$_6$ haloalkyl, —OH, —NR"R''', —NO$_2$, —CN and —(CO)—R;

n is 0 to 4;

R$_3$ is selected from C$_1$-C$_6$ alkyl, C$_3$-C$_6$ cycloalkyl, C$_1$-C$_6$ haloalkyl, C$_2$-C$_6$ alkenyl, C$_2$-C$_6$ alkynyl, heterocyclyl having 5 to 10 ring atoms, aryl having 6 to 10 ring atoms, heteroaryl having 5 to 10 ring atoms, and C$_7$-C$_{16}$ aralkyl, said alkyl, cycloalkyl, haloalkyl, alkenyl, alkynyl, heterocyclyl, aryl, heteroaryl and aralkyl being optionally substituted with one or more substituents independently selected from oxo, halogen, C$_1$-C$_6$ alkyl, C$_1$-C$_6$ alkoxy, C$_1$-C$_6$ haloalkyl, —OH, —NR"R''', —NO$_2$, —CN and —(CO)—R;

each R is independently selected from H, C$_1$-C$_6$ alkyl, C$_1$-C$_6$ alkoxy and —NR"R''';

each R" and R''' is independently selected from H and C$_1$-C$_6$ alkyl.

In a third aspect, the disclosure relates to a pharmaceutical composition comprising a compound of formula (I), (II) or (III), and a pharmaceutically acceptable carrier.

In a fourth aspect, the disclosure relates to a compound of formula (I), (II) or (III) for use in a method for treating cancer.

In a fifth aspect, the disclosure relates to a method for treating cancer, said method comprising administering to a subject a therapeutically efficient amount of (i) a compound of formula (I), (ii) a compound of formula (II) or (III), or (iii) a pharmaceutical composition as described herein.

In a sixth aspect, the disclosure relates to the use of a compound of formula (I), (II) or (III), for the manufacture of a medicament for the treatment of cancer.

In a seventh aspect, the disclosure relates to the use of a compound of formula (I), (II) or (III) for use as a drug.

DETAILED DESCRIPTION

Definitions

As used herein, the terms "C$_1$-C$_6$ alkyl", by itself or as part of another substituent, refer to a linear or branched alkyl functional group having 1 to 6 carbon atoms. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

As used herein, the terms "C$_3$-C$_6$ cycloalkyl" refer to a saturated or unsaturated cyclic group having 3 to 6 carbon atoms. Suitable cycloalkyl groups include cyclopropyl, cyclobutyl, cyclopentyl and cyclohexyl.

As used herein, the term "halogen" refers to a fluoro (—F), chloro (—Cl), bromo (—Br), or iodo (—I) group.

As used herein, the terms "C$_1$-C$_6$ haloalkyl" refer to a C$_1$-C$_6$ alkyl as defined herein that is substituted by one or more halogen group as defined herein. Suitable C$_1$-C$_6$ haloalkyl groups include trifluoromethyl and dichloromethyl.

As used herein, the terms "C$_2$-C$_6$ alkenyl" refer to a straight or branched hydrocarbon moiety having at least one carbon-carbon double bond. Alkenyl groups include, for example, ethenyl (i.e., vinyl), propenyl, butenyl, 1-methyl-2-buten-1-yl, pentenyl, hexenyl, octenyl, and butadienyl.

As used herein, the terms "C$_2$-C$_6$ alkynyl" refer to a straight or branched hydrocarbon moiety having at least one carbon-carbon triple bond. Examples of "alkynyl" include ethynyl, 2-propynyl (propargyl), 1-propynyl, pentynyl, hexynyl, and allenyl groups, and the like.

As used herein, the terms "C$_1$-C$_6$ alkoxy" refer to a —O-alkyl group, wherein the alkyl group is a C$_1$-C$_6$ alkyl as defined herein. Suitable C$_1$-C$_6$ alkoxy groups include methoxy, ethoxy, propoxy.

As used herein, the terms "aryl having 6 to 10 ring atoms" refer to a polyunsaturated, aromatic hydrocarbyl group having a single ring or multiple aromatic rings fused together, containing 6 to 10 ring atoms, wherein at least one ring is aromatic. The aromatic ring may optionally include one to two additional rings (cycloalkyl, heterocyclyl or heteroaryl as defined herein) fused thereto. Suitable aryl groups include phenyl, naphtyl and phenyl ring fused to a heterocyclyl, like benzopyranyl, benzodioxolyl, benzodioxanyl and the like.

As used herein, the terms "heteroaryl having 5 to 10 ring atoms" refer to a polyunsaturated, aromatic ring system having a single ring or multiple aromatic rings fused together or linked covalently, containing 5 to 10 atoms, wherein at least one ring is aromatic and at least one ring atom is a heteroatom selected from N, O and S. The nitrogen and sulfur heteroatoms may optionally be oxidized and the nitrogen heteroatoms may optionally be quaternized. Such rings may be fused to an aryl, cycloalkyl or heterocyclyl ring. Non-limiting examples of such heteroaryl, include: furanyl, thiophenyl, pyrrolyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, isoindolyl, benzofuranyl, isobenzofuranyl, benzothiophenyl, isobenzothiophenyl, indazolyl, benzimidazolyl, benzoxazolyl, purinyl, benzothiadiazolyl, quinolinyl, isoquinolinyl, cinnolinyl, quinazolinyl and quinoxalinyl.

As used herein, the terms "heterocyclyl having 5 to 10 ring atoms" refer to a saturated or unsaturated cyclic group having 5 to 10 ring atoms, wherein at least one ring atom is a heteroatom selected from N, O and S. The nitrogen and sulfur heteroatoms may optionally be oxidized and the nitrogen heteroatoms may optionally be quaternized. Examples of heterocycle include, but are not limited to, tetrahydropyridyl, piperidinyl, morpholinyl, tetrahydrofuranyl, tetrahydrothienyl, piperazinyl, 1-azepanyl, imidazolinyl, 1,4-dioxanyl and the like.

As used herein, the terms "C$_7$-C$_{16}$ aralkyl" refer to an alkyl group as defined herein that is substituted by one or more aryl groups as defined herein. Aralkyl groups include, for example, benzyl groups.

Various embodiments of the disclosure are described herein. It will be recognized that features specified in each embodiment may be combined with other specified features to provide further embodiments.

The present disclosure encompasses the compounds of formula (I), (II), (III), their tautomers, enantiomers, diastereomers, racemates or mixtures thereof, and their hydrates, solvates or pharmaceutically acceptable salts.

The terms "pharmaceutically acceptable salts" refers to salts that retain the biological effectiveness and properties of the compounds of this disclosure and, which typically are not biologically or otherwise undesirable.

Any formula given herein is also intended to represent unlabeled as well as isotopically forms of the compounds, like deuterium labeled compounds or $^{14}$C-labeled compounds.

Compound of Formula (I)

The present disclosure relates to a compound of formula (I)

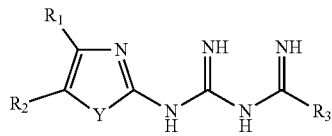

wherein
- $R_1$ and $R_2$ are independently selected from H, halogen, $C_1$-$C_6$ alkyl, $C_3$-$C_6$ cycloalkyl, $C_1$-$C_6$ haloalkyl, $C_2$-$C_6$ alkenyl, $C_2$-$C_6$ alkynyl, heterocyclyl having 5 to 10 ring atoms, aryl having 6 to 10 ring atoms, heteroaryl having 5 to 10 ring atoms, and $C_7$-$C_{16}$ aralkyl, said alkyl, cycloalkyl, haloalkyl, alkenyl, alkynyl, heterocyclyl, aryl, heteroaryl and aralkyl being optionally substituted with one or more substituents independently selected from oxo, halogen, $C_1$-$C_6$ alkyl, $C_1$-$C_6$ alkoxy, $C_1$-$C_6$ haloalkyl, —OH, —NR"R'", —NO$_2$, —CN and —(CO)—R;
- or $R_1$ and $R_2$, together with the carbon-carbon double bond between them, form a 6 to 10 membered aryl or heteroaryl ring, said aryl and heteroaryl being optionally substituted with one or more substituents independently selected from halogen, $C_1$-$C_6$ alkyl, $C_1$-$C_6$ alkoxy, $C_1$-$C_6$ haloalkyl, —OH, —NR"R'", —NO$_2$, —CN and —(CO)—R;
- Y is –O— or —S—;
- $R_3$ is selected from $C_1$-$C_6$ alkyl, $C_3$-$C_6$ cycloalkyl, $C_1$-$C_6$ haloalkyl, $C_2$-$C_6$ alkenyl, $C_2$-$C_6$ alkynyl, heterocyclyl having 5 to 10 ring atoms, aryl having 6 to 10 ring atoms, heteroaryl having 5 to 10 ring atoms and $C_7$-$C_{16}$ aralkyl, said alkyl, cycloalkyl, haloalkyl, alkenyl, alkynyl, heterocyclyl, aryl, heteroaryl and aralkyl being optionally substituted with one or more substituents independently selected from oxo, halogen, $C_1$-$C_6$ alkyl, $C_1$-$C_6$ alkoxy, $C_1$-$C_6$ haloalkyl, —OH, —NR"R'", —NO$_2$, —CN and —(CO)—R;
- each R is independently selected from H, $C_1$-$C_6$ alkyl, $C_1$-$C_6$ alkoxy and —NR"R'";
- each R" and R'" is independently selected from H and $C_1$-$C_6$ alkyl.

In one embodiment, the disclosure relates to a compound of formula (I) wherein
- $R_1$ and $R_2$ are independently selected from H, halogen, $C_1$-$C_6$ alkyl, $C_3$-$C_6$ cycloalkyl, $C_1$-$C_6$ haloalkyl, heterocyclyl having 5 to 10 ring atoms, aryl having 6 to 10 ring atoms, heteroaryl having 5 to 10 ring atoms and $C_7$-$C_{16}$ aralkyl, said alkyl, cycloalkyl, heterocyclyl, aryl, heteroaryl and aralkyl being optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R;
- or $R_1$ and $R_2$, together with the carbon-carbon double bond between them, form a 6 membered aryl or heteroaryl ring, said aryl and heteroaryl being optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R;
- Y is –O— or —S—;
- $R_3$ is selected from $C_1$-$C_6$ alkyl, $C_3$-$C_6$ cycloalkyl, $C_1$-$C_6$ haloalkyl, heterocyclyl having 5 to 10 ring atoms, aryl having 6 to 10 ring atoms, heteroaryl having 5 to 10 ring atoms and $C_7$-$C_{16}$ aralkyl, said alkyl, cycloalkyl, heterocyclyl, aryl, heteroaryl and aralkyl being optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R;
- each R is independently selected from H, $C_1$-$C_6$ alkyl and $C_1$-$C_6$ alkoxy.

In one embodiment, $R_1$ is selected from H, $C_1$-$C_6$ alkyl and aryl having 6 to 10 ring atoms, said alkyl, and aryl, being optionally substituted with one or more substituents independently selected from halogen, $C_1$-$C_6$ alkyl, $C_1$-$C_6$ alkoxy, and —NO$_2$.

In another embodiment, $R_2$ is selected from H and $C_1$-$C_6$ alkyl, said alkyl being optionally substituted with one or more substituents independently selected from halogen.

In another embodiment, $R_1$ and $R_2$ are independently selected from H, $C_1$-$C_6$ alkyl and aryl having 6 to 10 ring atoms, said aryl, being optionally substituted with one or more —NO$_2$.

In another embodiment, $R_1$ and $R_2$, together with the carbon-carbon double bond between them, form a 6 membered aryl ring, optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R; each R is independently selected from H, $C_1$-$C_6$ alkyl and $C_1$-$C_6$ alkoxy.

In another embodiment, $R_3$ is selected from $C_1$-$C_6$ haloalkyl, heterocyclyl having 5 to 10 ring atoms, aryl having 6 to 10 ring atoms and heteroaryl having 5 to 10 ring atoms, said heterocyclyl, aryl, and heteroaryl being optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R; each R being independently selected from $C_1$-$C_6$ alkyl.

In another embodiment, Y is —S—.

In another embodiment, the disclosure provides a compound of formula (I), wherein
- $R_1$ and $R_2$, together with the carbon-carbon double bond between them, form a 6-membered aryl ring;
- Y is —O—;
- $R_3$ is selected from aryl having 6 to 10 ring atoms, said aryl being optionally substituted with one or more substituents independently selected from halogen.

In another embodiment, the disclosure provides a compound of formula (I), wherein
- $R_1$ and $R_2$ are independently selected from H, $C_1$-$C_6$ alkyl and aryl having 6 to 10 ring atoms, said aryl, being optionally substituted with one or more —NO$_2$;
- or $R_1$ and $R_2$, together with the carbon-carbon double bond between them, form a 6 membered aryl ring, optionally substituted with one or more substituents independently selected from halogen, $C_1$-$C_6$ alkyl and $C_1$-$C_6$ alkoxy,
- Y is —S—;
- $R_3$ is selected from $C_1$-$C_6$ haloalkyl, heterocyclyl having 5 to 10 ring atoms, aryl having 6 to 10 ring atoms, heteroaryl having 5 to 10 ring atoms, and $C_7$-$C_{16}$ aralkyl said heterocyclyl, aryl, heteroaryl and aralkyl being optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R;
- each R is independently selected from $C_1$-$C_6$ alkyl.

In another embodiment, the disclosure provides a compound of formula (I), wherein $R_1$ and $R_2$, together with the carbon-carbon double bond between them, form a 6-membered aryl ring, Y is —S—;

$R_3$ is selected from aryl having 6 to 10 ring atoms and heteroaryl having 5 to 10 ring atoms, said aryl and heteroaryl being optionally substituted with one or more substituents independently selected from halogen, $C_1$-$C_6$ haloalkyl, $C_1$-$C_6$ alkoxy, —CN and —(CO)—R; each R being independently selected from $C_1$-$C_6$ alkyl.

In another embodiment, the compound of formula (I) is selected from

MTF 242

MTF 243

MTF 244

MTF 245

MTF 246

MTF 247

-continued

MTF 248

MTF 249

MTF 250

MTF 251

MTF 252

MTF 253

MTF 254

MTF 255

MTF 256
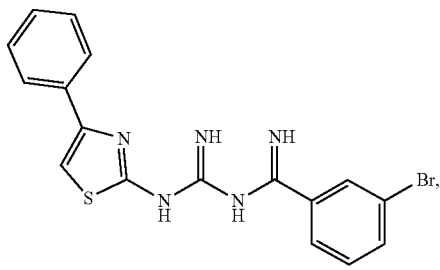
MTF 262
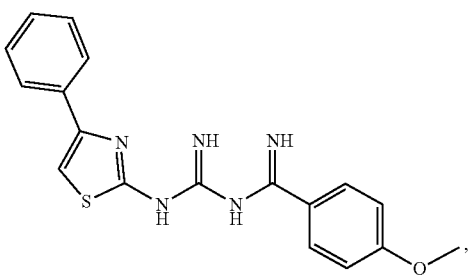
MTF 257
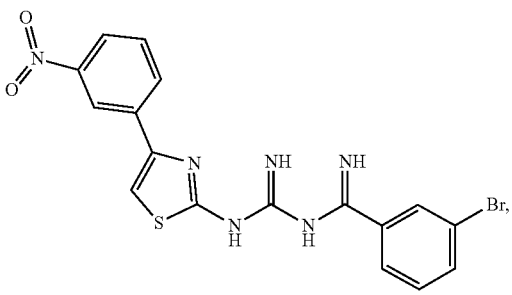
MTF 263
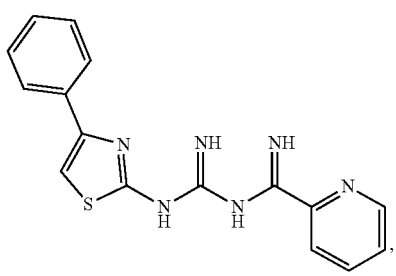
MTF 259
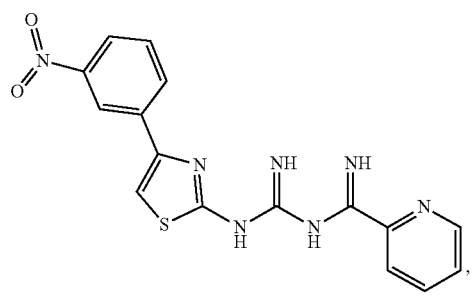
MTF 264
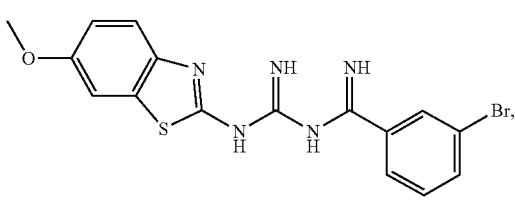
MTF 265
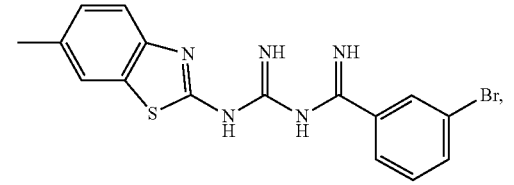
MTF 260
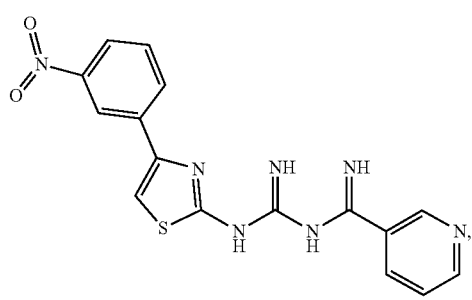
MTF 267
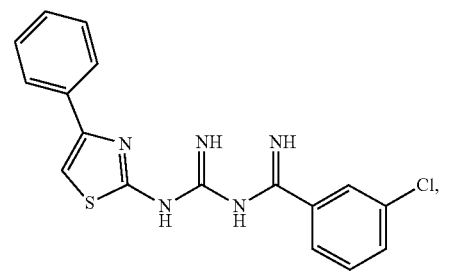
MTF 261
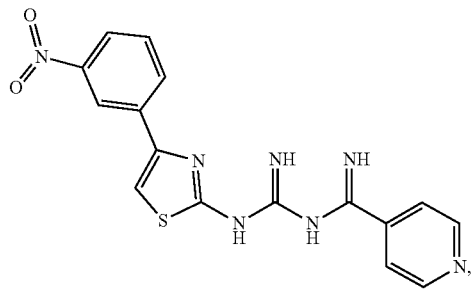
MTF 268
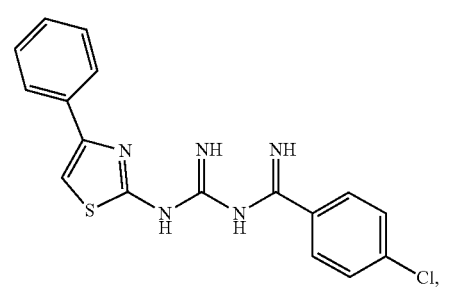

MTF 272
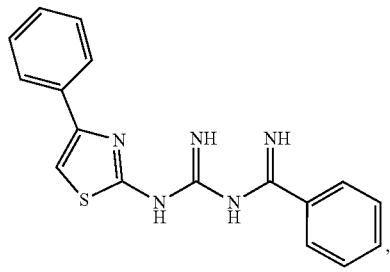
MTF 273
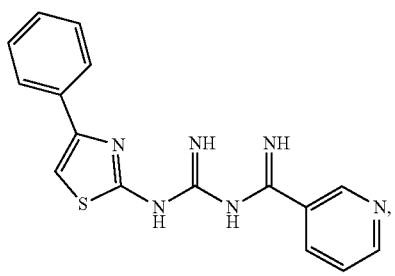
MTF 274
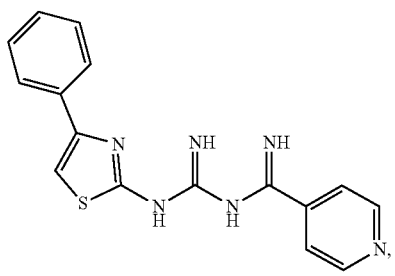
MTF 276
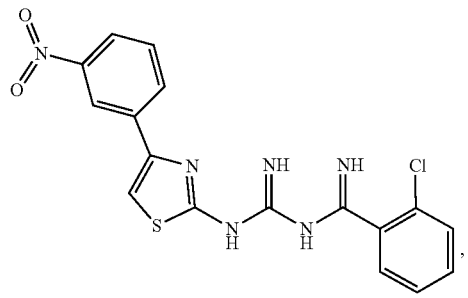
MTF 277
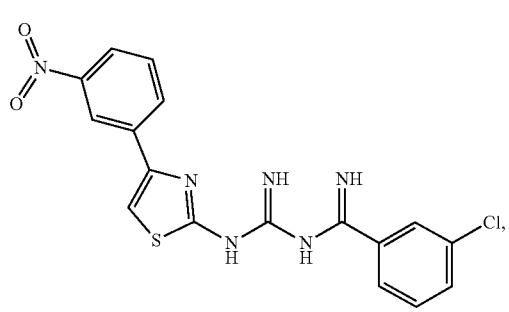
MTF 281
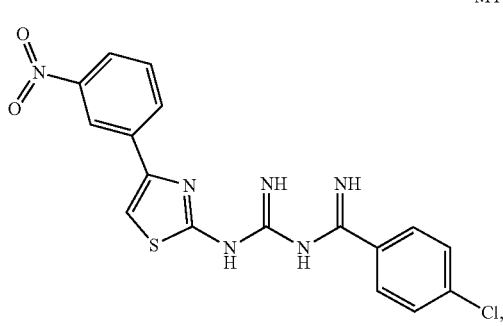
MTF 283
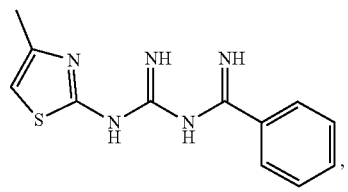
MTF 284
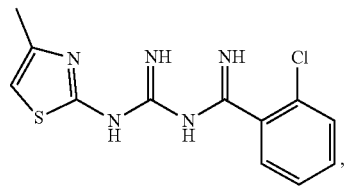
MTF 285
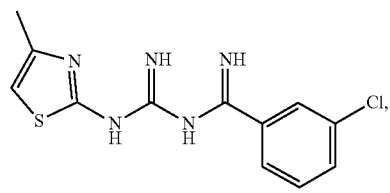
MTF 286
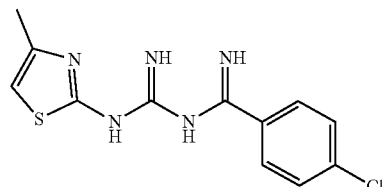
MTF 287
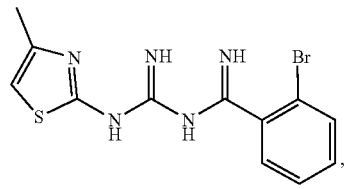
MTF 288
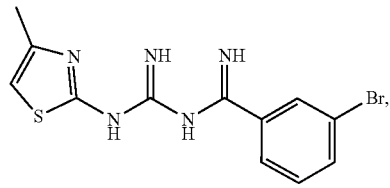

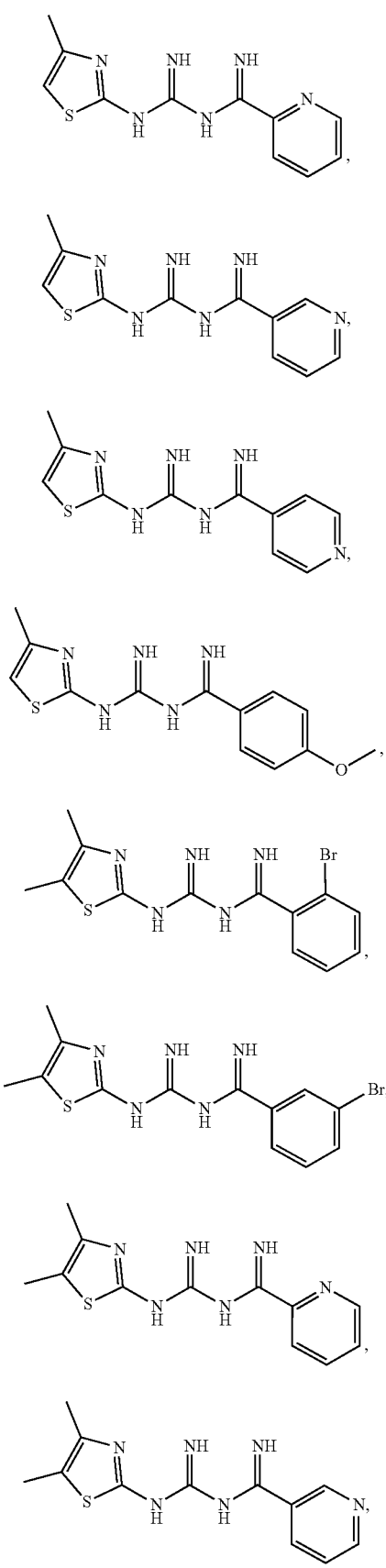
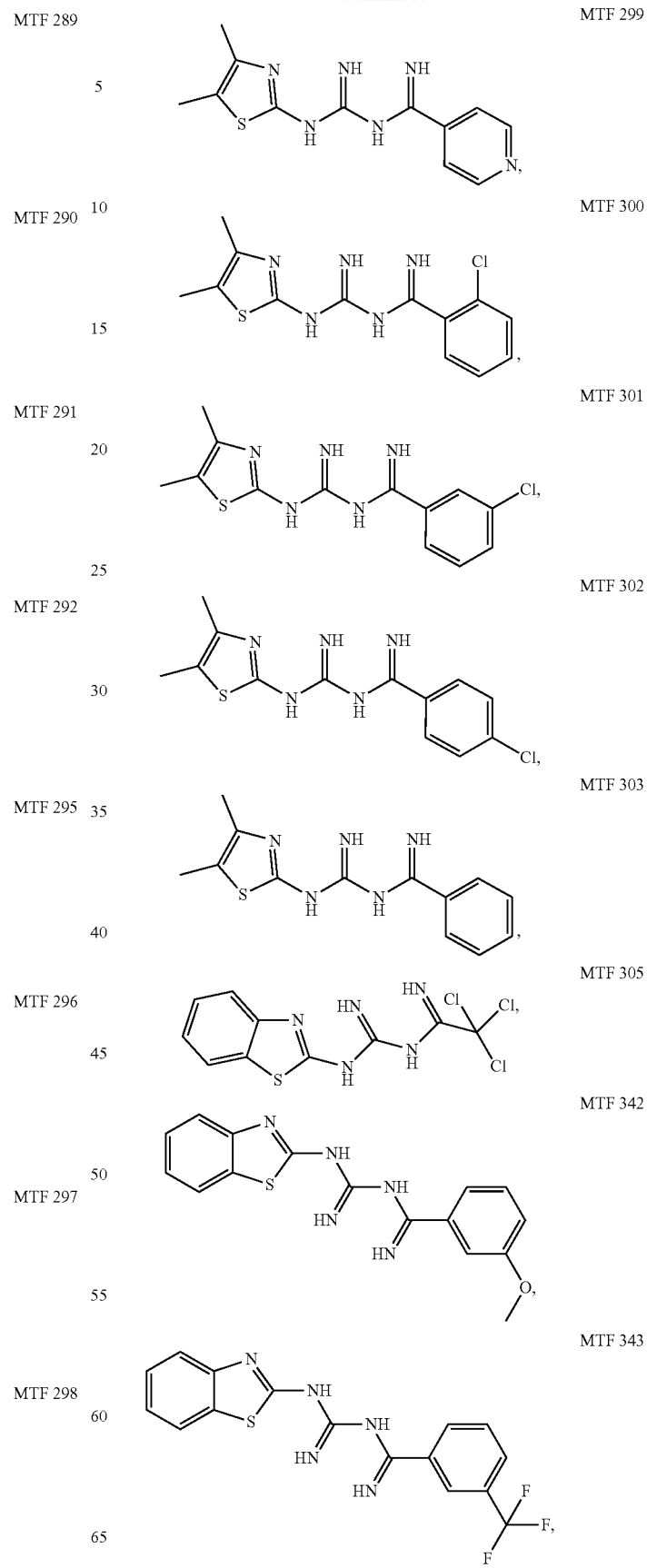

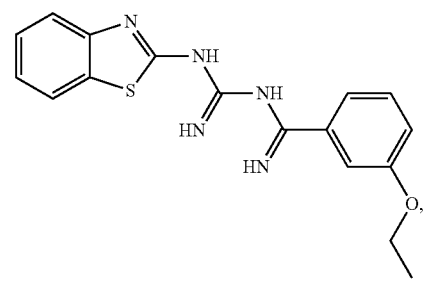
MTF 344
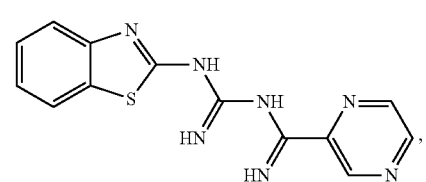
MTF 345
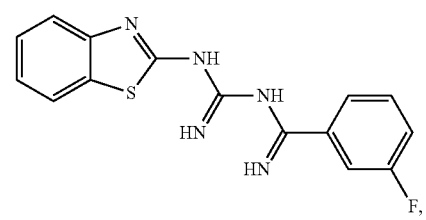
MTF 346
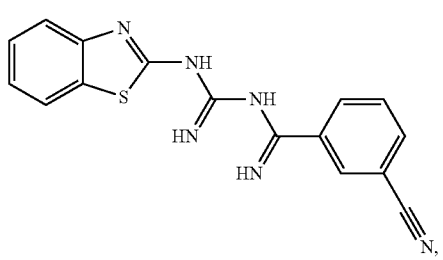
MTF 347
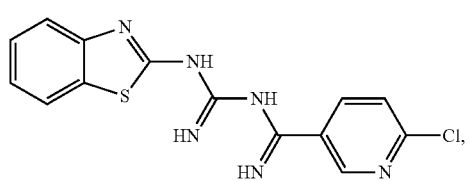
MTF 379
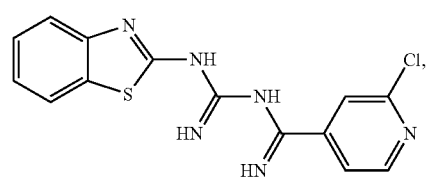
MTF 380
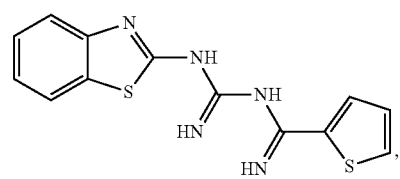
MTF 381
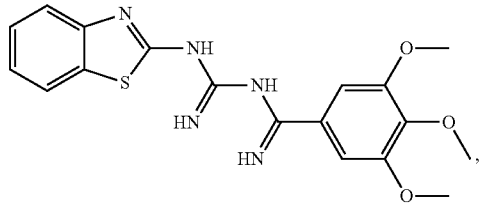
MTF 382
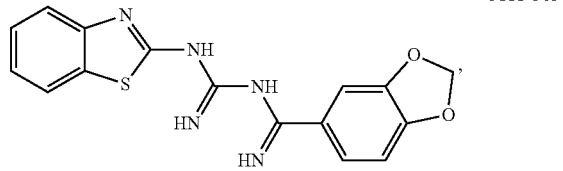
MTF 383
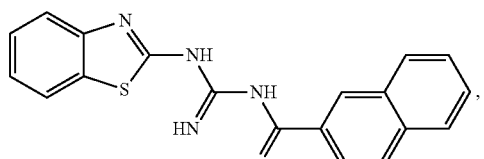
MTF 384
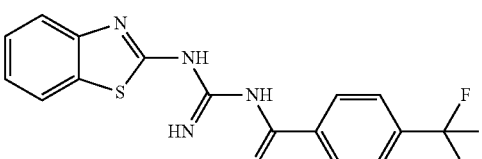
MTF 385
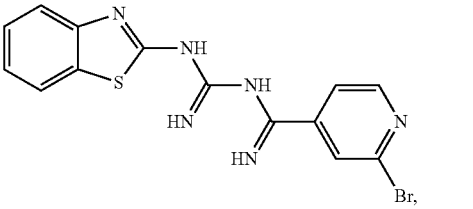
MTF 386
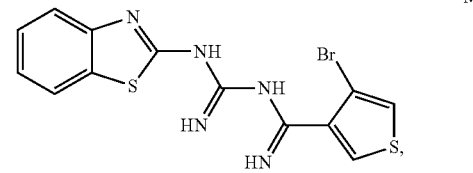
MTF 387
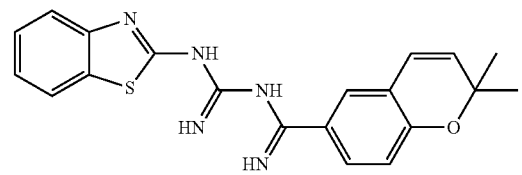
MTF 388
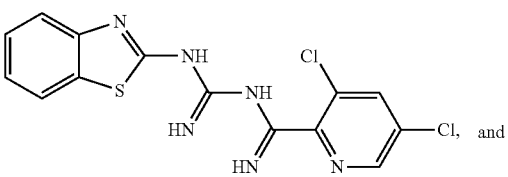
MTF 389

-continued
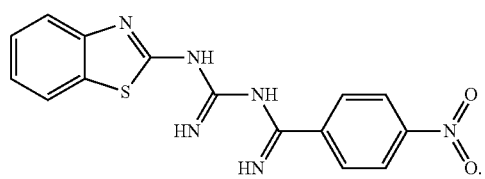
MTF 398
According to one embodiment, the compound of formula (I) is selected from
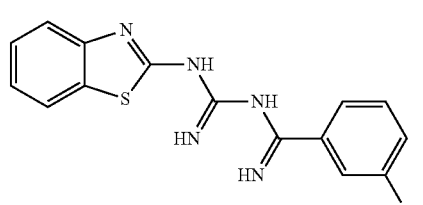
MTF 242
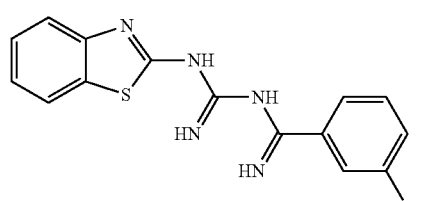
MTF 243
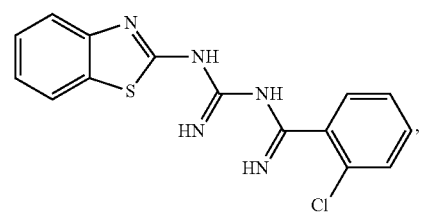
MTF 244
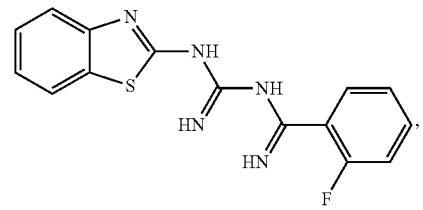
MTF 249
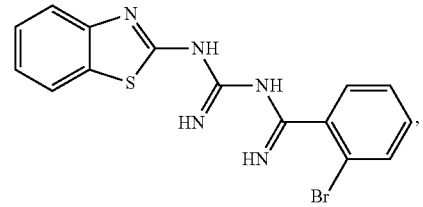
MTF 250
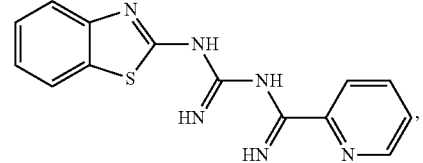
MTF 251
-continued
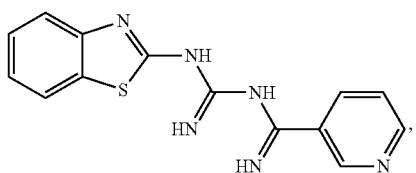
MTF 252
MTF 253
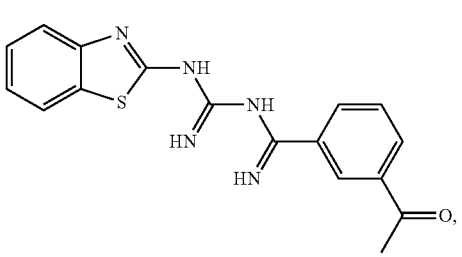
MTF 255
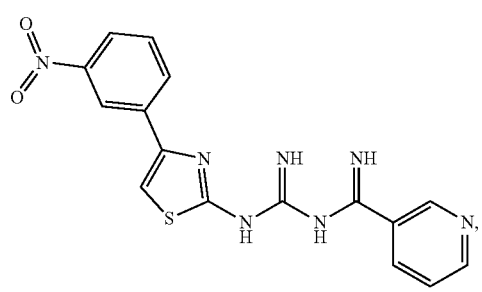
MTF 260
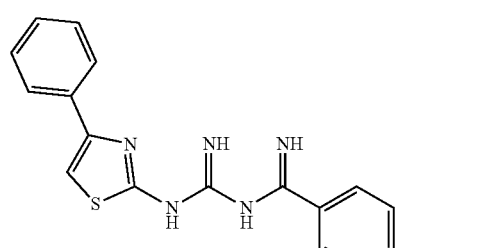
MTF 262
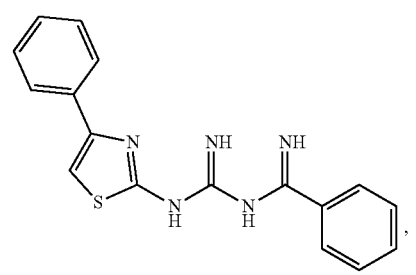
MTF 272

MTF 276
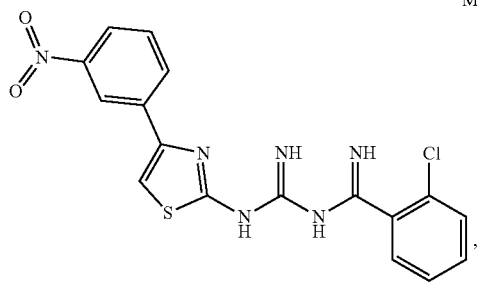
MTF 289
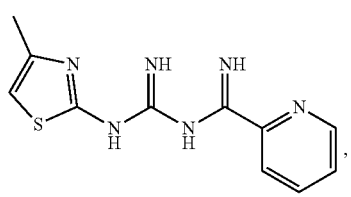
MTF 290
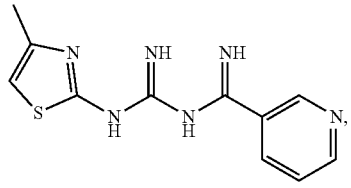
MTF 296
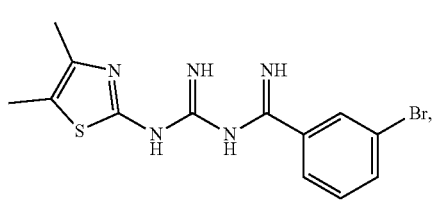
MTF 297
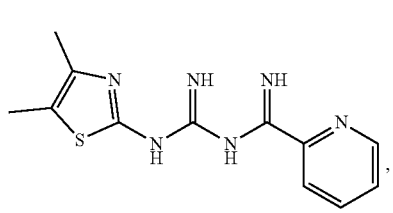
MTF 298
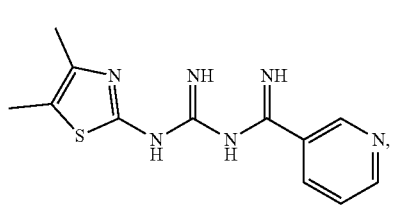
MTF 299
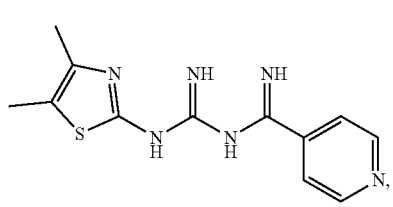
MTF 300
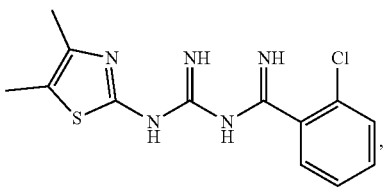
MTF 303
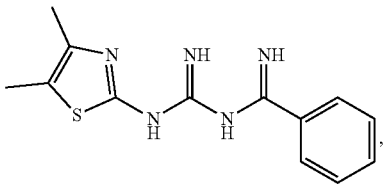
MTF 305
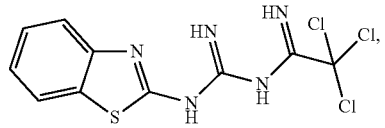
MTF 342
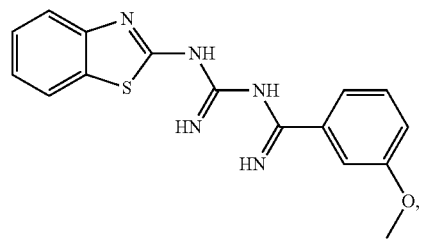
MTF 343
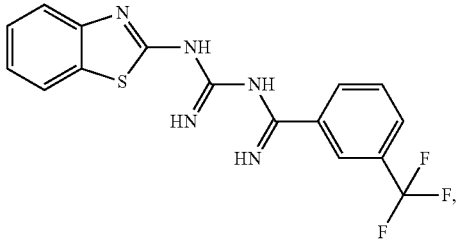
MTF 344
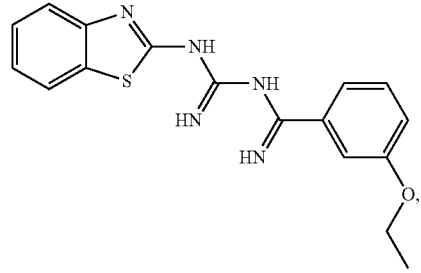
MTF 345
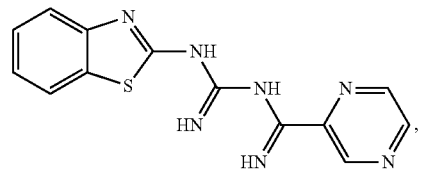

-continued
MTF 346
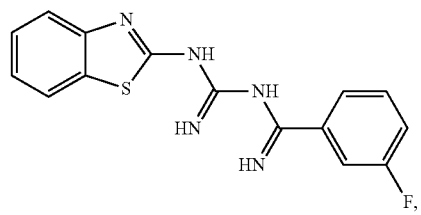
MTF 347
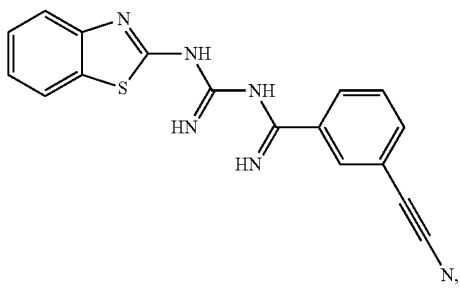
MTF 380
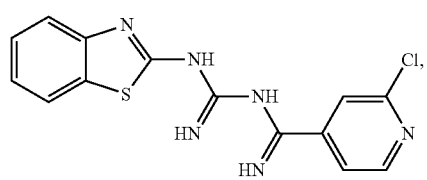
MTF 382
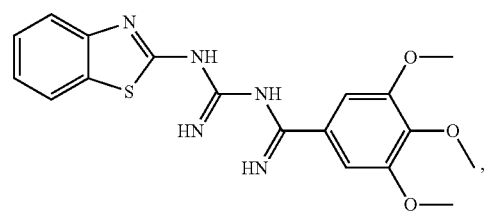
MTF 383
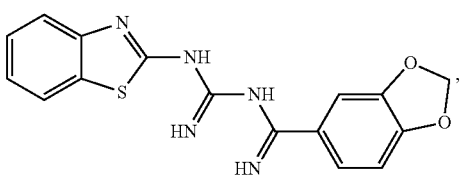
MTF 386
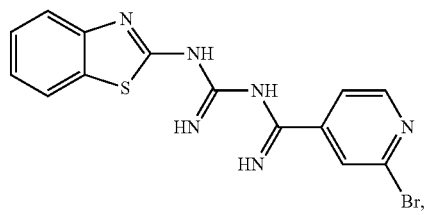
MTF 387
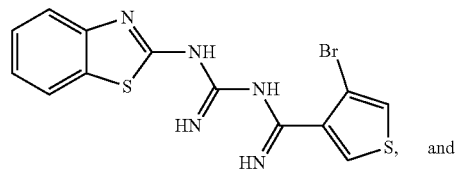
and
MTF 388
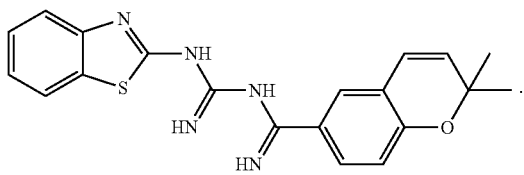
In a preferred embodiment, the compound of formula (I) is selected from
MTF 242
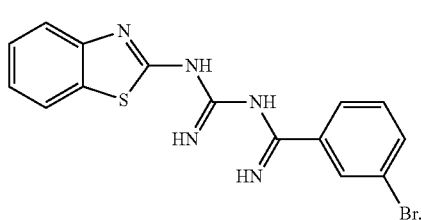
MTF 243
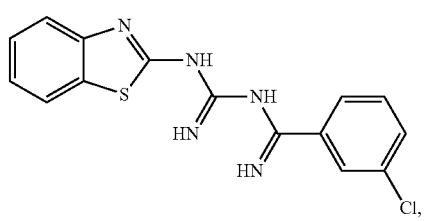
MTF 250
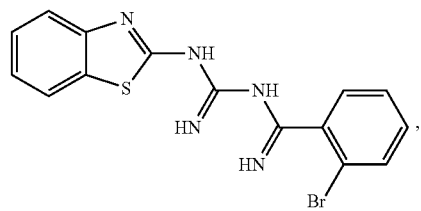
MTF 252
MTF 253
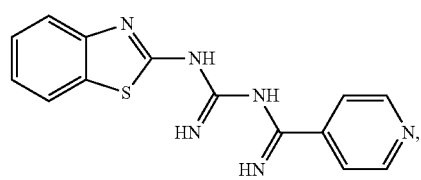
MTF 255
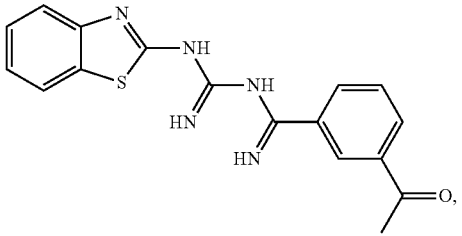

MTF 345, MTF 347, MTF 380, MTF 382, and MTF 386

In some embodiments, the compounds of formula (I) as described herein have anti-proliferative activity towards melanoma cell lines. Accordingly, they may advantageously be used in a method for treating cancer, and melanoma in particular.

Without being bound to this theory, the inventors hypothesized that, in some embodiments, the compounds of formula (I) induce the activation of AMPK (AMP activated protein kinase) which is involved in the regulation of apoptosis, thereby inducing cell death to cancer cells.

Compounds of Formula (II) or (III)

Compounds of formula (I) wherein $R_1$ and $R_2$, together with the carbon-carbon double bond between them, form an optionally substituted 6-membered aryl ring, can spontaneously, or under specific conditions depending on the biguanide structure, rearrange to form compounds of formula (II) by opening of the benzothiazole or benzoxazole moiety and formation of a triazine ring. For example, in some cases, when a compound of formula (I) with Y is —S— is treated in oxidative conditions, rearrangement to a compound of formula (II) occurs. When Y' is —SH, compounds of formula (II) can dimerize to form compounds of formula (III) by formation of an S—S bond.

Therefore, the disclosure also relates to a compound of formula (II) or (III)

wherein
Y' is —SR$_4$ or –OR$_5$,
$R_4$ is selected from H, $C_1$-$C_6$ alkyl and protecting groups;
$R_5$ is selected from H and protecting groups;
each R' is independently selected from halogen, $C_1$-$C_6$ alkyl, $C_1$-$C_6$ alkoxy, $C_1$-$C_6$ haloalkyl, —OH, —NR"R''', —NO$_2$, —CN and —(CO)—R;
n is 0 to 4;
$R_3$ is selected from $C_1$-$C_6$ alkyl, $C_3$-$C_6$ cycloalkyl, $C_1$-$C_6$ haloalkyl, $C_2$-$C_6$ alkenyl, $C_2$-$C_6$ alkynyl, heterocyclyl having 5 to 10 ring atoms, aryl having 6 to 10 ring atoms, heteroaryl having 5 to 10 ring atoms and $C_7$-$C_{16}$ aralkyl, said alkyl, cycloalkyl, haloalkyl, alkenyl, alkynyl, heterocyclyl, aryl, heteroaryl and aralkyl being optionally substituted with one or more substituents independently selected from oxo, halogen, $C_1$-$C_6$ alkyl, $C_1$-$C_6$ alkoxy, $C_1$-$C_6$ haloalkyl, —OH, —NR"R''', —NO$_2$, —CN and —(CO)—R;
each R is independently selected from H, $C_1$-$C_6$ alkyl, $C_1$-$C_6$ alkoxy and —NR"R''';
each R" and R''' is independently selected from H and $C_1$-$C_6$ alkyl.

In one embodiment, the disclosure relates to a compound of formula (II) or (III), wherein
Y' is —SR$_4$ or –OR$_5$,
$R_4$ is selected from H, $C_1$-$C_6$ alkyl and protecting groups;
$R_5$ is selected from H and protecting groups;
each R' is independently selected from halogen, $C_1$-$C_6$ alkyl, $C_1$-$C_6$ alkoxy, $C_1$-$C_6$ haloalkyl, —NO$_2$, —CN and —(CO)—R;
n is 0 to 4;
$R_3$ is selected from $C_1$-$C_6$ alkyl, $C_1$-$C_6$ haloalkyl, heterocyclyl having 5 to 10 ring atoms, aryl having 6 to 10 ring atoms, heteroaryl having 5 to 10 ring atoms and $C_7$-$C_{16}$ aralkyl, said alkyl, heterocyclyl, aryl, heteroaryl and aralkyl being optionally substituted with one or more substituents independently selected from halogen, $C_1$-$C_6$ alkyl, $C_1$-$C_6$ alkoxy, $C_1$-$C_6$ haloalkyl, —NO$_2$, —CN and —(CO)—R; each R is independently selected from H, $C_1$-$C_6$ alkyl and $C_1$-$C_6$ alkoxy.

In one embodiment, n is 1 and R' is selected from halogen and $C_1$-$C_6$ alkoxy. In another embodiment, n is 1 and R' is selected from halogen, $C_1$-$C_6$ alkyl, $C_1$-$C_6$ alkoxy, and —NO$_2$.

In another embodiment, n is 0.

In another embodiment, Y' is —SR$_4$ and R$_4$ is selected from $C_1$-$C_6$ alkyl and protecting groups, preferably, the protecting group is selected from any group linked by a disulfide function, thioesters, alkyl, alkenyl and alkynyl thioethers, benzyl thioethers, alkylarylmethyl thioethers, and triarylmethylthioethers.

In another embodiment, Y' is —OR$_5$ and R$_5$ is selected from H and protecting groups, preferably, the protecting group is selected from esters, alkenyl and alkynyl ethers, silylated ethers, alkoxymethyl ethers, benzyl ethers tetrahydropyranyl ethers, pentoses, and hexoses.

In an embodiment, Y' is —OH, n is 1, and R' is selected from halogen, and —NO$_2$.

In another embodiment, R$_3$ is selected from $C_1$-$C_6$ haloalkyl, aryl having 6 to 10 ring atoms, heteroaryl having 5 to 10 ring atoms and $C_7$-$C_{16}$ aralkyl, said aryl, heteroaryl and aralkyl being optionally substituted with one or more substituents independently selected from halogen, $C_1$-$C_6$ alkoxy, $C_1$-$C_6$ haloalkyl, and —CN.

In another embodiment, the disclosure provides a compound of formula (II) or (III), wherein
Y' is —SR$_4$, R$_4$ being selected from $C_1$-$C_6$ alkyl;
each R' is independently selected from halogen and $C_1$-$C_6$ alkoxy;
n is 0 to 1;
R$_3$ is selected from $C_1$-$C_6$ haloalkyl, aryl having 6 to 10 ring atoms, heteroaryl having 5 to 10 ring atoms, and $C_7$-$C_{16}$ aralkyl, said aryl, heteroaryl and aralkyl being optionally substituted with one or more substituents independently selected from halogen, $C_1$-$C_6$ alkoxy, and —CN.

In another embodiment, the disclosure provides a compound of formula (II), wherein
Y' is —SR$_4$, R$_4$ being selected from $C_1$-$C_6$ alkyl;
each R' is independently selected from halogen and $C_1$-$C_6$ alkoxy;
n is 0 to 1;
R$_3$ is selected from $C_1$-$C_6$ haloalkyl, aryl having 6 to 10 ring atoms, heteroaryl having 5 to 10 ring atoms and $C_7$-$C_{16}$ aralkyl, said aryl, heteroaryl and aralkyl being optionally substituted with one or more substituents independently selected from halogen, $C_1$-$C_6$ alkoxy, and —CN.

In another embodiment, the disclosure provides a compound of formula (II), wherein
Y' is —OR$_5$ and R$_5$ is H;
each R' is independently selected from halogen, $C_1$-$C_6$ alkyl, and —NO$_2$,
n is 0 to 1;
R$_3$ is selected from $C_1$-$C_6$ haloalkyl, aryl having 6 to 10 ring atoms, and heteroaryl having 5 to 10 ring atoms, said aryl, and heteroaryl being optionally substituted with one or more substituents independently selected from halogen, $C_1$-$C_6$ alkoxy, and —CN.

In another embodiment, the disclosure provides a compound of formula (II), wherein
each R' is independently selected from halogen and $C_1$-$C_6$ alkoxy;
n is 0 to 1;
R$_3$ is selected from $C_1$-$C_6$ haloalkyl, aryl having 6 to 10 ring atoms, heteroaryl having 5 to 10 ring atoms and $C_7$-$C_{16}$ aralkyl, said aryl, heteroaryl and aralkyl being optionally substituted with one or more substituents independently selected from halogen, $C_1$-$C_6$ alkoxy, and —CN.

In another embodiment, the disclosure provides a compound of formula (II) selected from

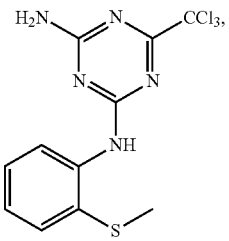

MTF 316

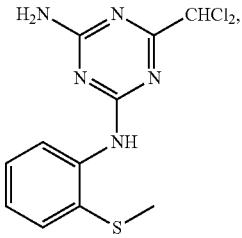

MTF 317

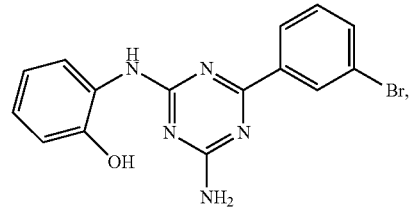

MTF 331

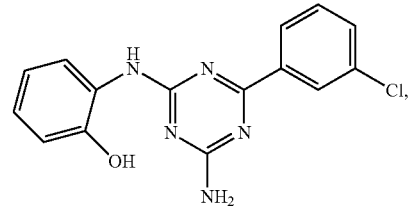

MTF 332

MTF 373

Molecular Weight: 320,5580

-continued
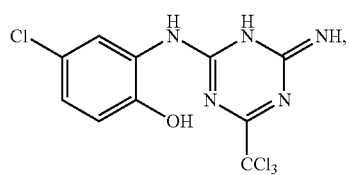
MTF 374
Molecular Weight: 355,0000
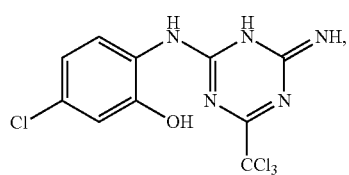
MTF 375
Molecular Weight: 355,00000
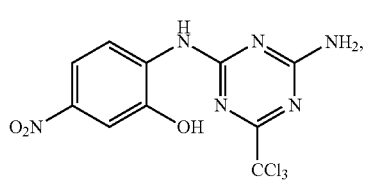
MTF 376
Molecular Weight: 365,5550
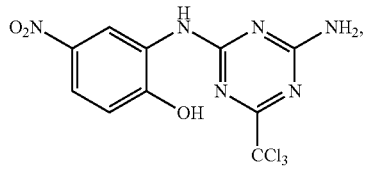
MTF 377
Molecular Weight: 365,5550
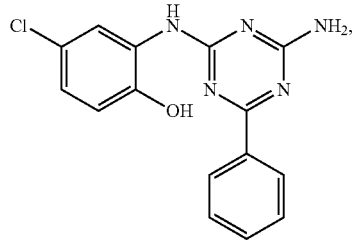
MTF 409
Molecular Weight: 313,74500
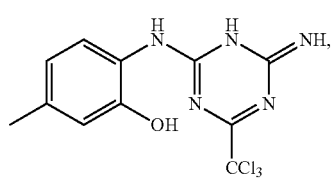
MTF 410
Molecular Weight: 334,58500
-continued
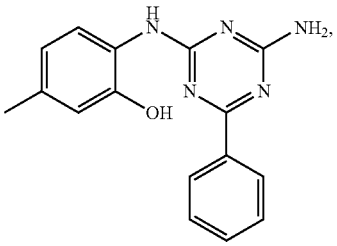
MTF 411
Molecular Weight: 293,33000
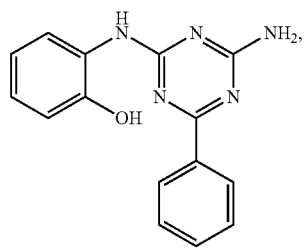
MTF 412
Molecular Weight: 279,3030
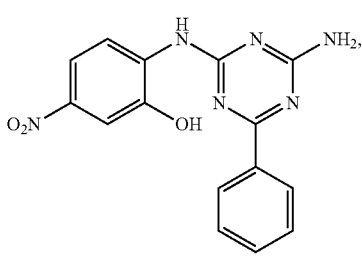
MTF 413
Molecular Weight: 324,3000
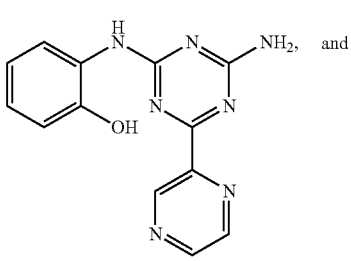
MTF 439
Molecular Weight: 281,2790
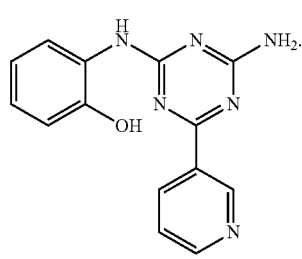
MTF 440
Molecular Weight: 280,2910
In another embodiment, the disclosure provides a compound of formula (II) selected from

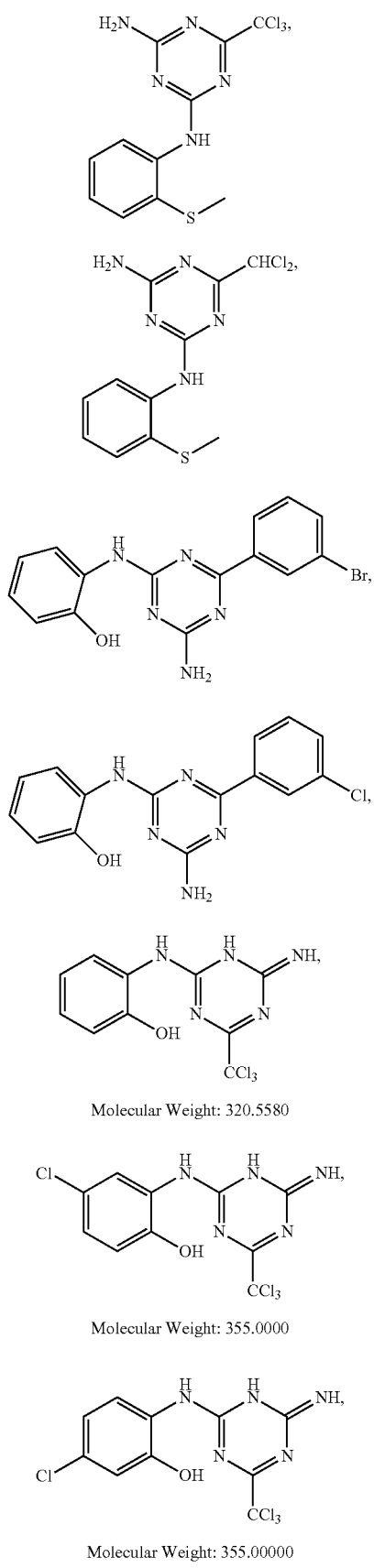

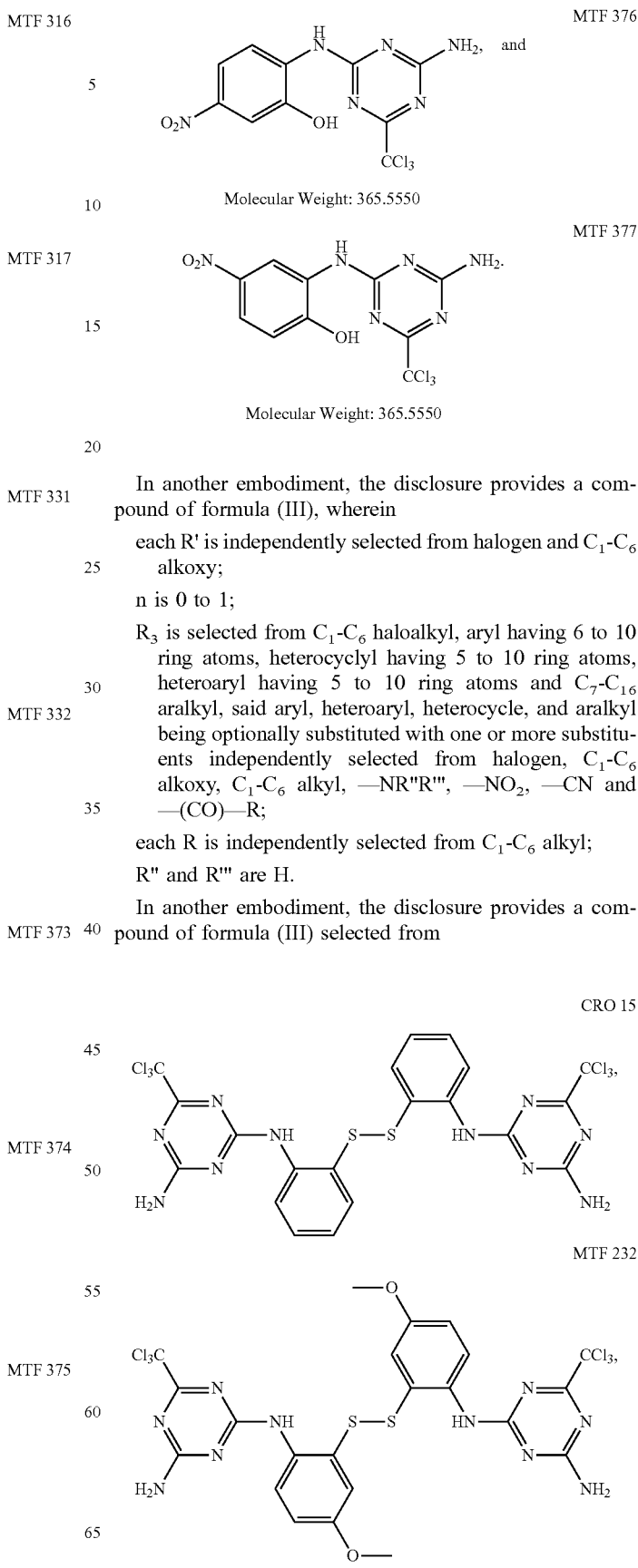

In another embodiment, the disclosure provides a compound of formula (III), wherein each R' is independently selected from halogen and $C_1$-$C_6$ alkoxy;

n is 0 to 1;

$R_3$ is selected from $C_1$-$C_6$ haloalkyl, aryl having 6 to 10 ring atoms, heterocyclyl having 5 to 10 ring atoms, heteroaryl having 5 to 10 ring atoms and $C_7$-$C_{16}$ aralkyl, said aryl, heteroaryl, heterocycle, and aralkyl being optionally substituted with one or more substituents independently selected from halogen, $C_1$-$C_6$ alkoxy, $C_1$-$C_6$ alkyl, —NR"R'", —NO$_2$, —CN and —(CO)—R;

each R is independently selected from $C_1$-$C_6$ alkyl;

R" and R'" are H.

In another embodiment, the disclosure provides a compound of formula (III) selected from MTF 233
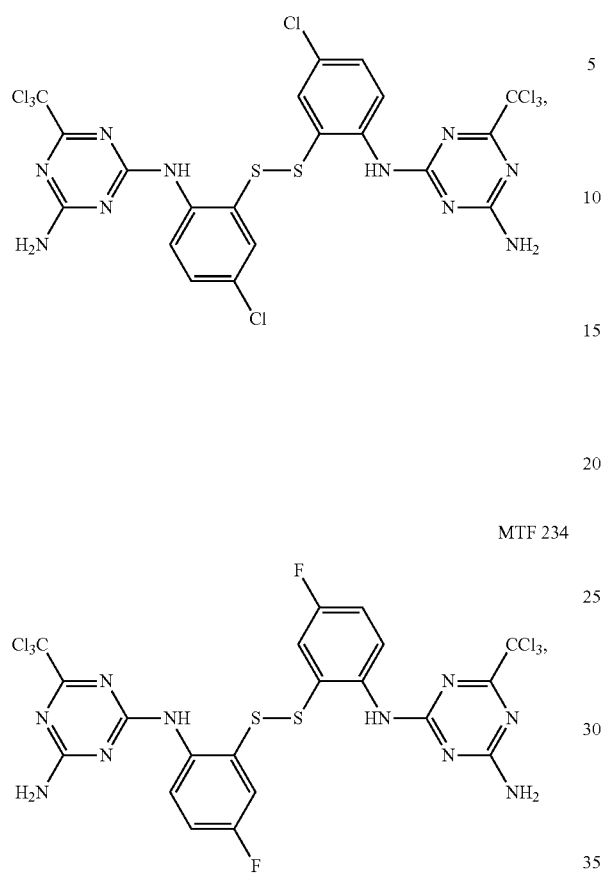
MTF 234
MTF 318
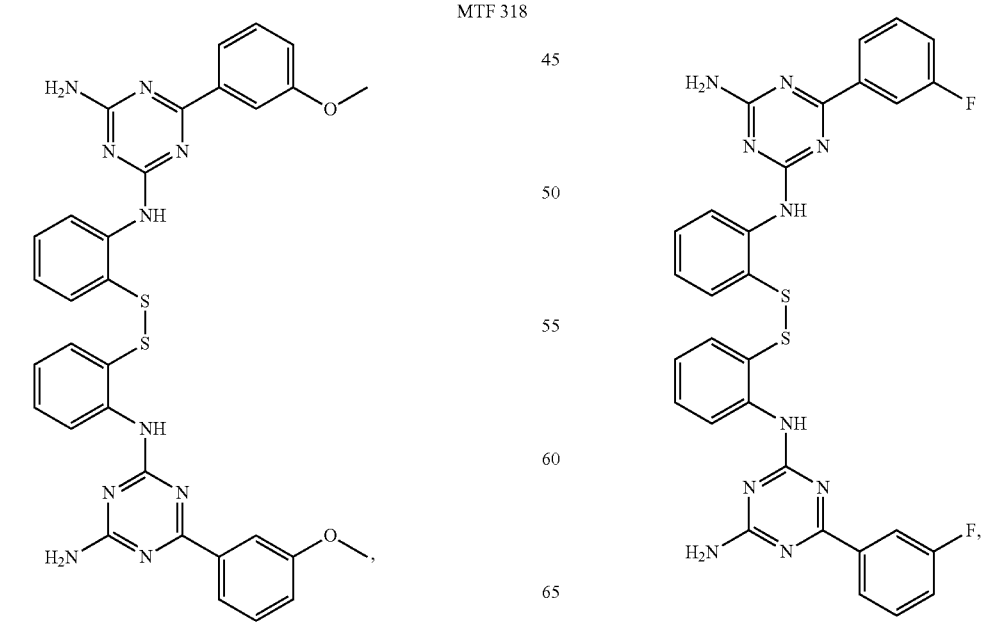
MTF 319
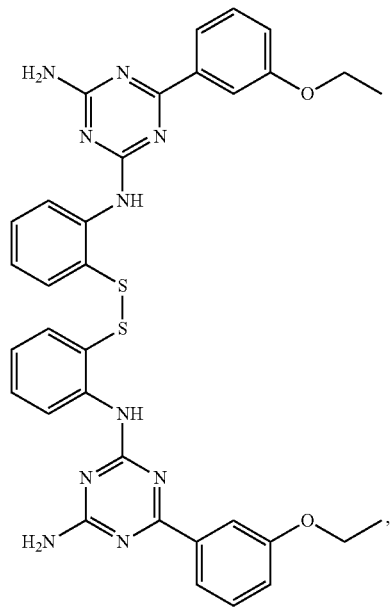
MTF 320

-continued
MTF 321
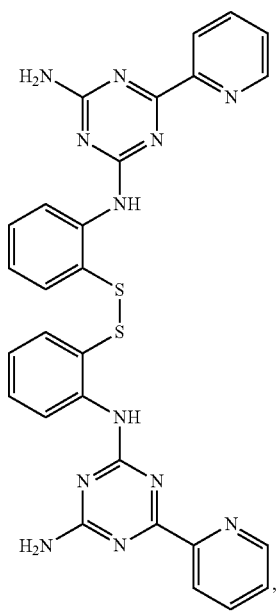
MTF 322
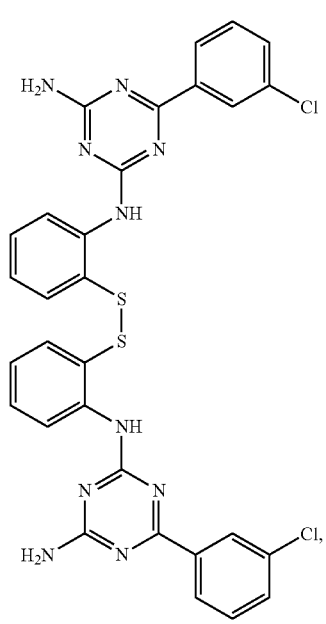
-continued
MTF 323
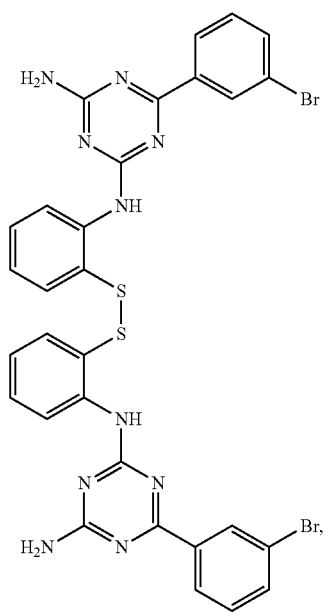
MTF 324

MTF 325
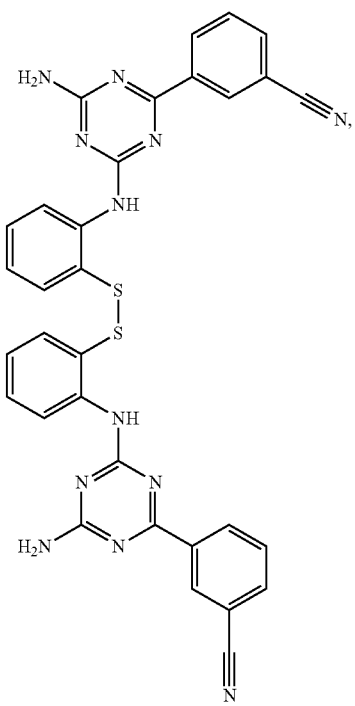
MTF 327
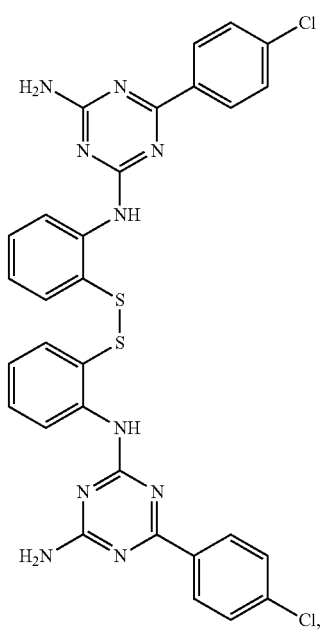
MTF 326
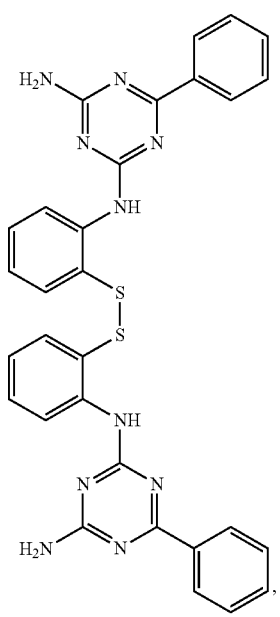
MTF 328
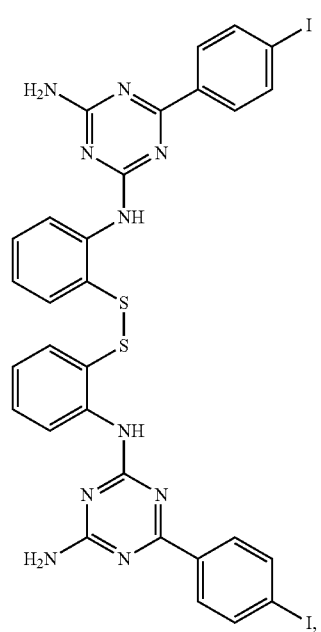

MTF 329
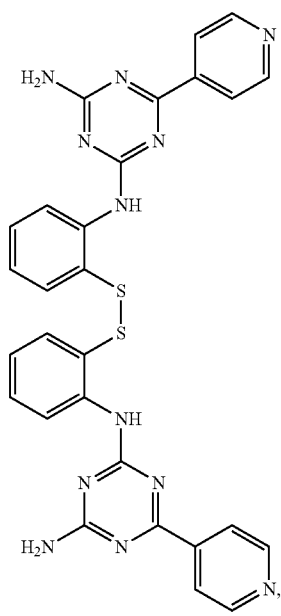
MTF 333
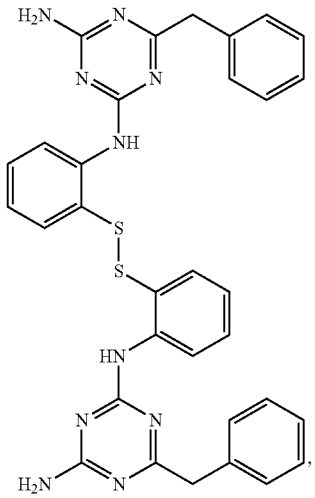
MTF 330
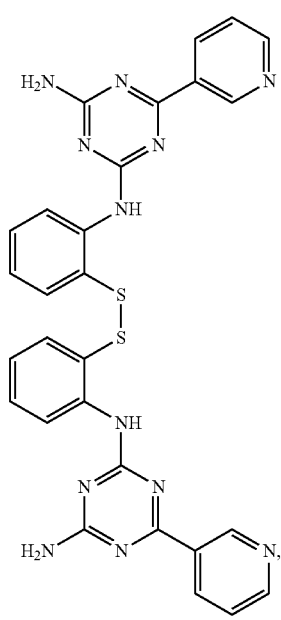
MTF 348
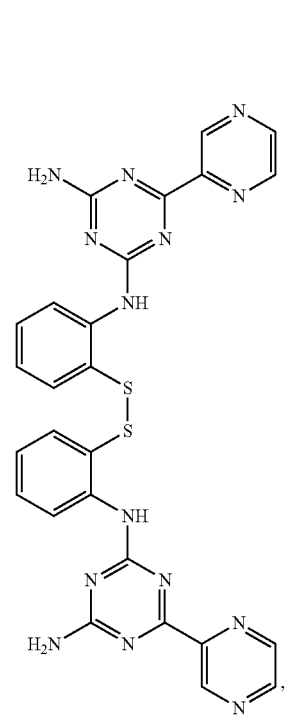

MTF 394

MTF 397

MTF 396

MTF 443

Molecular Weight: 688.8320

MTF 444

Molecular Weight: 752.9160

MTF 445
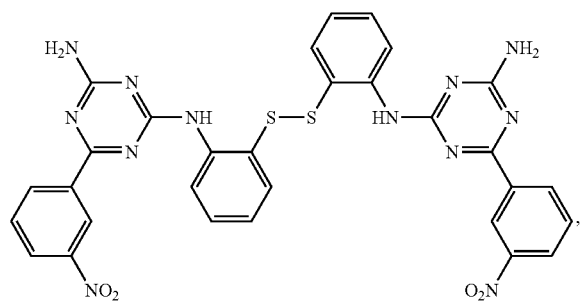
Molecular Weight: 678.7060
MTF 446
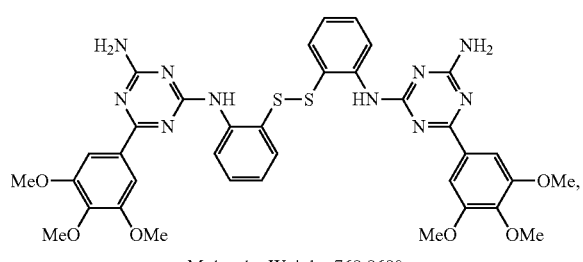
Molecular Weight: 768.8680
MTF 449
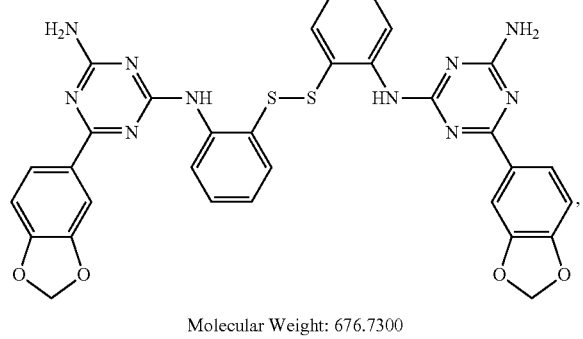
Molecular Weight: 676.7300
MTF 450
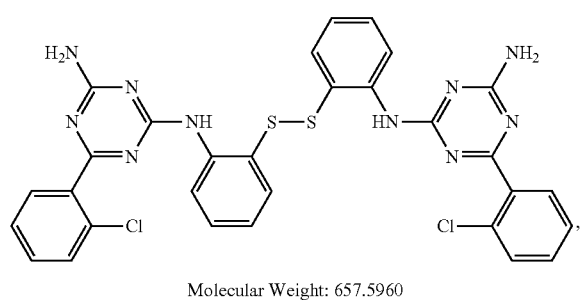
Molecular Weight: 657.5960
MTF 451
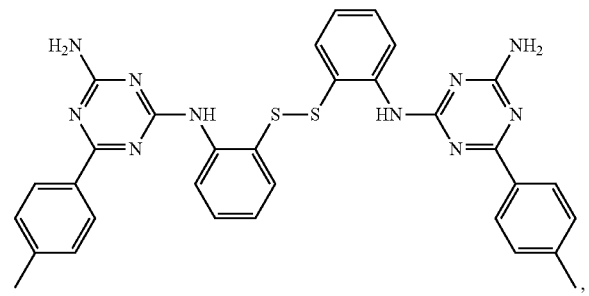
Molecular Weight: 616.7660
MTF 452
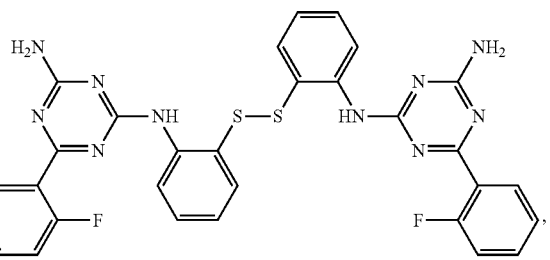
Molecular Weight: 624.6928
MTF 455
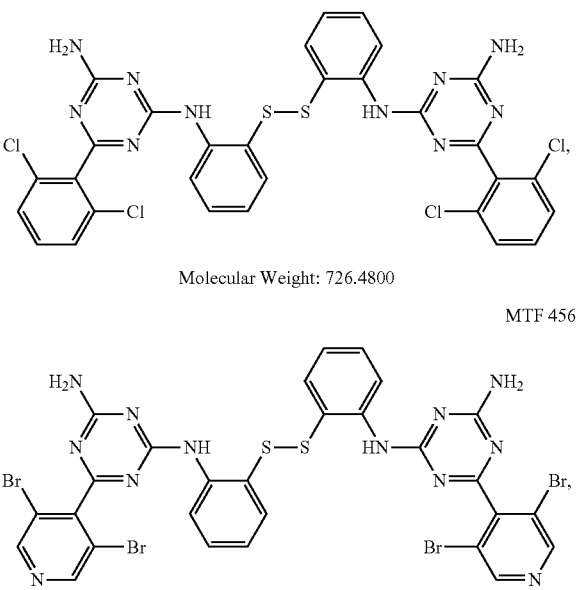
Molecular Weight: 726.4800
MTF 456
Molecular Weight: 906.2720
MTF 458
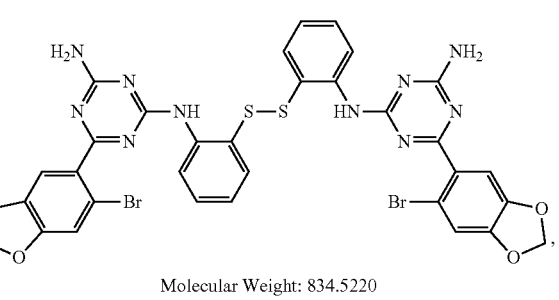
Molecular Weight: 834.5220

MTF 460
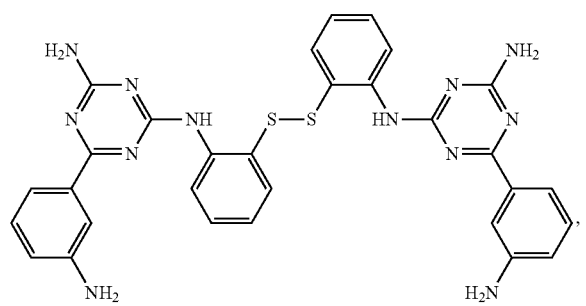
Molecular Weight: 618.7420
MTF 462
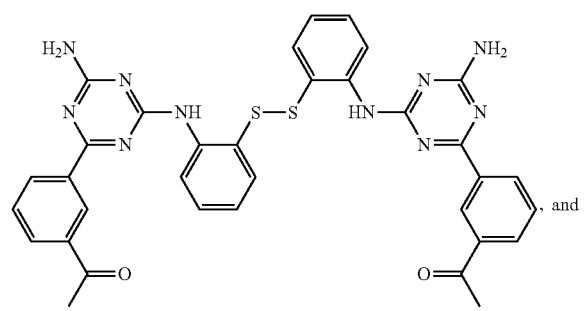
Molecular Weight: 672.7860
MTF 463
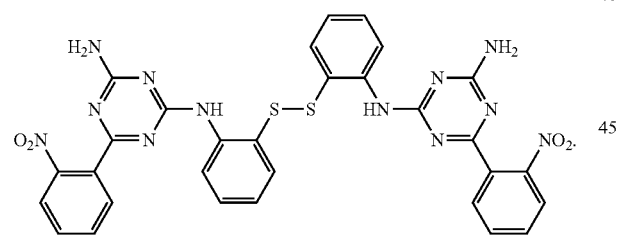
Molecular Weight: 678.7060
In another embodiment, the disclosure provides a compound of formula (III) selected from
CRO 15
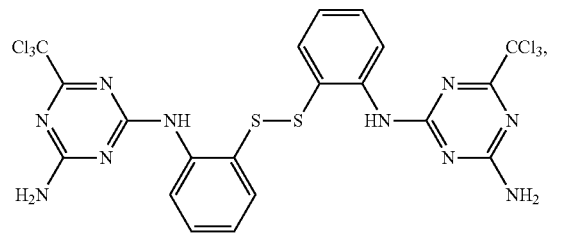
MTF 232
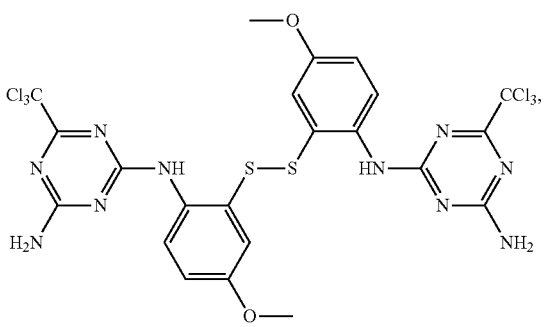
MTF 233
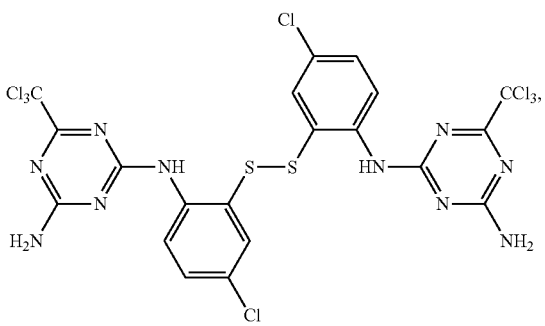
MTF 234
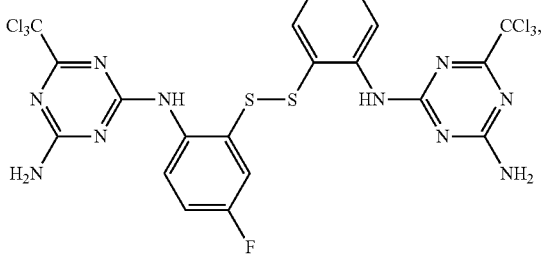
MTF 318
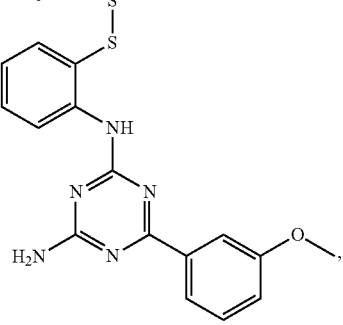

MTF 319
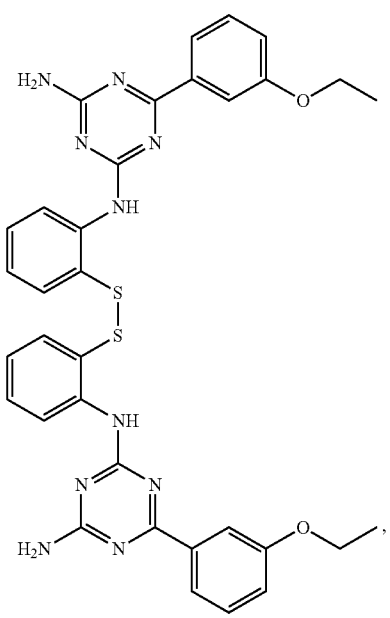
MTF 321
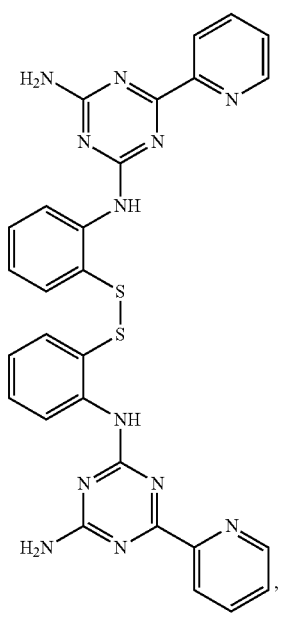
MTF 320
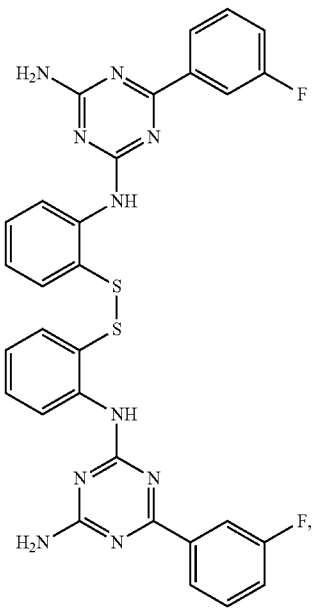
MTF 322
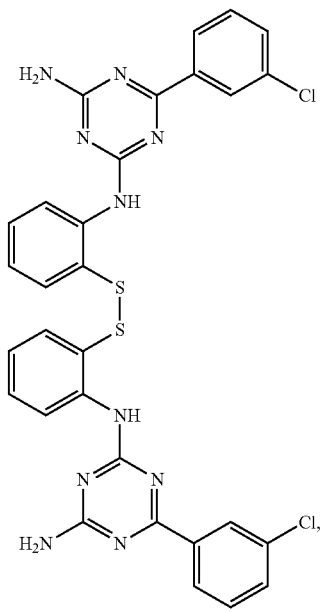

-continued
MTF 323
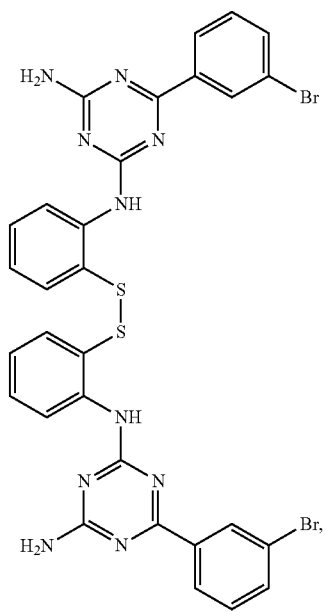
MTF 324
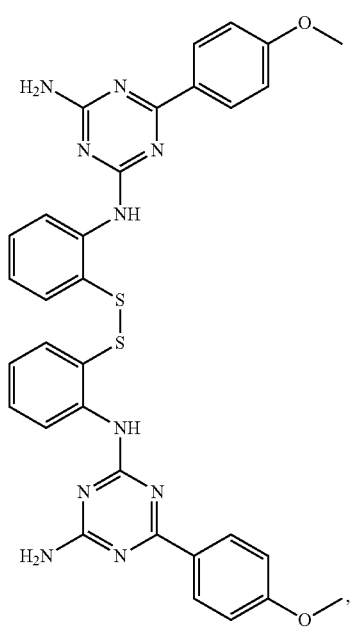
-continued
MTF 325
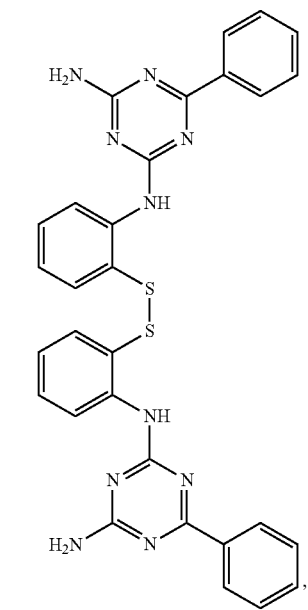
MTF 326

MTF 327
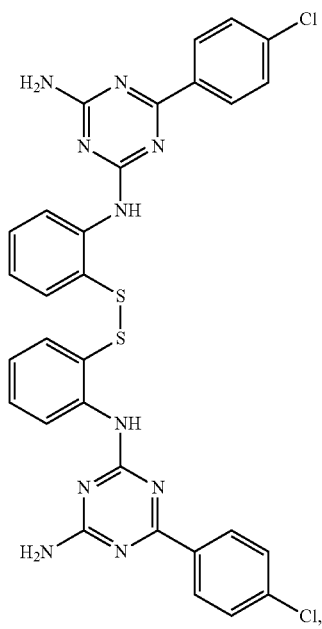
MTF 329
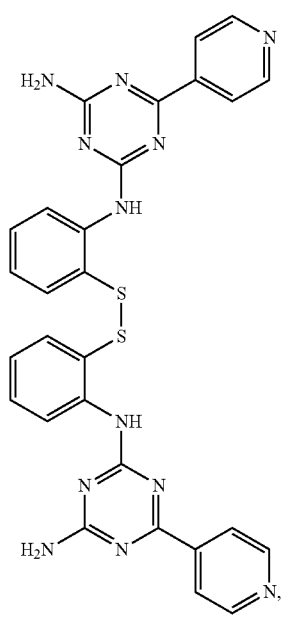
MTF 328
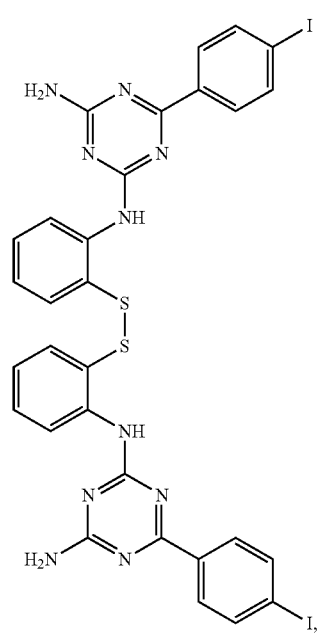
MTF 333
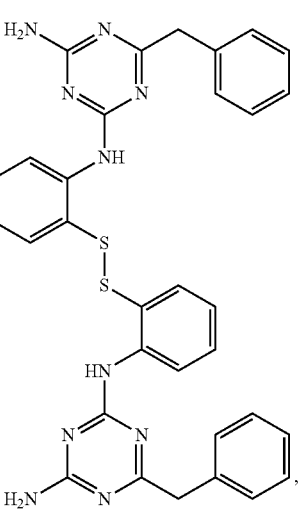

MTF 394
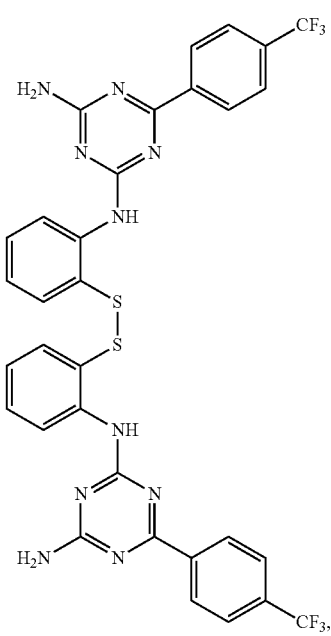
MTF 397
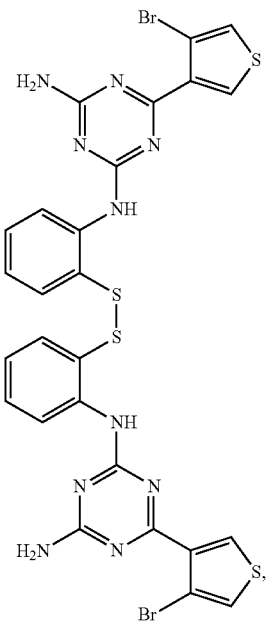
MTF 443
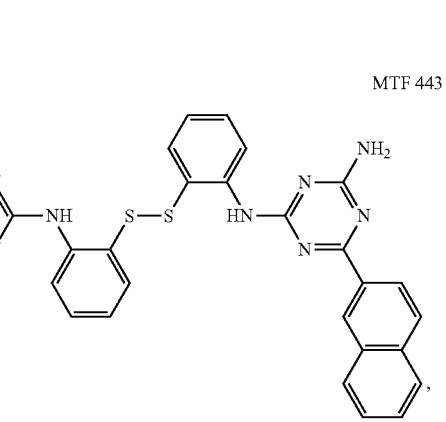
Molecular Weight: 688,8320
MTF 396
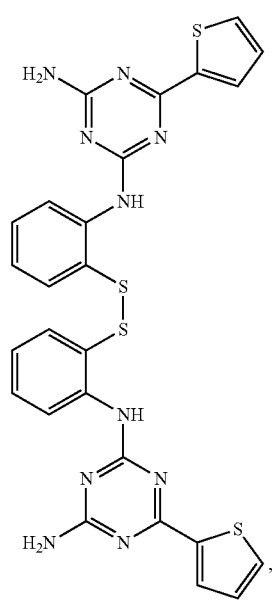
MTF 445
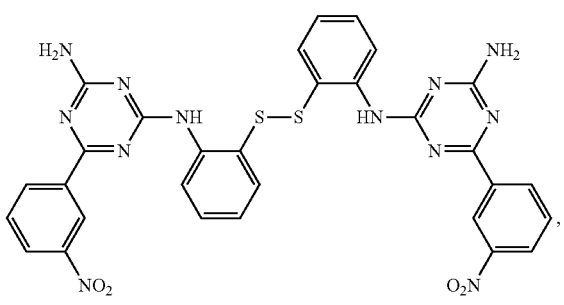
Molecular Weight: 678,7060

MTF 446
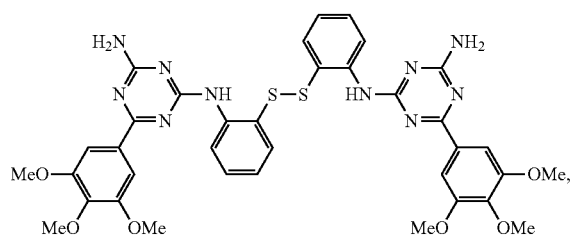
Molecular Weight: 768,8680
MTF 449
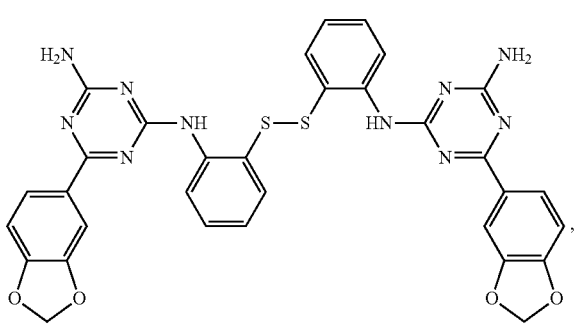
Molecular Weight: 676,7300
MTF 450
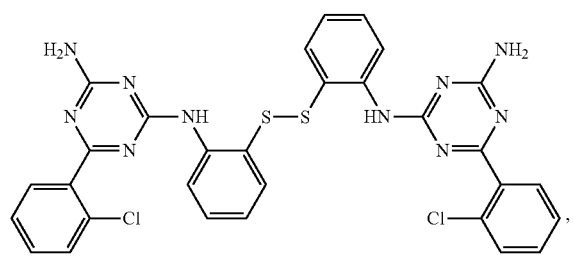
Molecular Weight: 657,5960
MTF 451
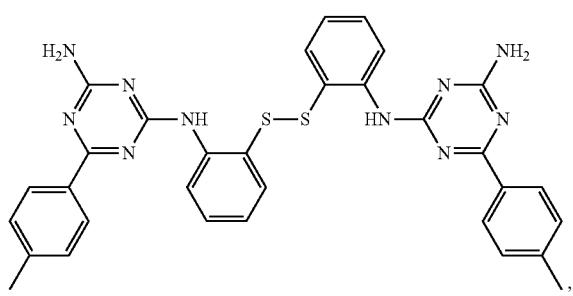
Molecular Weight: 616,7660
MTF 452
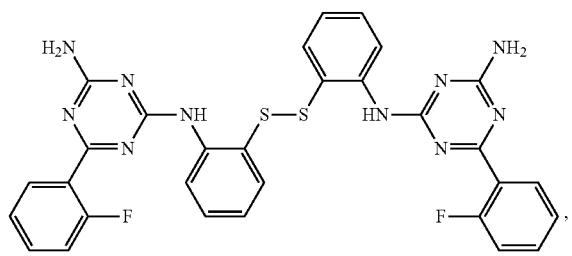
Molecular Weight: 624,6928
MTF 456
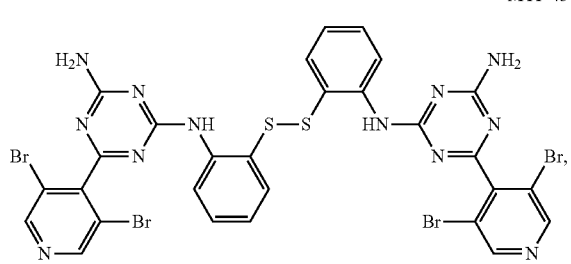
Molecular Weight: 906,2720
MTF 460
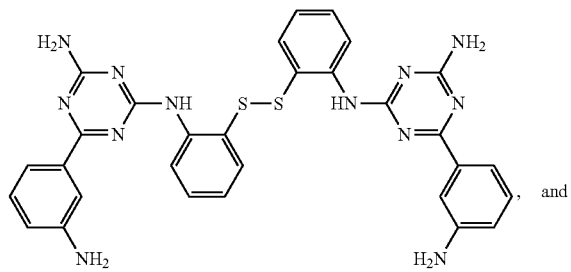
Molecular Weight: 618,7420
MTF 463
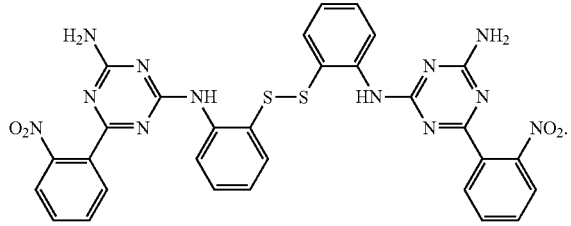
Molecular Weight: 678,7060
In a preferred embodiment, the disclosure provides a compound of formula (III) selected from CRO15
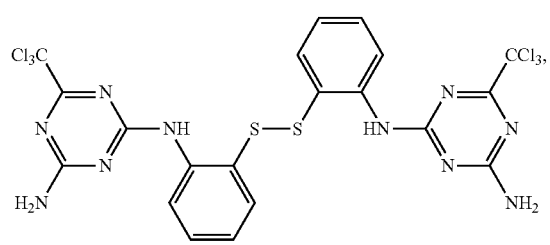
MTF 233
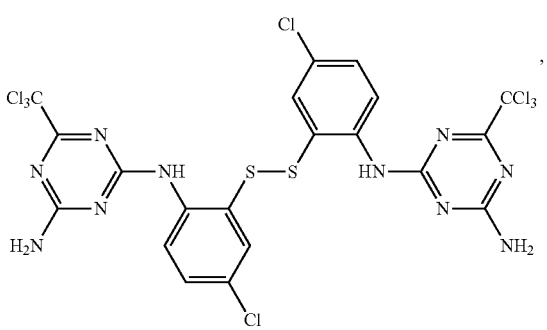
MTF 319
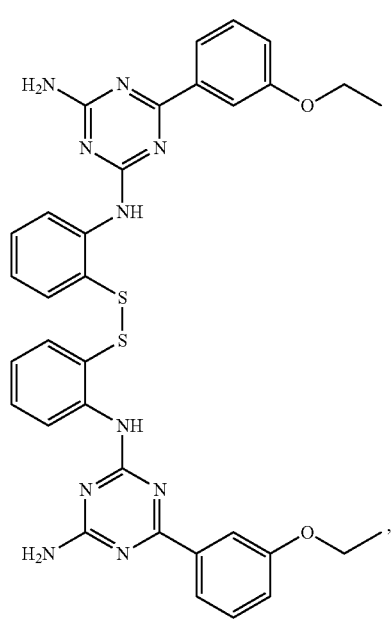
MTF 320
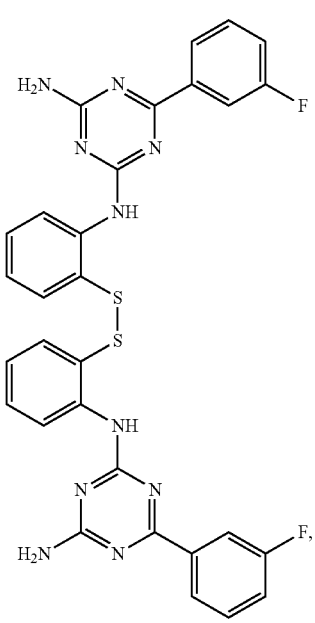
MTF 322
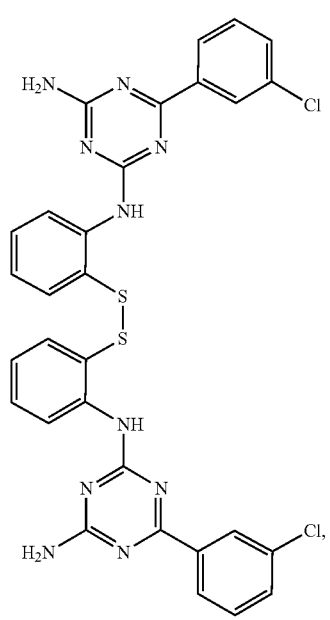
MTF 328
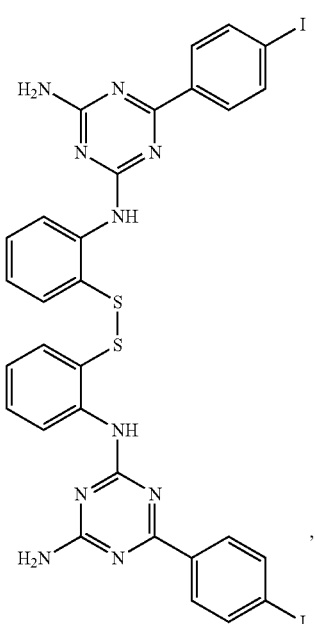

-continued

MTF 394

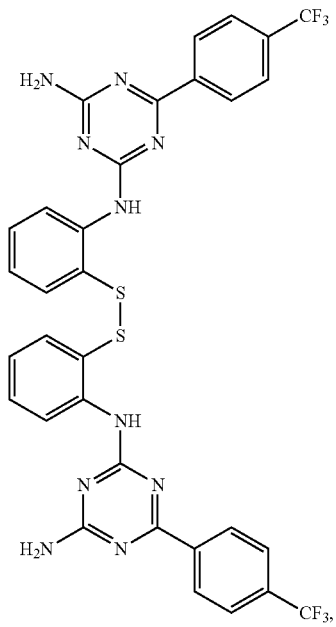

MTF 396

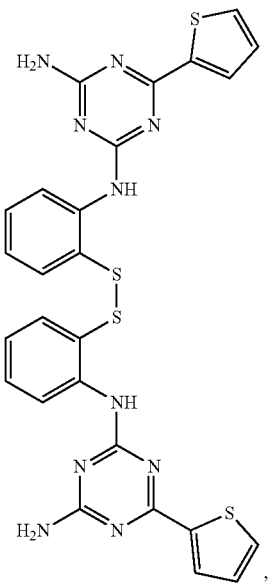

MTF 443

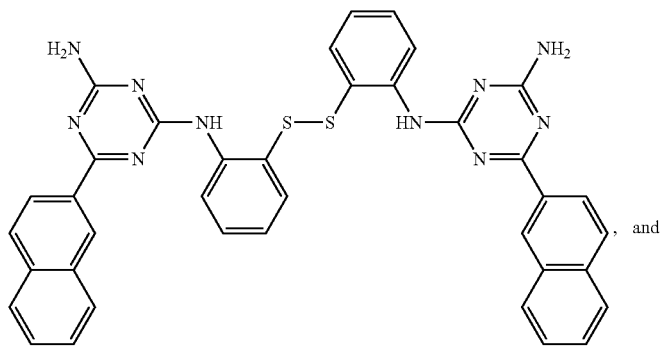

Molecular Weight: 688.8320

MTF 446

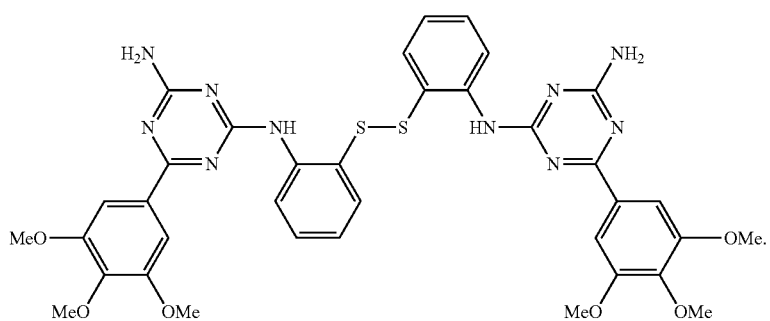

Molecular Weight: 768.8680

In compounds of formula (II), the hydroxyl or thiol function can be protected with a protecting group. As used herein, protecting groups refers to any group cleavable in biological medium, particularly by hydrolysis or removal via the plasmatic enzymes or bioorganic nucleophiles such as glutathione. Suitable protecting group for hydroxyl include [but are not limited to esters, alkyl, alkenyl and alkynyl ethers, silylated ethers, alkoxymethyl ethers, benzyl ethers, tetrahydropyranyl ethers, pentoses, hexoses. Suitable protecting group for thiol group include [but are not limited to any group linked by a disulfide function, thioesters, alkyl, alkenyl and alkynyl thioethers, benzyl thioethers, alkylarylmethyl thioethers, triarylmethylthioethers.

Compounds of formula (II) or (III) as described herein have a high biological activity towards melanoma, including melanomas resistant to BRAF inhibitors. They can therefore be used in a method for treating cancer, and melanoma in particular.

Without being bound to this theory, the inventors hypothesized that compounds of formula (II) and (III) are prodrugs of compounds of formula (I). After administration to a subject, the compounds of formula (II) and (III) are modified through in vivo physiological action, into a compound of formula (I).

Pharmaceutical Composition

The disclosure also relates to a pharmaceutical composition comprising a compound of formula (I), (II) or (III), and a pharmaceutically acceptable carrier.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the disclosure can be formulated for a topical, oral, intranasal, intraocular, intravenous, intramuscular or subcutaneous administration and the like.

The pharmaceutical compositions can take the form of tablets, pills, capsules, semisolids, powders, sustained release formulations, solutions, suspensions, emulsions, syrups, elixirs, aerosols, or any other appropriate compositions; and comprise at least one compound according this disclosure.

Because of their ease in administration, tablets and capsules represent the most advantageous oral dosage unit form, in which case solid pharmaceutical carriers are obviously employed. If desired, tablets may be sugar coated or enteric coated by standard techniques. The tablets or pills can be coated to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The compound of the disclosure and the further agent may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

For aerosol administration, the compound of the disclosure and the further agent are preferably supplied in finely divided from along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., J Mol Neurosci. 19(1-2):167-70 (2002)).

Suitable compositions for topical application include aqueous solutions, suspensions, ointments, creams, gels or sprayable formulations, e.g. aerosol administration.

The doses used for the administration can be adapted as a function of various parameters, and in particular as a function of the mode of administration used, of the relevant pathology, or alternatively of the desired duration of treatment. It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments described herein. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

According to an embodiment, the pharmaceutical composition comprises a non-ionic emulsifier, preferably Kolliphor EL. The presence of such non-ionic emulsifier allows diminishing the final concentration of DMSO in the composition. The compound of formula (I), (II) or (III) can be solubilized in a non-ionic emulsifier, like Kolliphor EL.

Method of Use

The compounds of formula (I), (II) or (III) exhibit valuable pharmaceutical properties as indicated in the in vitro and in vivo tests provided in the examples and are therefore indicated for therapy.

The disclosure also relates to a compound of formula (I), (II) or (III) for use as a medicament.

The disclosure also relates to a compound of formula (I), (II) or (III) for use in a method for treating cancer.

As used herein, the term "cancer" has its general meaning in the art and includes an abnormal state or condition characterized by rapidly proliferating cell growth. The term is meant to include all types of cancerous growths or oncogenic processes, metastatic tissues or malignantly transformed cells, tissues or organs, irrespective of histopathologic type or stage of invasiveness. The term cancer includes malignancies of the various organ systems, such as affecting skin, lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the oesophages.

Examples of cancer include, but are not limited, to hematological malignancies such as B-cell lymphoid neoplasm, T-cell lymphoid neoplasm, non-hodgkin lymphoma (NHL), B-NHL, T-NHL, chronic lymphocytic leukemia (CLL), small lymphocytic lymphoma (SLL), mantle cell lymphoma (MCL), NK-cell lymphoid neoplasm, and myeloid cell lineage neoplasm. Examples of non-hematological cancers include, but are not limited to, skin cancer, colon cancer, breast cancer, lung cancer, brain cancer, prostate cancer, head and neck cancer, pancreatic cancer, bladder cancer, colorectal cancer, bone cancer, cervical cancer, liver cancer, oral cancer, esophageal cancer, thyroid cancer, kidney cancer, stomach cancer and testicular cancer.

In specific embodiment, the disclosure relates to a compound of formula (I), (II) or (III) for use in a method for treating melanoma. In one particular embodiment, the disclosure also relates to a compound of formula (I), (II) or (III) for use in a method for treating BRAF inhibitor-resistant melanoma.

In a specific embodiment, compounds of formula (I), (II) or (III) induce the activation of AMPK. Metformin, a drug normally used to treat type II diabetes, also induces the activation of AMPK and it has been shown that metformin also inhibit the growth of melanoma cells. Therefore, by analogy with metformin, in one particular embodiment, the disclosure also relates to a compound of formula (I), (II) or (III) for use in a method for treating type II diabetes.

The disclosure relates to a method for treating cancer, said method comprising administering to a subject a therapeutically efficient amount of
(i) a compound of formula (I),
(ii) a compound of formula (II) or (III), or
(iii) a pharmaceutical composition as described herein.

The terms "therapeutically efficient amount" of a compound refer to an amount of the compound that will elicit the biological or medical response of a subject, for example, ameliorate the symptoms, alleviate conditions, slow or delay disease progression, or prevent a disease.

The disclosure also relates to the use of a compound of formula (I), (II) or (III), for the manufacture of a medicament for the treatment of cancer. In one embodiment, cancer is melanoma. In one embodiment, cancer is BRAF inhibitor-resistant melanoma.

FIGURES LEGENDS

In all the figures, the bars indicate the mean± SEM: *p<0.05; p<0.01; *p<0.001.

Figure 1A:
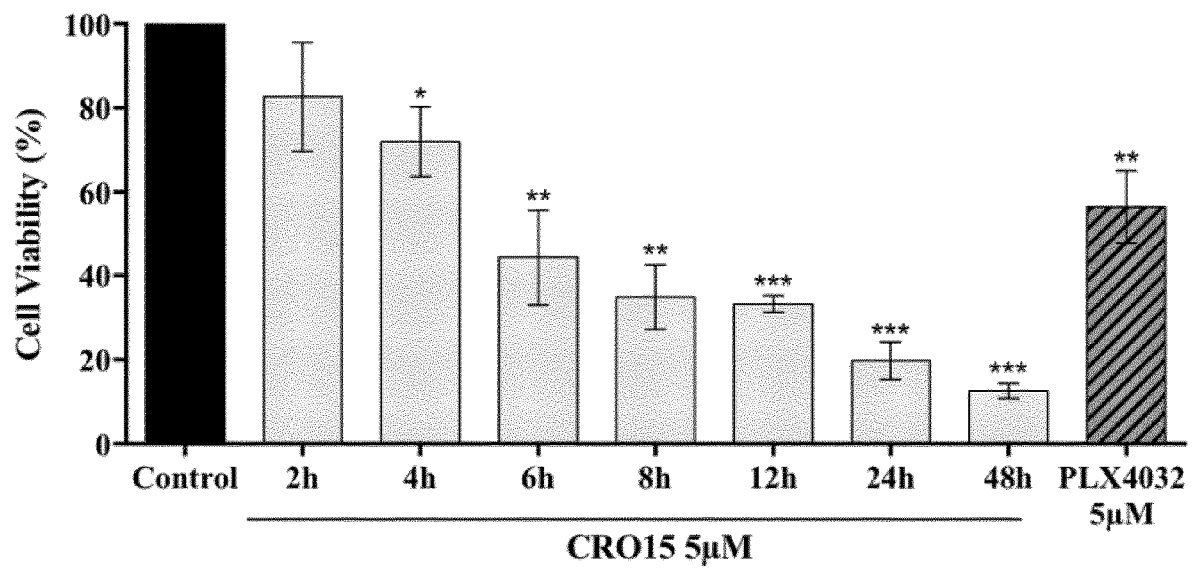
FIG. 1A represents the cell viability of A375 S cells treated with 5 µM of CRO15 or PLX4032 at time indicated on the graph.
Figure 1B:
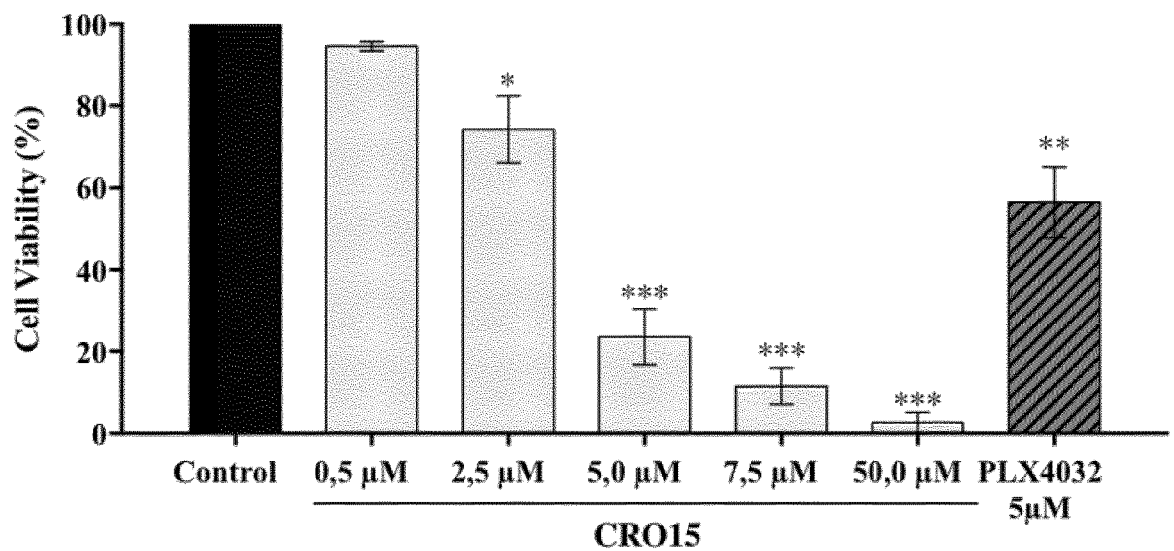
FIG. 1B represents the cell viability of A375 S cells treated with different concentrations of CRO15 or with 5 µM PLX4032 for 48 hours.
Figure 1C:
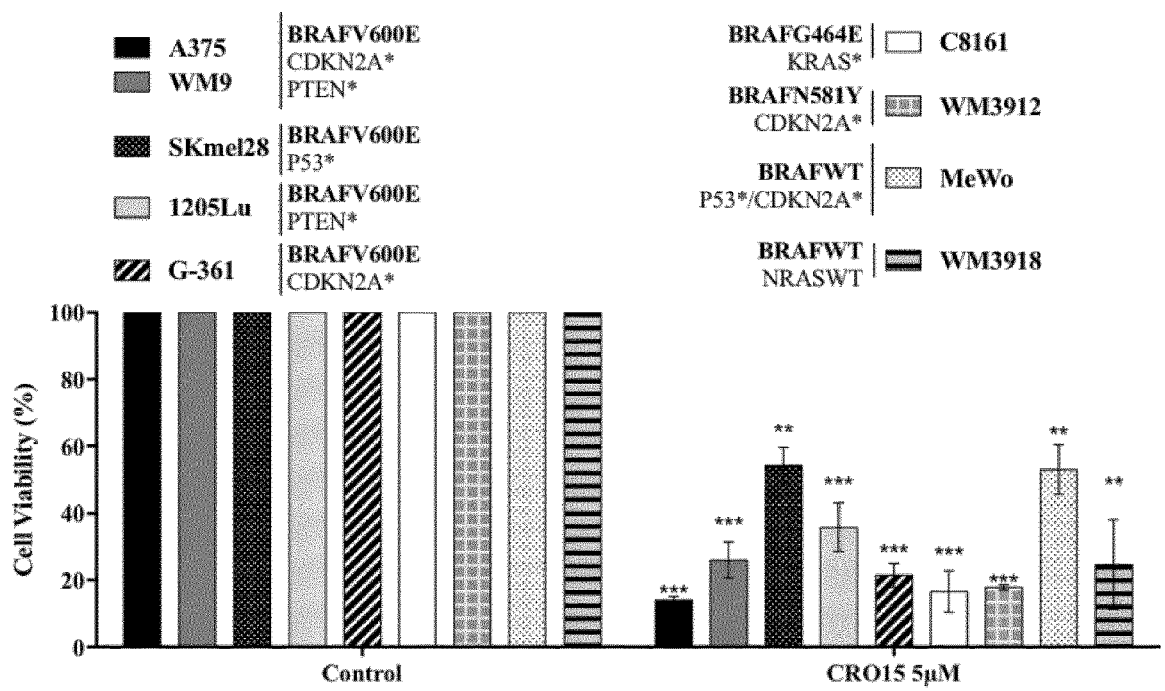

FIG. 1C represents the viability of different melanoma cells with various mutations treated with 5 µM CRO15 for 48 hours. Mutations are specified next to name of melanoma cell lines. Mutated proteins are symbolized with "*".

Figure 1D:
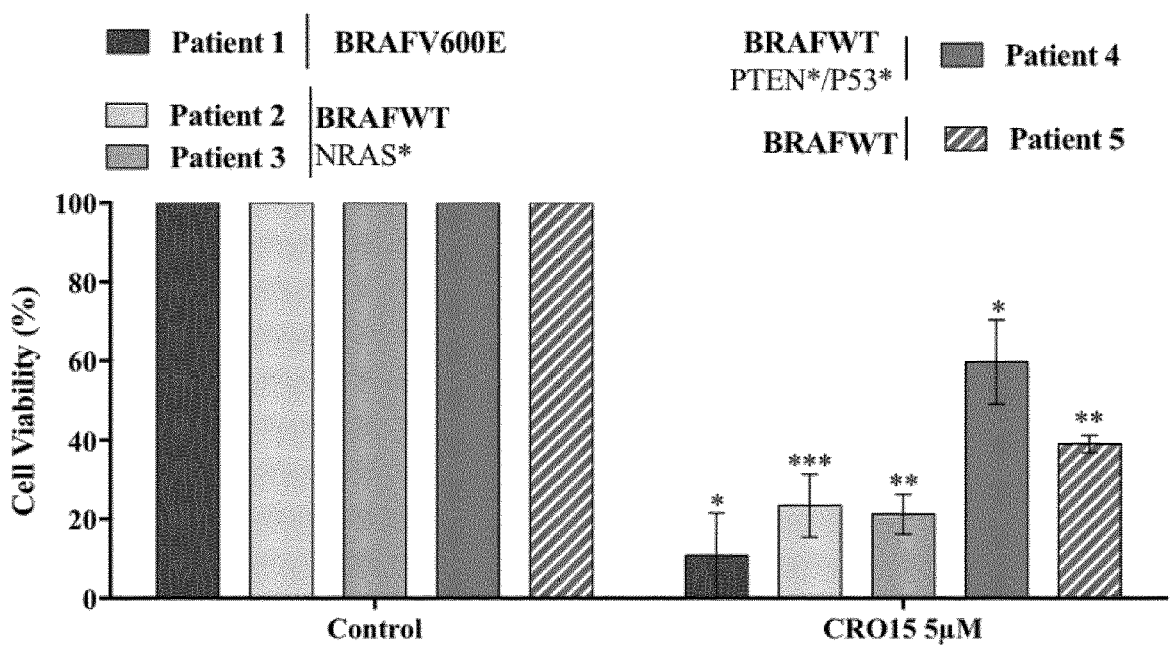

FIG. 1D represents the viability of patient melanoma cells treated with 5 µM CRO15 for 48 hours. Mutated proteins are symbolized with "*"

Figure 1E:
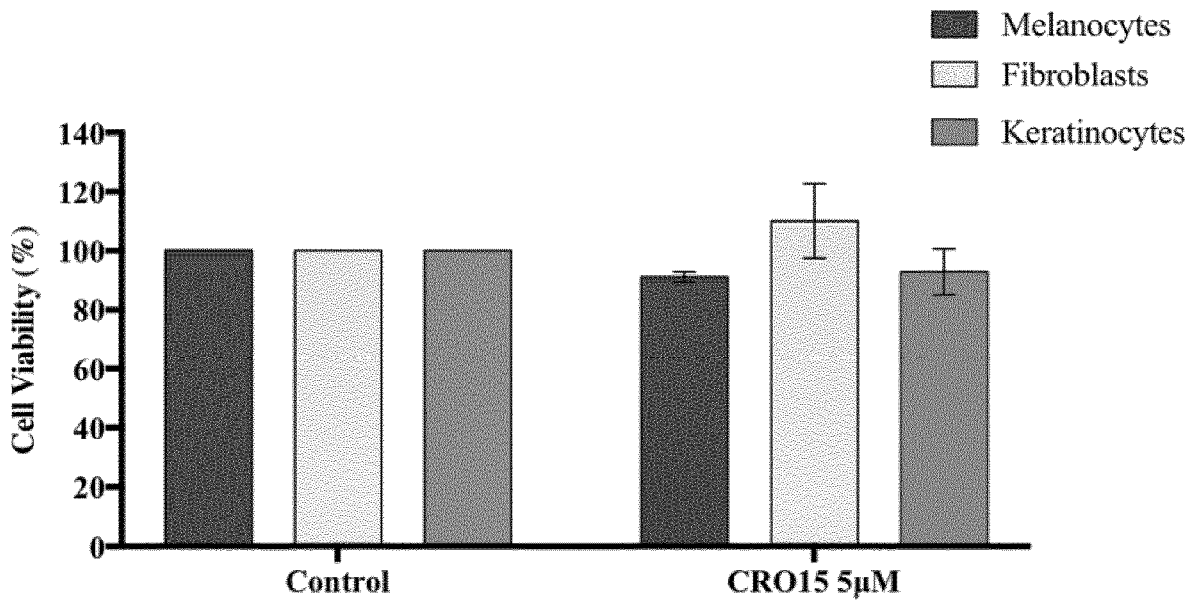

FIG. 1E represents the viability of normal cells treated with 5 µM CRO15 for 48 hours.

Figure 2:
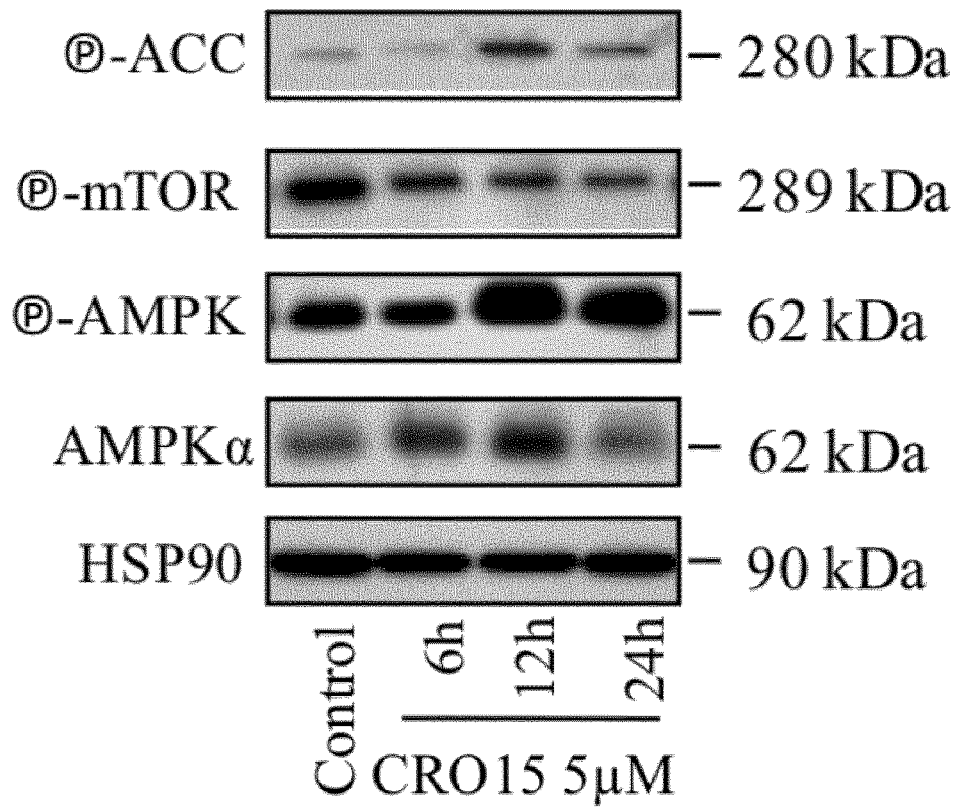

FIG. 2 represents the results of the western blot assays.

Figure 3A:
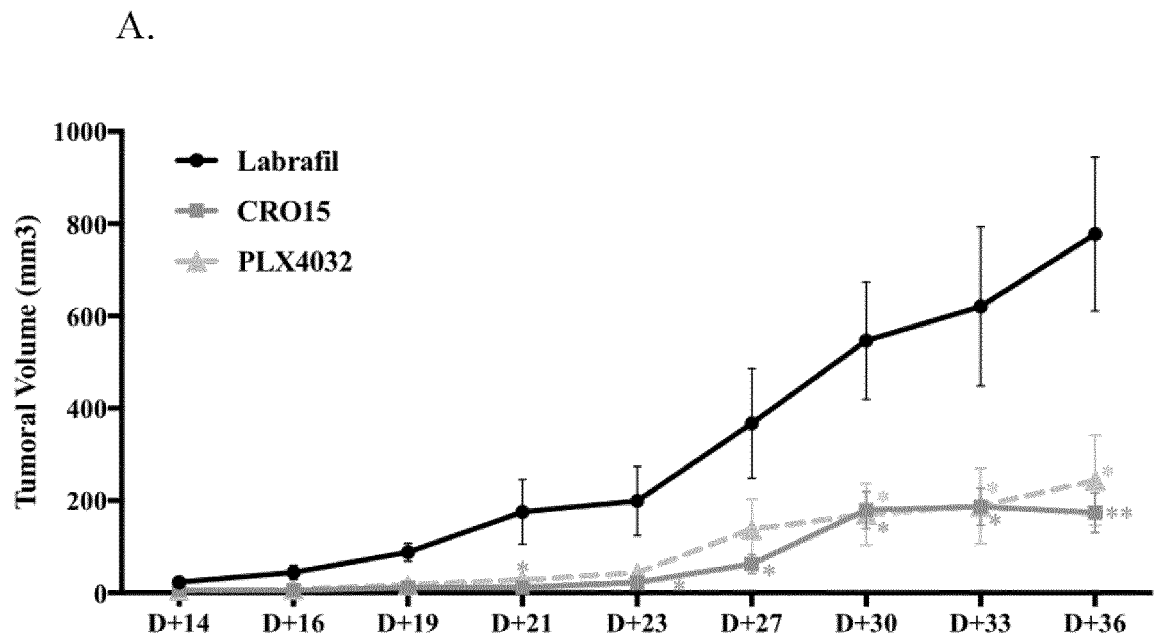

FIG. 3A represents the evolution of the tumoral volume of xenograft mice inoculated subcutaneously with A375 sensitive melanoma cells and treated with CRO15 or PLX4032.

Figure 3B:
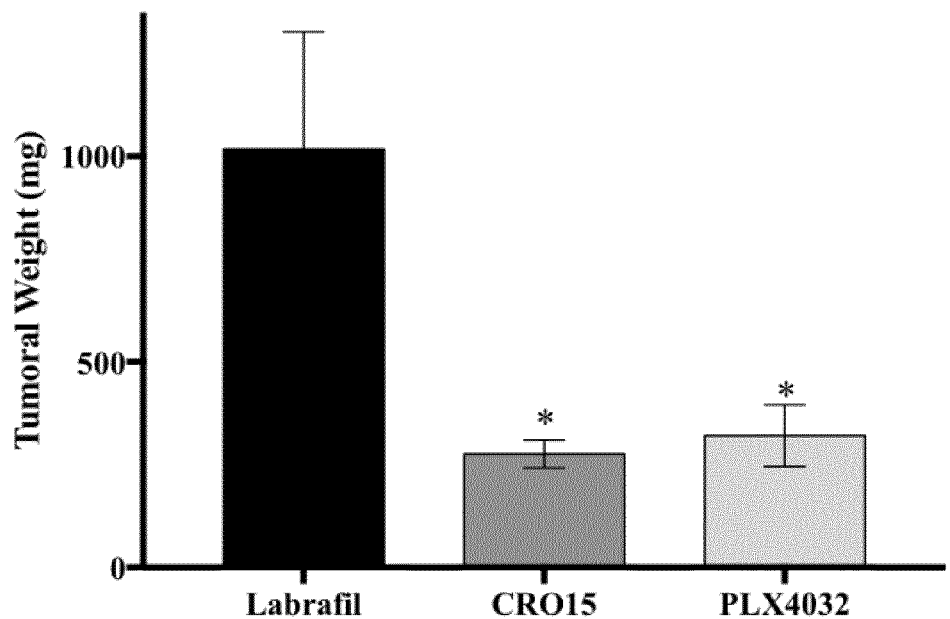

FIG. 3B represents the tumoral weight of xenograft mice inoculated subcutaneously with A375 sensitive melanoma cells and treated with CRO15 or PLX4032, after mice euthanasia.

Figure 4A:
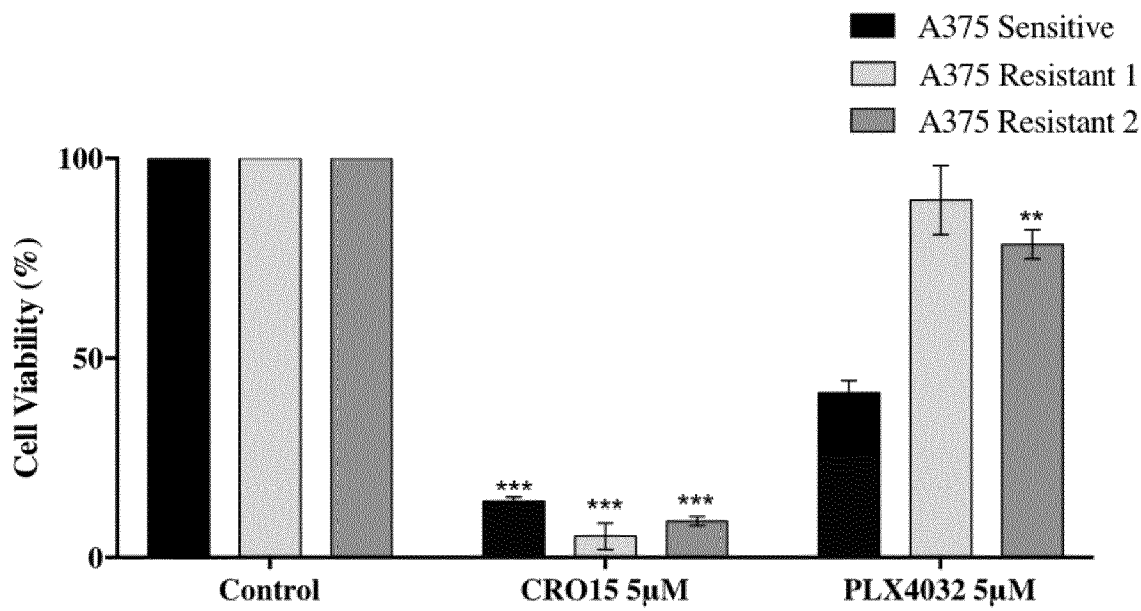

FIG. 4A represents the viability of both sensitive and resistant A375 melanoma cells treated with CRO15 or PLX4032.

Figure 4B:
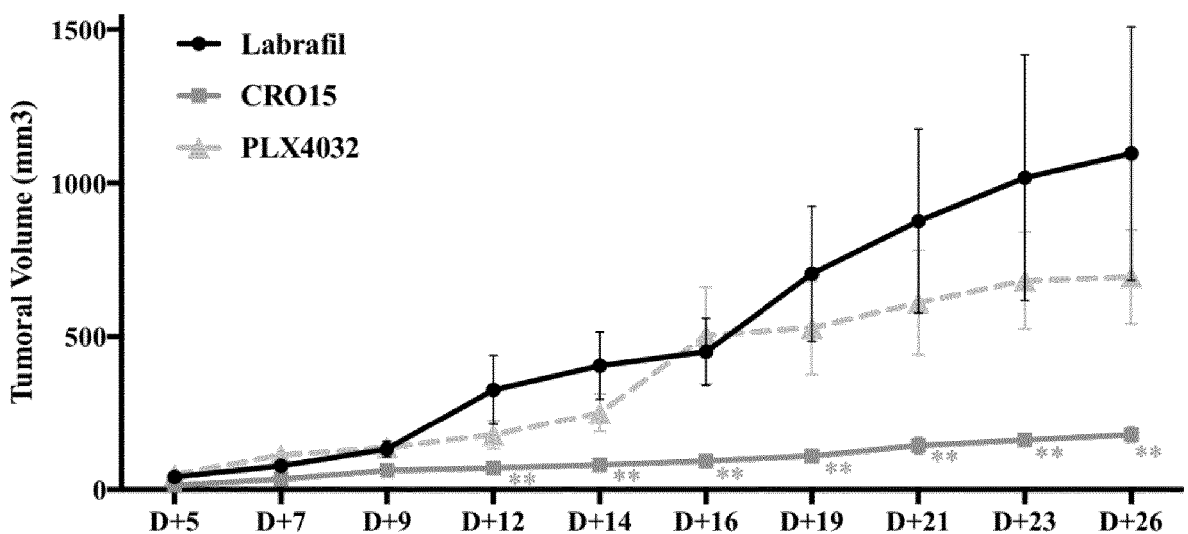

FIG. 4B represents the evolution of the tumoral volume of xenograft mice inoculated subcutaneously with A375 resistant melanoma cells and treated with CRO15 or PLX4032.

Figure 4C:
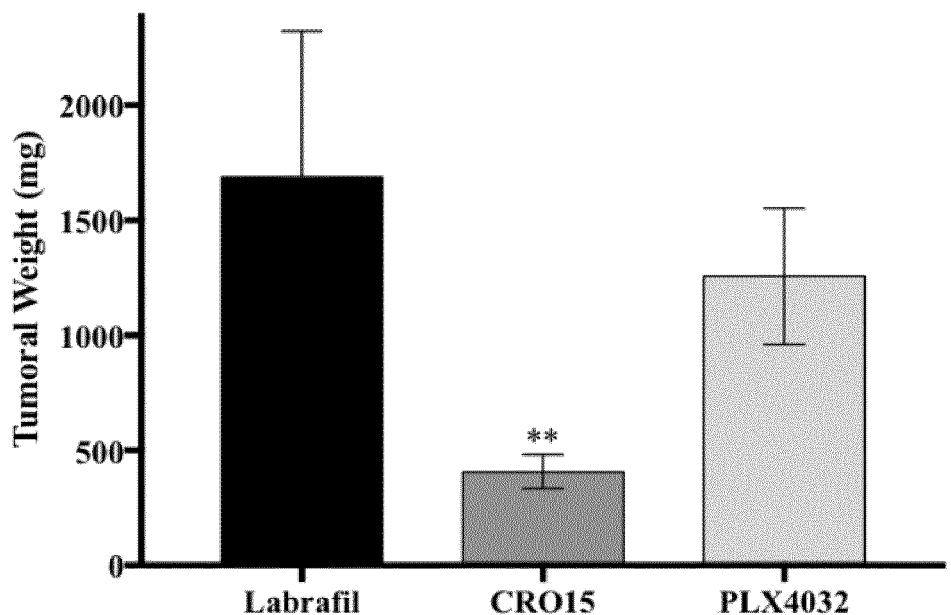

FIG. 4C represents the tumoral weight of xenograft mice inoculated subcutaneously with A375 resistant melanoma cells and treated with CRO15 or PLX4032, after mice euthanasia.

Figure 5:
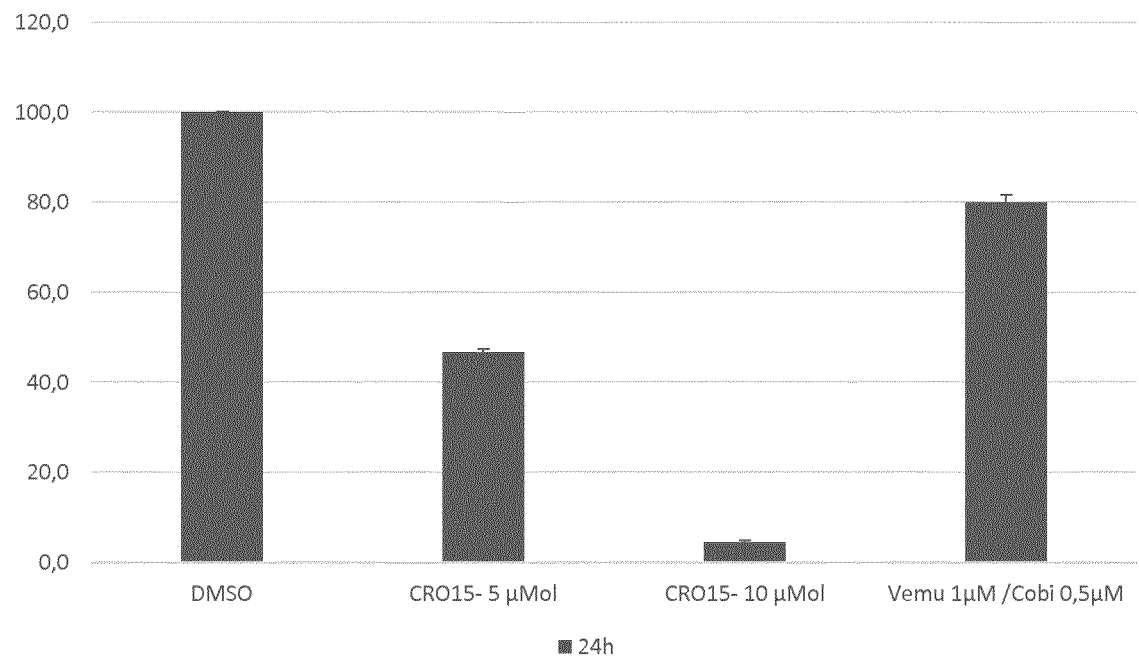

FIG. 5 represents the cell viability of DR6 cells treated with different concentrations of CRO15 or with 1 µM of vemurafenib and 0.5 µM of cobimetinib for 24 hours.

Figure 6A:
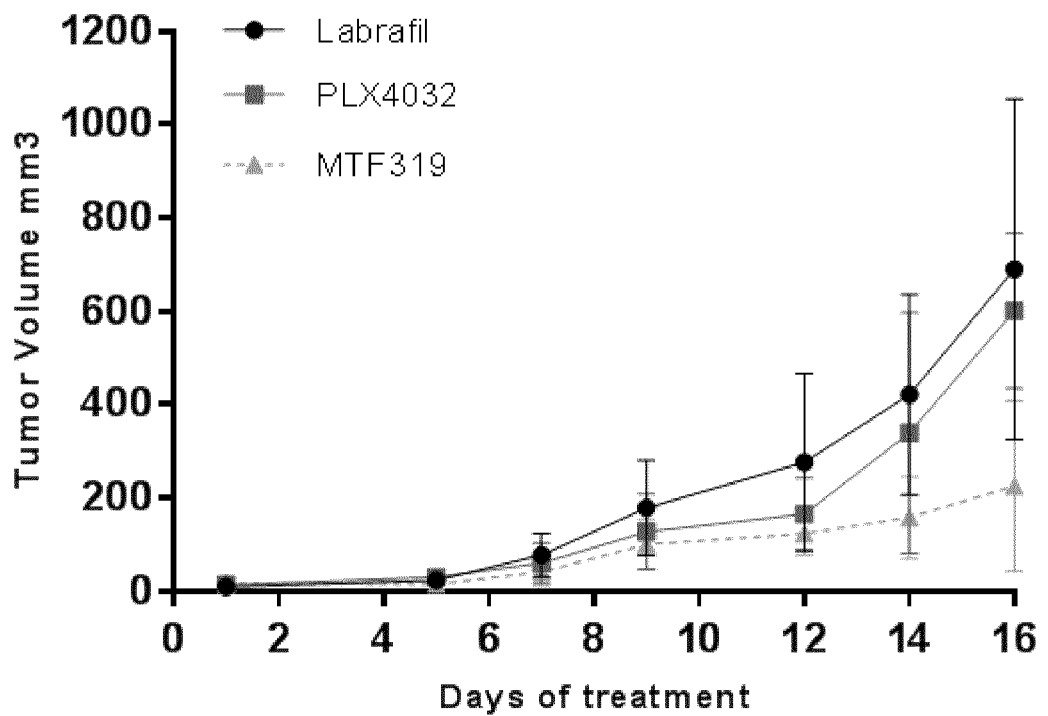

FIG. 6A represents the evolution of the tumoral volume of xenograft mice inoculated subcutaneously with A375 resistant melanoma cells and treated with MTF319 or PLX4032.

Figure 6B:
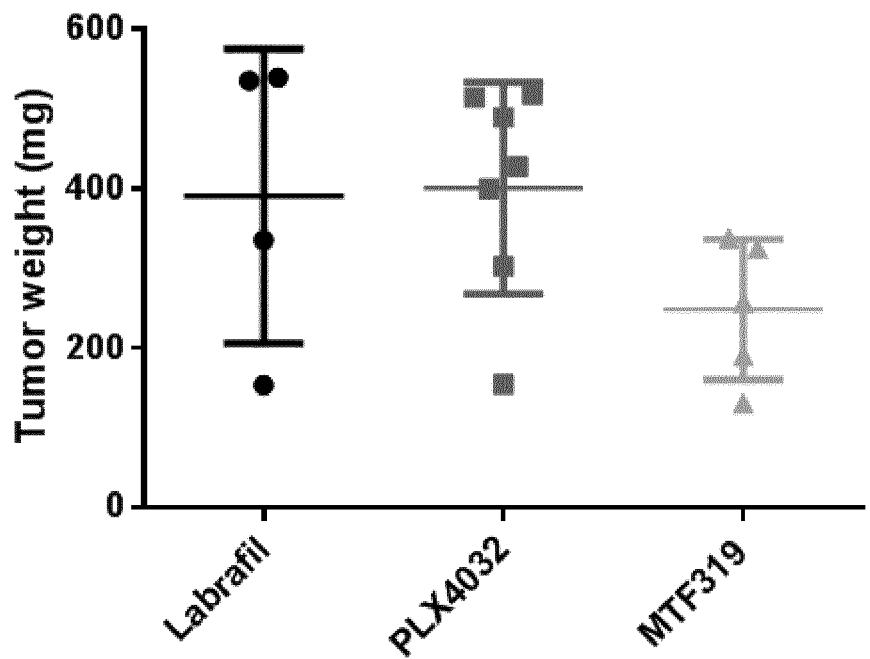

FIG. 6B represents the tumoral weight of xenograft mice inoculated subcutaneously with A375 resistant melanoma cells and treated with MTF319 or PLX4032, after mice euthanasia.

Figure 7A:
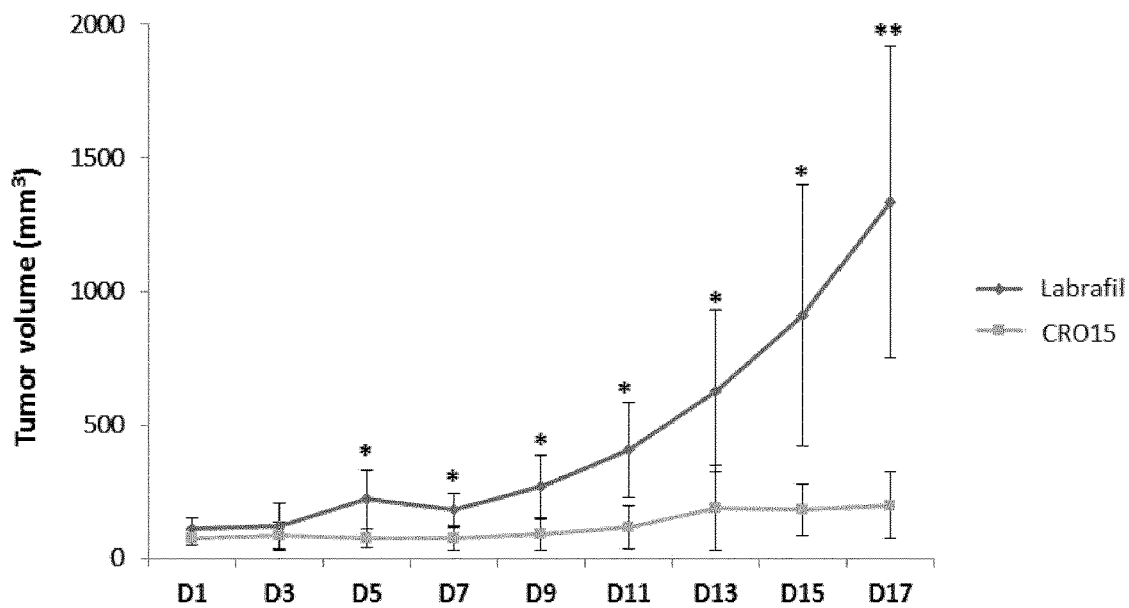

FIG. 7A represents the evolution of the tumoral volume of allograft mice inoculated subcutaneously with murine melanoma cells and treated with CRO15.

Figure 7B:
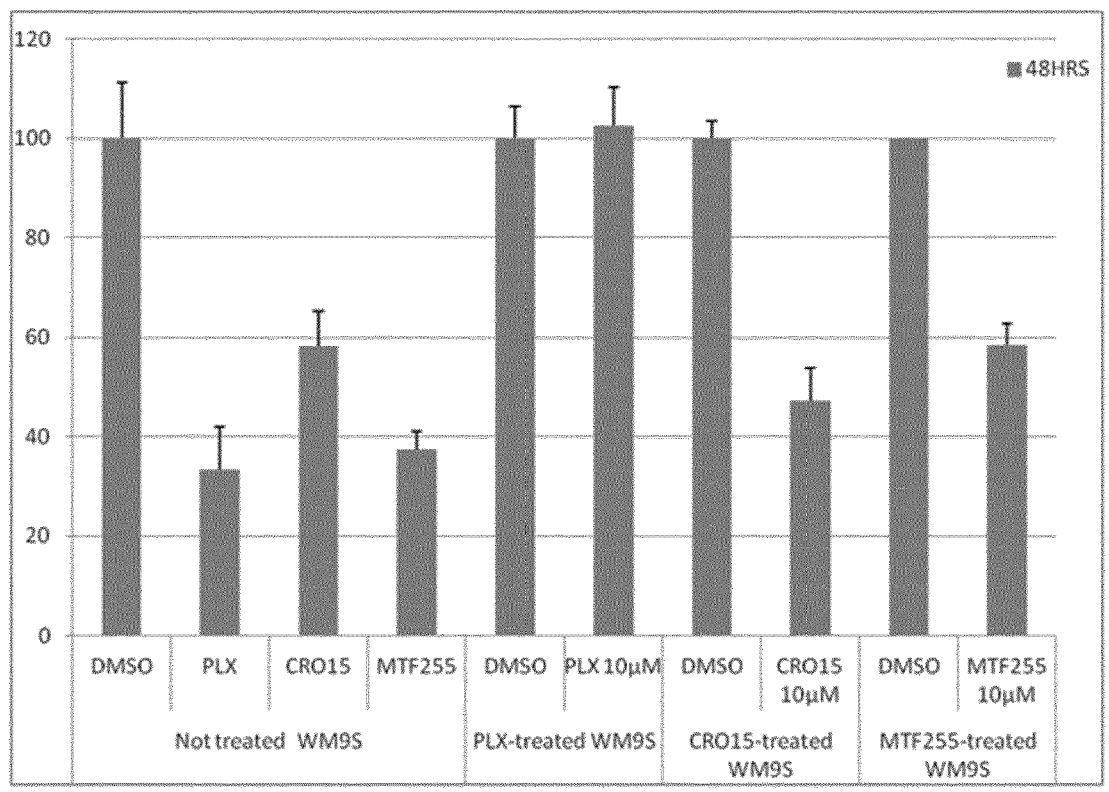

FIG. 7B represents the cell viability of WM9 cells after treatment for 8 weeks with PLX4032, CRO15 or MTF255 and stimulation with 10 µM of each drug for 48 h.

EXAMPLES

Experimental Procedures

Chemical Synthesis and Characterization

Methanol, ethyl acetate, diethyl ether and dichloromethane were purchased from Carlo Erba, and used as received. Anhydrous DMF (99.8% stored under septum) was purchased from Sigma Aldrich, and used as received. All chemicals were purchased from Aldrich, Fisher or Alfa Aesar and used without further purification. Thin layer chromatography (TLC) was performed on precoated Merck 60 GF254 silica gel plates and revealed first by visualization under UV light (254 nm and 360 nm) $^1$H and $^{13}$C NMR spectra were recorded on a Bruker Advance 200 MHz spectrometer or a Bruker Advance 400 MHz or a Bruker Advance 500 MHz. Mass spectra (ESI-MS) were recorded on a Bruker (Daltonics Esquire 3000+). HRMS spectra were recorded on a ThermoFisher Q Exactive (ESI-MS) at a resolution of 140 000 at m/z 200. The purity of compounds was further assayed by HPLC analysis on a JASCO PU-2089 apparatus with Supelco analytical column Ascentis Express C18, 100 mm×46 mm 5 µM. Eluent A: water with 1‰ formic acid. Eluent B: $CH_3CN$ with 1‰ formic acid. Method 1: 30% B for 1 min, 30% B to 100% B over 5 min, 100% B for 2.5 min then from 100% B to 30% B over 30 sec, 30% B for 7 min (16 min in total). Method 2: 30% B for 1 min, 30% B to 100% B over 5 min, 100% B for 20 min then from 100% B to 30% B over 1 min, 30% B for 4 min (31 min in total). Method 3: 30% B for 1 min, 30% B to 100% B over 5 min, 100% B for 2.5 min then from 100% B to 30% B over 30 sec (9 min in total). Method 4: 10% B for 10 min: 10% B to 95% B over 8 min, 95% B for 2 min, then from 95% B to 10% B over 4 min, 10% B for 1 min (25 min in total).

Synthetic Procedures and Characterizations:

General Procedure (A) for the Formation of Biguanides of Formula I

To a solution of the corresponding guanidine (1 equiv) in N,N-dimethylformamide (25 mL/g of guanidine) was added sodium hydride (60% dispersion in mineral oil, 1.5 eq.) and the mixture was stirred for 30 min at r.t. To this solution was added the corresponding nitrile (1 equiv) in one portion. The reaction was stirred overnight at room temperature and monitored by TLC. After completion of the reaction, the mixture was poured into water (200 mL/g of guanidine) and the precipitate was collected and washed with water, methanol and diethyl ether.

General Procedure (B) for the Formation of N2,N2'-(disulfanediylbis(2,1-phenylene))bis(6-aryl/hetaryl-1,3,5-triazine-2,4-diamines) of formula II and III (B)

A solution of the corresponding biguanide (1 equiv) in technical grade ethanol (approx. 25 mL/100 mg of biguanide) was stirred at reflux temperature and monitored by LCMS. After full conversion (approx 6-7 hours), the precipitate formed was filtered and washed with technical grade ethanol.

General Procedure (C) for the formation of N2,N2'-(disulfanediylbis(4-alkyl/hal-2,1-phenylene))bis(6-(trichloromethyl)-1,3,5-triazine-2,4-diamines) of Formula II and III To a solution of the corresponding guanidine (1 equiv) in technical grade ethanol (approx. 10 mL/g of guanidine), trichloroacetonitrile (2 equiv) was added and the reaction mixture was stirred at reflux temperature and monitored by LCMS. After full conversion (approx 6-7 hours), the precipitate formed was filtered and washed with technical grade ethanol and diethyl ether.

General Procedure (D) for the formation of 2-((6-imino-4-(trichloromethyl)-1,6-dihydro-1,3,5-triazin-2-yl)amino)phenols To a solution of corresponding guanidine (1 equiv.) in technical grade ethanol (25 mL/g of guanidine) trichloroacetonitrile (10 equiv.) was added and the reaction mixture was stirred in a sealed tube under argon atmosphere at 60° C. After full conversion (approx. 18 hours), the mixture was concentrated to dryness. The residue was purified by silica gel flash chromatography.

General Procedure (E) for the formation of 2-(4-amino-6-phenyl-1,3,5-triazin-2-yl)amino)phenols To a solution of corresponding guanidine (1 equiv.) in N,N-dimethylformamide (25 mL/g of guanidine) sodium hydride (60% dispersion in mineral oil, 1.1 equiv.) was added and the reaction mixture was stirred in a sealed tube under argon atmosphere. When the gas evolution stopped to this solution was added corresponding nitrile (1 equiv.) and the tube was sealed. The resulting solution was then stirred at 80° C. After full conversion (approx. 18 hours), the mixture was concentrated to dryness. The residue was purified by silica gel flash chromatography.

N2,N2'-(disulfanediylbis(2,1-phenylene))bis(6-(trichloromethyl)-1,3,5-triazine-2,4-diamine) (CRO15)

A solution of 1-(benzo[d]thiazol-2-yl)guanidine (10.0 g, 52 mmol) and trichloroacetonitrile (10.0 mL, 1.92 mmol) in technical grade ethanol (100 mL) was stirred at 75° C. After 1 h, a large amount of white precipitate appeared in the yellow solution. After reaction completion (TLC monitoring, about 3 h), the suspension was cold down to r.t. and filtered. The precipitate was washed with little amount of cold ethanol and dried at air. Recrystallization from acetone/diethyl ether afforded the desired compound as a white solid (10.03 g, 57.5%). TLC: $R_f$ (Et$_2$O/PE, 1/1, v/v)=0.23. $^1$H NMR (200 MHz, Acetone-d6): δ 8.54 (s, 1H), 7.96 (d, J=8.0 Hz, 1H), 7.58 (dd, J=7.8, 1.6 Hz, 1H), 7.35 (td, J=7.8, 1.6 Hz, 1H), 7.22-6.93 (m, 3H). $^{13}$C NMR (101 MHz, Acetone-d6): δ 174.00, 168.98, 166.37, 139.05, 133.76, 130.58, 129.92, 126.33, 125.34, 97.43. HRMS-ESI (m/z): [M+H]$^+$ calc. for $C_{20}H_{15}Cl_6N_{10}S_2^+$, 668.90482; Found: 668.90497. HPLC ($\lambda_{280}$): Purity 97.4%; $t_R$: 7.958 min (method 2).

N2,N2'-(disulfanediylbis(4-methoxy-2,1-phenylene))bis(6-(trichloromethyl)-1,3,5-triazine-2,4-diamine) (MTF-232)

Synthesized following the general procedure C using 1-(6-methoxybenzo[d]thiazol-2-yl)guanidine (300 mg, 1.35 mmol) to afford the titled compound as a green powder (418 mg, 85%). $^1$H NMR (400 MHz, DMSO-d6): δ 9.64 (s, 1H), 7.59 (s, 1H), 7.45 (s, 1H), 7.20 (d, J=8.7 Hz, 1H), 7.10 (s, 1H), 6.84 (dd, J=8.7, 2.8 Hz, 1H), 3.70 (s, 3H). $^{13}$C NMR (50 MHz, DMSO-d6): δ 172.28, 167.38, 166.07, 158.26, 135.44, 129.22, 128.28, 113.08, 112.20, 96.77, 55.48. HPLC ($\lambda_{280}$): Purity 100.0%; $t_R$: 7.433 min (method 3).

N2,N2'-(disulfanediylbis(4-chloro-2,1-phenylene))bis(6-(trichloromethyl)-1,3,5-triazine-2,4-diamine) (MTF-233)

Synthesized following the general procedure C using 1-(6-chlorobenzo[d]thiazol-2-yl)guanidine (300 mg, 1.32 mmol) to afford the titled compound as a white powder (454 mg, 93%). $^1$H NMR (400 MHz, DMSO-d6): δ 9.66 (s, 1H), 7.71 (s, 1H), 7.58 (s, 2H), 7.40 (d, J=8.5 Hz, 1H), 7.35 (dd, J=8.5, 2.3 Hz, 1H). $^{13}$C NMR (50 MHz, DMSO-d6): δ 172.39, 167.34, 165.59, 135.71, 134.89, 131.29, 129.12, 127.91, 127.52, 96.63. HPLC ($\lambda_{280}$): Purity 95.1%; $t_R$: 13.767 min (method 1).

N2,N2'-(disulfanediylbis(4-fluoro-2,1-phenylene))bis(6-(trichloromethyl)-1,3,5-triazine-2,4-diamine) (MTF-234)

Synthesized following the general procedure C using 1-(6-fluorobenzo[d]thiazol-2-yl)guanidine (300 mg, 1.42 mmol) to afford the titled compound as a white powder (457 mg, 91%). $^1$H NMR (200 MHz, DMSO-d6): δ 9.06 (br. s., 2H), 7.69 (br. s., 1H), 7.57 (br. s., 1H), 7.45-7.30 (m, 2H), 7.14 (t, 1H, J=8.6 Hz, H1). $^{13}$C NMR (50 MHz, DMSO-d6): δ 172.42, 167.38, 165.94, 160.87 (d), 136.40, 131.93, 130.04, 114.76 (d), 113.61 (d), 96.69. HPLC ($\lambda_{280}$): Purity 98.7%; $t_R$: 6.858 min (method 3).

N—(N-(benzo[d]thiazol-2-yl)carbamimidoyl)-3-bromobenzimidamide (MTF-242)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-bromobenzonitrile (0.95 g, 5.20 mmol) to afford the titled compound as a white-yellowish powder (708 mg, 36%). $^1$H NMR (500 MHz, DMSO-d6): δ 10.29 (br. s, 1H), 9.36 (br. s, 1H), 8.94 (br. s, 1H), 8.26 (s, 1H), 8.11 (s, 1H), 8.03 (d, J=7.9 Hz, 1H), 7.80 (d, J=7.7 Hz, 1H), 7.76 (dd, J=7.9, 1.1 Hz, 1H), 7.66 (d, J=8.0 Hz, 1H), 7.47 (t, J=7.9 Hz, 1H), 7.39-7.30 (m, 1H), 7.24-7.15 (m, 1H). $^{13}$C NMR (50 MHz, DMSO-d6): δ 172.23, 161.94, 160.52, 151.47, 137.42, 134.08, 131.23, 130.43, 126.51, 125.66, 122.86, 121.70, 121.15, 119.78. HRMS-ESI (m/z): [M+H]$^+$ calc. for $C_{15}H_{12}BrN_5S^+$, 374.00696; Found: 374.00797. HPLC ($\lambda_{280}$): Purity 99.3%; $t_R$: 6.775 min (method 1).

N—(N-(benzo[d]thiazol-2-yl)carbamimidoyl)-3-chlorobenzimidamide (MTF-243)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-chlorobenzonitrile (715 mg, 5.20 mmol) to afford the titled compound as a yellow powder (206 mg, 12%). $^1$H NMR (500 MHz, DMSO-d6): δ 10.30 (br. s, 1H), 9.37 (br. s, 1H), 8.90 (br. s, 1H), 8.12 (t, br. s, J=1.8 Hz, 2H), 7.99 (d, J=7.9 Hz, 1H), 7.80 (d, J=7.7 Hz, 1H), 7.66 (d, J=7.9 Hz, 1H), 7.65-7.60 (m, 1H), 7.54 (t, J=7.9 Hz, 1H), 7.38-7.30 (m, 1H), 7.22-7.17 (m, 1H). $^{13}$C NMR (50 MHz, DMSO-d6): δ 172.22, 161.95, 160.57, 151.47, 137.26, 133.22, 131.23, 131.20, 130.20, 127.53, 126.14, 125.67, 122.87, 121.16, 119.79. HRMS-ESI (m/z): [M+H]$^+$ calc. for $C_{15}H_{12}ClN_5S^+$, 330,05747; Found: 330, 05774. HPLC ($\lambda_{280}$): Purity 99.2%; $t_R$: 6.792 min (method 1).

N—(N-(benzo[d]thiazol-2-yl)carbamimidoyl)-2-chlorobenzimidamide (MTF-244)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2-chlorobenzonitrile (715 mg, 5.20 mmol) to afford the titled compound as a white powder (326 mg, 19%). $^1$H NMR (500 MHz, DMSO-d6): δ 10.14 (br. s, 1H), 9.30 (br. s, 1H), 8.81 (br. s, 1H), 8.09 (br. s, 1H), 7.80 (d, J=7.5 Hz, 1H), 7.65 (d, J=7.7 Hz, 1H), 7.53 (br. s, 2H), 7.50-7.40 (m, 2H), 7.34 (t, J=7.1 Hz, 1H), 7.20 (t, J=7.1 Hz, 1H). $^{13}$C NMR (50 MHz, DMSO-d6): δ 172.40, 162.90, 162.00, 151.45, 136.67, 131.23, 130.66, 130.29, 129.56, 129.46, 126.97, 125.63, 122.82, 121.16, 119.74. HRMS-ESI (m/z): [M+H]$^+$ calc. for $C_{15}H_{12}CN_5S^+$, 330.05747; Found: 330.05783. HPLC ($\lambda_{280}$): Purity 96.6%; $t_R$: 6.500 min (method 1).

N—(N-(benzo[d]thiazol-2-yl)carbamimidoyl)-4-chlorobenzimidamide (MTF-245)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-chlorobenzonitrile (715 mg, 5.20 mmol) to afford the titled compound as a white-yellowish powder (721 mg, 42%). $^1$H NMR (500 MHz, DMSO-d6): δ 10.27 (br. s, 1H), 9.36 (br. s, 1H), 8.85 (br. s, 1H), 8.06 (d, br.s, J=8.6 Hz, 3H), 7.79 (d, J=7.4 Hz, 1H), 7.66 (d, J=7.9 Hz, 1H), 7.59 (d, J=8.6 Hz, 2H), 7.34 (t, J=7.7 Hz, 1H), 7.19 (t, J=7.6 Hz, 1H). $^{13}$C NMR (50 MHz, DMSO-d6): δ 172.22, 162.00, 160.95, 151.47, 136.28, 134.00, 131.21, 129.44, 128.36, 125.65, 122.83, 121.15, 119.74. HRMS-ESI (m/z): [M+H]$^+$ calc. for $C_{15}H_{12}ClN_5S^+$, 330.05747; Found: 330.05743. HPLC ($\lambda_{280}$): Purity 98.8%; $t_R$: 6.800 min (method 1).

N—(N-(benzo[d]thiazol-2-yl)carbamimidoyl)-4-methylbenzimidamide (MTF-246)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and p-tolunitrile (609 mg, 5.20 mmol) to afford the titled compound as a beige powder (145 mg, 9%). $^1$H NMR (500 MHz, DMSO-d6): δ 10.28 (br. s, 1H), 9.34 (br. s, 1H), 8.74 (br. s, 1H), 7.96 (d, br. s, J=7.9 Hz, 3H), 7.79 (d, J=7.7 Hz, 1H), 7.65 (d, J=7.9 Hz, 1H), 7.33 (dd, J=18.6, 7.7 Hz, 3H), 7.19 (t, J=7.5 Hz, 1H), 2.37 (s, 3H). $^{13}$C NMR (50 MHz, DMSO-d6): δ 172.21, 161.99, 161.33, 151.46, 137.15, 134.68, 131.21, 129.49, 125.64, 122.82, 121.13, 119.74, 99.13. HRMS-ESI (m/z): [M+H]$^+$ calc. for $C_{16}H_{15}N_5S^+$, 310.11209; Found: 310.11218. HPLC ($\lambda_{280}$): Purity 97.9%; $t_R$: 6.592 min (method 1).

N—(N-(benzo[d]thiazol-2-yl)carbamimidoyl)-4-iodobenzimidamide (MTF-247)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-iodobenzonitrile (1.19 g, 5.20 mmol) to afford the titled compound as a beige powder (832 mg, 38%). $^1$H NMR (500 MHz, DMSO-d6): δ 10.24 (br. s, 1H), 9.34 (br. s, 1H), 8.82 (br. s, 1H), 8.03 (br. s, 1H), 7.90 (d, J=8.5 Hz, 2H), 7.82 (d, J=8.5 Hz, 2H), 7.79 (d, J=7.8 Hz, 1H), 7.65 (d, J=7.9 Hz, 1H), 7.34 (t, J=7.6 Hz, 1H), 7.19 (t, J=8.0 Hz, 1H). $^{13}$C NMR (126 MHz, DMSO-d6): δ 172.20, 161.97, 161.31, 151.45, 137.13 (2C), 134.68, 131.20, 129.47 (2C), 125.62, 122.79, 121.11, 119.72, 99.09. HRMS-ESI (m/z): [M+H]$^+$ calc. for $C_{15}H_{12}IN_5S^+$, 421.99309; Found: 421.99316. HPLC ($\lambda_{280}$): Purity 98.8%; $t_R$: 6.900 min (method 1).

N—(N-(benzo[d]thiazol-2-yl)carbamimidoyl)benzimidamide (MTF-248)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and benzonitrile (0.54 mL, 5.20 mmol) to afford the titled compound as a beige powder (430 mg, 28%). $^1$H NMR (500 MHz, DMSO-d6): δ 10.28 (br. s, 1H), 9.35 (br. s, 1H), 8.80 (br. s, 1H), 8.03 (d, br. s, J=7.3 Hz, 3H), 7.79 (d, J=7.6 Hz, 1H), 7.66 (d, J=7.9 Hz, 1H), 7.60-7.54 (m, 1H), 7.51 (t, J=7.2 Hz, 2H), 7.34 (t, J=7.4 Hz, 1H), 7.19 (t, J=7.4 Hz, 1H). $^{13}$C NMR (50 MHz, DMSO-d6): δ 172.37, 162.29, 162.21, 151.57, 135.28, 131.44, 131.26, 128.28, 127.60, 125.67, 122.82, 121.15, 119.75. HRMS-ESI (m/z): [M+H]$^+$ calc. for $C_{15}H_{13}N_5S^+$, 296.09644; Found: 296.09659. HPLC ($\lambda_{280}$): Purity 97.9%; $t_R$: 6.358 min (method 1).

N—(N-(benzo[d]thiazol-2-yl)carbamimidoyl)-2-fluorobenzimidamide (MTF-249)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2-fluorobenzonitrile (0.56 mL, 5.20 mmol) to afford the titled compound as a red powder (179 mg, 11%). $^1$H NMR (400 MHz, DMSO-d6): δ 10.16 (s, 1H), 9.31 (s, 1H), 8.69 (s, 1H), 8.05 (s, 1H), 7.80 (d, J=7.7 Hz, 1H), 7.72 (td, J=7.6, 1.4 Hz, 1H), 7.65 (d, J=7.9 Hz, 1H), 7.55 (ddd, J=9.4, 7.3, 1.6 Hz, 1H), 7.37-7.28 (m, 3H), 7.20 (t, J=7.5 Hz, 1H). $^{13}$C NMR (101 MHz, DMSO-d6): δ 172.30 (s), 161.95 (s), 159.34 (d, J=250.6 Hz), 160.01 (s), 151.43 (s), 132.26 (d, J=8.6 Hz), 131.21 (s), 130.39 (d, J=2.6 Hz), 125.62 (s), 124.59 (d, J=13.0 Hz), 124.28 (d, J=3.4 Hz), 122.82 (s), 121.14 (s), 119.73 (s), 116.09 (d, J=21.9 Hz). $^{19}$F NMR (377 MHz, DMSO-d6): δ −114.77. HPLC ($\lambda_{280}$): Purity 97.4%; $t_R$: 6.792 min (method 1).

N—(N-(benzo[d]thiazol-2-yl)carbamimidoyl)-2-bromobenzimidamide (MTF-250)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2-bromobenzonitrile (946 mg, 5.20 mmol) to afford the titled compound as a beige powder (136 mg, 7%). $^1$H NMR (400 MHz, DMSO-d6): δ 9.26 (s, 1H), 7.67 (d, J=7.9 Hz, 1H), 7.54 (d, br. s, J=7.0 Hz, 2H), 7.44 (t, J=7.3 Hz, 2H), 7.35 (t, J=7.1 Hz, 1H), 7.28-7.04 (m, 4H). $^{13}$C NMR (101 MHz, DMSO-d6): δ 173.15, 166.81, 165.00, 139.47, 136.49, 133.16, 132.85, 130.48, 130.28, 128.84, 127.32, 127.03, 126.48, 126.12, 120.08. HRMS-ESI (m/z): [M+H]$^+$ calc. for $C_{15}H_{12}BrN_5S^+$, 374.00696; Found: 374.00702. HPLC ($\lambda_{280}$): Purity 97.8%; $t_R$: 4.158 min (method 1).

N—(N-(benzo[d]thiazol-2-yl)carbamimidoyl)picolinimidamide (MTF-251)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2-pyridinecarbonitrile (541 mg, 5.20 mmol) to afford the titled compound as a white-yellowish powder (955 mg, 62%). $^1$H NMR (200 MHz, DMSO-d6): δ 10.10 (br. s, 1H), 9.40 (br. s, 1H), 8.92 (br. s, 1H), 8.72 (ddd, J=4.7, 1.6, 0.9 Hz, 1H), 8.37 (dt, J=7.9, 1.0 Hz, 1H), 8.03 (br. s, td, J=7.7, 1.7 Hz, 2H), 7.81 (dd, J=7.8, 0.8 Hz, 1H), 7.73-7.58 (m, 2H), 7.35 (td, J=7.7, 1.4 Hz, 1H), 7.20 (td, J=7.6, 1.2 Hz, 1H). $^{13}$C NMR (101 MHz, DMSO-d6): δ 170.26, 167.51, 165.72, 154.24, 149.29, 136.70, 133.47, 128.60, 127.35, 126.57, 126.22, 125.45, 123.31. HRMS-ESI (m/z): [M+H]$^+$ calc. for $C_{14}H_{12}N_6S^+$, 291.09169; Found: 291.09174. HPLC ($\lambda_{280}$): Purity 98.6%; $t_R$: 6.075 min (method 1).

N—(N-(benzo[d]thiazol-2-yl)carbamimidoyl)nicotinimidamide (MTF-252)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol), 3-pyridinecarbonitrile (541 mg, 5.20 mmol) to afford the titled compound as a white-yellowish powder (1.49 g, 97%). $^1$H NMR (200 MHz, DMSO-d6): δ 10.20 (br. s, 1H), 9.34 (br. s, 1H), 9.17 (dd, J=2.2, 0.6 Hz, 1H), 8.95 (br. s, 1H), 8.74 (dd, J=4.8, 1.6 Hz, 1H), 8.37-8.28 (m, 1H), 8.11 (br. s, 1H), 7.66 (dd, J=8.0, 0.6 Hz, 1H), 7.55 (ddd, J=8.0, 4.8, 0.8 Hz, 1H), 7.35 (td, J=7.7, 1.4 Hz, 1H), 7.20 (td, J=7.6, 1.2 Hz, 1H). $^{13}$C NMR (101 MHz, DMSO-d6): δ 172.18, 161.92, 160.34, 151.88, 151.43, 148.75, 135.10, 131.24, 130.86, 125.61, 123.24, 122.82, 121.11, 19.75. HRMS-ESI (m/z): [M+H]$^+$ calc. for C$_{14}$H$_{12}$N$_6$S$^+$, 297.09169; Found: 297.09174. HPLC (λ$_{280}$): Purity 100.0%; t$_R$: 5.592 min (method 1).

N—(N-(benzo[d]thiazol-2-yl)carbamimidoyl)isonicotinimidamide (MTF-253)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-pyridinecarbonitrile (541 mg, 5.20 mmol) to afford the titled compound as a white-yellowish powder (1.12 g, 73%). $^1$H NMR (200 MHz, DMSO-d6): δ 10.15 (br. s, 1H), 9.35 (br. s, 1H), 8.96 (br. s, 1H), 8.76 (dd, J=4.6, 1.5 Hz, 2H), 8.15 (br. s, 1H), 7.91 (dd, J=4.6, 1.5 Hz, 2H), 7.81 (dd, J=7.7, 0.7 Hz, 1H), 7.67 (d, J=8.0 Hz, 1H), 7.42-7.30 (m, 1H), 7.27-7.14 (m, 1H). $^{13}$C NMR (101 MHz, DMSO-d6): δ 172.12, 161.90, 160.07, 151.38, 150.07, 142.53, 131.28, 125.64, 122.88, 121.43, 121.13, 119.81. HRMS-ESI (m/z): [M+H]$^+$ calc. for C$_{14}$H$_{12}$N$_6$S$^+$, 297.09169; Found: 297.09177. HPLC (λ$_{280}$): Purity 95.9%; t$_R$: 5.308 min (method 1).

N—(N-(benzo[d]thiazol-2-yl)carbamimidoyl)-4-methoxybenzimidamide (MTF-254)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-methoxybenzonitrile (692 mg, 5.20 mmol) to afford the titled compound as a beige powder (135 mg, 8%). $^1$H NMR (500 MHz, DMSO-d6): δ 10.27 (br. s, 1H), 9.30 (br. s, 1H), 8.69 (br. s, 1H), 8.03 (d, J=5.9 Hz, 2H), 7.92 (br. s, 1H), 7.78 (d, J=5.4 Hz, 1H), 7.64 (d, J=5.8 Hz, 1H), 7.33 (s, 1H), 7.18 (s, 1H), 7.05 (d, J=5.6 Hz, 2H), 3.83 (s, 3H). $^{13}$C NMR (50 MHz, DMSO-d6): δ 172.33, 162.14, 161.96, 161.71, 151.58, 131.16, 129.40, 127.19, 125.62, 122.72, 121.10, 119.64, 113.56, 55.41. HRMS-ESI (m/z): [M+H]$^+$ calc. for C$_{16}$H$_{15}$N$_5$OS$^+$, 326.10701; Found: 326.10718. HPLC (λ$_{280}$): Purity 95.3%; t$_R$: 6.592 min (method 1).

3-acetyl-N—(N-(benzo[d]thiazol-2-yl)carbamimidoyl)benzimidamide (MTF-255)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-acetylbenzonitrile (755 mg, 5.20 mmol) to afford the titled compound as a red powder (228 mg, 13%). $^1$H NMR (200 MHz, DMSO-d6): δ 10.25 (br. s, 1H), 9.33 (br. s, 1H), 8.98 (br. s, 1H), 8.58 (t, J=1.6 Hz, 1H), 8.30-8.22 (m, 1H), 8.20-7.97 (m, 2H), 7.81 (dd, J=7.8, 0.8 Hz, 1H), 7.68 (t, J=7.7 Hz, 2H), 7.35 (td, J=7.7, 1.4 Hz, 1H), 7.20 (td, J=7.6, 1.2 Hz, 1H), 2.66 (s, 3H). $^{13}$C NMR (50 MHz, DMSO-d6): δ 197.59, 172.28, 162.07, 161.35, 151.50, 136.86, 135.70, 132.04, 131.24, 131.07, 128.79, 127.31, 125.67, 122.85, 121.16, 119.77, 26.89. HRMS-ESI (m/z): [M+H]$^+$ calc. for C$_{17}$H$_{15}$N$_5$OS$^+$, 338.10701; Found: 338.10701. HPLC (λ$_{280}$): Purity 95.2%; t$_R$: 6.283 min (method 1).

3-bromo-N—(N-(4-phenylthiazol-2-yl)carbamimidoyl)benzimidamide (MTF-256)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 3-bromobenzonitrile (833 mg, 4.58 mmol) to afford the titled compound as a yellow powder (715 mg, 39%). $^1$H NMR (500 MHz, DMSO-d6): δ 10.36 (br. s, 1H), 9.15 (br. s, 1H), 8.79 (br. s, 1H), 8.25 (s, 1H), 8.02 (d, J=7.8 Hz, 1H), 7.88 (d, br. s, J=7.3 Hz, 3H), 7.76 (dd, J=7.9, 1.0 Hz, 1H), 7.47 (dd, J=9.1, 6.6 Hz, 2H), 7.43 (t, J=7.7 Hz, 2H), 7.31 (t, J=7.3 Hz, 1H). $^{13}$C NMR (50 MHz, DMSO-d6): δ 173.11, 160.69, 160.04, 149.88, 137.62, 134.52, 133.94, 130.38, 128.71, 127.61, 126.46, 125.61, 121.73, 106.53. HRMS-ESI (m/z): [M+H]$^+$ calc. for C$_{17}$H$_{14}$BrN$_5$S$^+$, 400.02261; Found: 400.02213. HPLC (λ$_{280}$): Purity 98.7%; t$_R$: 7.033 min (method 1).

3-bromo-N—(N-(4-(3-nitrophenyl)thiazol-2-yl)carbamimidoyl)benzimidamide (MTF-257)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 3-bromobenzonitrile (692 mg, 3.80 mmol) to afford the titled compound as a yellow powder (711 mg, 42%). $^1$H NMR (500 MHz, DMSO-d6): δ 10.21 (s, 1H), 8.78 (s, 2H), 8.62 (s, 1H), 8.34 (d, J=7.5 Hz, 1H), 8.23 (s, 1H), 8.19 (br. s, 1H), 8.15 (d, J=7.8 Hz, 1H), 8.01 (d, J=7.5 Hz, 1H), 7.80 (s, 1H), 7.76 (d, J=7.7 Hz, 1H), 7.72 (t, J=7.9 Hz, 1H), 7.48 (t, J=7.8 Hz, 1H). $^{13}$C NMR (50 MHz, DMSO-d6): δ 173.32, 160.75, 159.98, 148.31, 147.48, 137.51, 136.01, 133.95, 131.81, 130.37, 130.20, 126.47, 121.99, 121.66, 119.77, 109.28. HRMS-ESI (m/z): [M+H]$^+$ calc. for C$_{17}$H$_{13}$BrN$_6$O$_2$S$^+$, 445.00768; Found: 445.00806. HPLC (λ$_{280}$): Purity 99.1%; t$_R$: 7.100 min (method 1).

N—(N-(4-(3-nitrophenyl)thiazol-2-yl)carbamimidoyl)picolinimidamide (MTF-259)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 2-pyridinecarbonitrile (366 mL, 3.80 mmol) to afford the titled compound as a yellow powder (796 mg, 57%). $^1$H NMR (500 MHz, DMSO-d6): δ 10.03 (br. s, 1H), 9.08 (br. s, 1H), 8.78 (br. s, 1H), 8.71 (d, J=4.2 Hz, 1H), 8.66-8.61 (m, 1H), 8.38 (d, J=7.9 Hz, 1H), 8.35 (d, J=7.9 Hz, 1H), 8.16 (dd, J=8.1, 1.5 Hz, 1H), 8.02 (td, J=7.8, 1.6 Hz, 1H), 7.91 (br. s, 1H), 7.82 (s, 1H), 7.73 (t, J=8.0 Hz, 1H), 7.63 (ddd, J=7.4, 4.8, 1.0 Hz, 1H). $^{13}$C NMR (50 MHz, DMSO-d6): δ 173.49, 161.02, 158.37, 150.67, 148.58, 148.29, 147.51, 137.39, 135.99, 131.78, 130.16, 126.39, 122.10, 121.99, 119.78, 109.31. HRMS-ESI (m/z): [M+H]$^+$ calc. for C$_{16}$H$_{13}$N$_7$O$_2$S$^+$, 368.09242; Found: 368.09274. HPLC (λ$_{280}$): Purity 99.2%; t$_R$: 6.850 min (method 1).

N—(N-(4-(3-nitrophenyl)thiazol-2-yl)carbamimidoyl)nicotinimidamide (MTF-260)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 3-pyridinecarbonitrile (395 mg, 3.80 mmol) to afford the titled compound as a yellow powder (656 mg, 47%). $^1$H NMR (500 MHz, DMSO-d6): δ 10.14 (br s, 1H), 8.84 (br. s, 2H), 8.75 (d, J=5.8 Hz, 2H), 8.63 (s, 1H), 8.34 (d, J=7.8 Hz, 1H), 8.15 (dd, J=8.0, 1.4 Hz, 1H), 7.91 (d, J=5.8 Hz, 2H), 7.86 (br. s, 1H), 7.82 (s, 1H), 7.72 (t, J=8.0 Hz, 1H). $^{13}$C NMR (50 MHz, DMSO-d6): δ 173.23, 160.74, 159.55, 150.07, 148.33, 147.49, 142.64, 136.00, 131.80, 130.20, 122.01, 121.49, 119.79, 109.48. HRMS-ESI (m/z): [M+H]$^+$ calc. for C$_{16}$H$_{13}$N$_7$O$_2$S$^+$, 368.09242; Found: 368.09283. HPLC (λ$_{280}$): Purity 95.1%; t$_R$: 6.350 min (method 1).

N—(N-(4-(3-nitrophenyl)thiazol-2-yl)carbamimidoyl)isonicotinimidamide (MTF-261)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 4-pyridinecarbonitrile (395 mg, 3.80 mmol) to afford the titled compound as a yellow powder (544 mg, 39%). $^1$H NMR (500 MHz, DMSO-d6): δ 10.14 (br. s, 1H), 9.17 (d, J=1.6 Hz, 1H), 8.81 (br. s, 2H), 8.73 (dd, J=4.7, 1.4 Hz, 1H), 8.63 (s, 1H), 8.33 (t, J=8.4 Hz, 2H), 8.15 (dd, J=8.1, 1.5 Hz, 1H), 7.81 (s, 1H), 7.76 (br. s, 1H), 7.72 (t, J=8.0 Hz, 1H), 7.54 (dd, J=7.8, 4.8 Hz, 1H). $^{13}$C NMR (50 MHz, DMSO-d6): δ 173.30, 160.78, 159.84, 151.81, 148.78, 148.32, 147.48, 136.02, 135.13, 131.79, 130.97, 130.19, 123.25, 121.99, 119.79, 109.31. HRMS-ESI (m/z): [M+H]$^+$ calc. for C$_{16}$H$_{13}$N$_7$O$_2$S$^+$, 368.09242; Found: 368.09283. HPLC (λ$_{280}$): Purity 96.8%; t$_R$: 6.367 min (method 1).

4-methoxy-N—(N-(4-phenylthiazol-2-yl)carbamimidoyl)benzimidamide (MTF-262)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 4-methoxybenzonitrile (610 mg, 4.58 mmol) to afford the titled compound as a beige powder (32 mg, 2%). $^1$H NMR (400 MHz, DMSO-d6): δ 10.30 (br. s, 1H), 9.05 (br. s, 1H), 8.55 (s, 1H), 8.01 (d, J=8.9 Hz, 2H), 7.87 (d, J=7.3 Hz, 2H), 7.68 (br. s, 1H), 7.46 (s, 1H), 7.43 (t, J=7.7 Hz, 1H), 7.31 (t, J=7.3 Hz, 1H), 7.04 (d, J=8.9 Hz, 2H), 3.83 (s, 3H). $^{13}$C NMR (101 MHz, DMSO-d6): δ 173.16, 161.77, 161.07, 160.84, 149.72, 134.54, 129.21, 128.64, 127.50, 127.36, 125.51, 113.46, 106.11, 55.37, 38.89. HRMS-ESI (m/z): [M+H]$^+$ calc. for C$_{18}$H$_{17}$N$_5$OS$^+$, 352.12266; Found: 352.12268. HPLC (λ$_{280}$): Purity 95.1%; t$_R$: 6.842 min (method 1).

N—(N-(4-phenylthiazol-2-yl)carbamimidoyl)picolinimidamide (MTF-263)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 2-pyridinecarbonitrile (441 mL, 4.58 mmol) to afford the titled compound as a yellow powder (369 mg, 25%). $^1$H NMR (500 MHz, DMSO-d6): δ 10.16 (br. s, 1H), 9.19 (br. s, 1H), 8.79 (br. s, 1H), 8.70 (d, J=3.6 Hz, 1H), 8.38 (d, J=7.7 Hz, 1H), 8.01 (t, J=7.4 Hz, 1H), 8.19-7.70 (m, 4H), 7.88 (d, br. s, J=7.4 Hz, 4H), 7.66-7.57 (m, 1H), 7.50 (s, 1H), 7.43 (t, J=7.3 Hz, 2H), 7.32 (t, J=7.0 Hz, 1H). $^{13}$C NMR (50 MHz, DMSO-d6): δ 173.20, 160.91, 158.35, 150.73, 149.86, 148.61, 137.40, 134.50, 128.70, 127.61, 126.38, 125.59, 122.04, 106.61. HRMS-ESI (m/z): [M+H]$^+$ calc. for C$_{16}$H$_{14}$N$_6$S$^+$, 323.10734; Found: 323.10770. HPLC (λ$_{280}$): Purity 98.0%; t$_R$: 6.692 min (method 1).

3-bromo-N—(N-(6-methoxybenzo[d]thiazol-2-yl)carbamimidoyl)benzimidamide (MTF-264)

Synthesized following the general procedure A using 1-(6-methoxybenzo[d]thiazol-2-yl)guanidine (1.00 g, 4.50 mmol), sodium hydride (60% dispersion in mineral oil, 1.5 eq., 270 mg, 6.75 mmol) and 3-bromobenzonitrile (819 mg, 4.50 mmol) to afford the titled compound as a dark gray powder (146 mg, 8%). $^1$H NMR (500 MHz, DMSO-d6): δ 10.29 (br. s, 1H), 9.24 (br. s, 1H), 8.84 (br. s, 1H), 8.23 (s, 1H), 8.01 (d, br. s, J=7.5 Hz, 2H), 7.77 (d, J=7.2 Hz, 1H), 7.56 (d, J=8.6 Hz, 1H), 7.48 (t, J=7.8 Hz, 1H), 7.42 (s, 1H), 6.95 (d, J=8.5 Hz, 1H), 3.79 (s, 3H). $^{13}$C NMR (50 MHz, DMSO-d6): δ 170.29, 161.45, 160.30, 155.69, 145.55, 137.47, 134.03, 132.39, 130.45, 130.36, 126.46, 121.68, 120.37, 113.92, 104.89, 55.55. HRMS-ESI (m/z): [M+H]$^+$ calc. for C$_{16}$H$_{14}$BrN$_5$OS$^+$, 404.01752; Found: 404.01733. HPLC (λ$_{280}$): Purity 95.2%; t$_R$: 6.825 min (method 1).

3-bromo-N—(N-(6-methylbenzo[d]thiazol-2-yl)carbamimidoyl)benzimidamide (MTF-265)

Synthesized following the general procedure A using 1-(6-methylbenzo[d]thiazol-2-yl)guanidine (1.00 g, 4.85 mmol), sodium hydride (60% dispersion in mineral oil, 1.5 eq., 291 mg, 7.28 mmol) and 3-bromobenzonitrile (883 mg, 4.85 mmol) to afford the titled compound as a beige powder (207 mg, 11%). $^1$H NMR (500 MHz, DMSO-d6): δ 10.30 (br. s, 1H), 9.32 (br. s, 1H), 8.87 (br. s, 1H), 8.24 (s, 1H), 8.01 (d, br. s, J=7.6 Hz, 2H), 7.77 (d, J=7.7 Hz, 1H), 7.60 (s, 1H), 7.54 (d, J=8.1 Hz, 1H), 7.48 (t, J=7.8 Hz, 1H), 7.16 (d, J=8.0 Hz, 1H), 2.37 (s, 3H). $^{13}$C NMR (50 MHz, DMSO-d6): δ 171.42, 161.76, 160.43, 149.40, 137.44, 134.05, 132.22, 131.30, 130.41, 126.86, 126.47, 121.69, 120.95, 119.45, 20.93. HRMS-ESI (m/z): [M+H]$^+$ calc. for C$_{16}$H$_{14}$BrN$_5$S$^+$, 388.02261; Found: 388.02313. HPLC (λ$_{280}$): Purity 98.3%; t$_R$: 6.992 min (method 1).

3-chloro-N—(N-(4-phenylthiazol-2-yl)carbamimidoyl)benzimidamide (MTF-267)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 3-chlorobenzonitrile (630 mg, 4.58 mmol) to afford the titled compound as a white-yellowish powder (749 mg, 46%). $^1$H NMR (500 MHz, DMSO-d6): δ 10.36 (br. s, 1H), 9.15 (br. s, 1H), 8.78 (br. s, 1H), 8.10 (t, J=1.7 Hz, 1H), 7.98 (d, J=7.9 Hz, 1H), 7.88 (d, br. s, J=7.2 Hz, 3H), 7.63 (dd, J=8.0, 1.2 Hz, 1H), 7.54 (t, J=7.9 Hz, 1H), 7.48 (s, 1H), 7.43 (t, J=7.7 Hz, 2H), 7.31 (t, J=7.3 Hz, 1H). $^{13}$C NMR (50 MHz, DMSO-d6): δ 173.05, 160.66, 160.04, 149.85, 137.43, 134.51, 133.20, 131.03, 130.14, 128.69, 127.59, 127.46, 126.08, 125.58, 106.53. HRMS-ESI (m/z): [M+H]$^+$ calc. for C$_{17}$H$_{14}$ClN$_5$S$^+$, 356.07312; Found: 356.07321. HPLC (λ$_{280}$): Purity 98.0%; t$_R$: 7.008 min (method 1).

4-chloro-N—(N-(5-phenylthiazol-2-yl)carbamimidoyl)benzimidamide (MTF-268)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 4-chlorobenzonitrile (630 mg, 4.58 mmol) to afford the titled compound as a yellow powder (717 mg, 44%). $^1$H NMR (500 MHz, DMSO-d6): δ 10.35

(br. s, 1H), 9.14 (br. s, 1H), 8.73 (br. s, 1H), 8.05 (d, J=8.6 Hz, 2H), 7.87 (d, J=7.2 Hz, 2H), 7.73 (br. s, 1H), 7.58 (d, J=8.6 Hz, 2H), 7.47 (s, 1H), 7.43 (t, J=7.7 Hz, 2H), 7.31 (t, J=7.3 Hz, 1H). $^{13}$C NMR (50 MHz, DMSO-d6): δ 173.07, 160.72, 160.43, 149.82, 136.13, 134.52, 134.17, 129.37, 128.69, 128.31, 127.58, 125.57, 106.47. HRMS-ESI (m/z): [M+H]$^+$ calc. for $C_{17}H_{14}ClN_5S^+$, 356.07312; Found: 356.07318. HPLC ($\lambda_{280}$): Purity 99.1%; $t_R$: 6.925 min (method 1).

N—(N-(4-phenylthiazol-2-yl)carbamimidoyl)benzimidamide (MTF-272)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and benzonitrile (0.471 mL, 4.58 mmol) to afford the titled compound as a beige powder (486 mg, 33%). $^1$H NMR (500 MHz, DMSO-d6): δ 10.33 (br. s, 1H), 9.13 (br. s, 1H), 8.67 (br. s, 1H), 8.02 (d, J=7.2 Hz, 2H), 7.88 (d, J=7.3 Hz, 2H), 7.72 (br. s, 1H) 7.56 (t, J=7.2 Hz, 1H), 7.49 (dd, J=14.9, 7.7 Hz, 3H), 7.43 (t, J=7.7 Hz, 2H), 7.31 (t, J=7.3 Hz, 1H). $^{13}$C NMR (50 MHz, DMSO-d6): δ 173.16, 161.66, 160.90, 149.80, 135.41, 134.54, 131.26, 128.71 (2C), 128.22 (2C), 127.57, 127.50 (2C), 125.57 (2C), 106.37. HPLC ($\lambda_{280}$): Purity 82.0%; $t_R$: 6.850 min (method 1).

N—(N-(4-phenylthiazol-2-yl)carbamimidoyl)nicotinimidamide (MTF-273)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 3-cyanopyridine (477 mg, 4.58 mmol) to afford the titled compound as a yellowish powder (694 mg, 47%). $^1$H NMR (500 MHz, DMSO-d6): δ 10.30 (br. s, 1H), 9.17 (d, br. s, J=1.6 Hz, 2H), 8.82 (br. s, 1H), 8.73 (dd, J=4.7, 1.4 Hz, 1H), 8.33 (d, J=8.0 Hz, 1H), 7.88 (d, br. s, J=7.3 Hz, 3H), 7.54 (dd, J=7.8, 4.8 Hz, 1H), 7.49 (s, 1H), 7.43 (t, J=7.6 Hz, 2H), 7.32 (t, J=7.3 Hz, 1H). $^{13}$C NMR (50 MHz, DMSO-d6): δ 173.07, 160.68, 159.88, 151.80, 149.86, 148.77, 135.10, 134.52, 131.05, 128.71, 127.60, 125.59, 123.25, 106.58. HRMS-ESI (m/z): [M+H]$^+$ calc. for $C_{16}H_{14}N_6S^+$, 323.10734; Found: 323.10764. HPLC ($\lambda_{280}$): Purity 96.9%; $t_R$: 6.075 min (method 1).

N—(N-(4-phenylthiazol-2-yl)carbamimidoyl)isonicotinimidamide (MTF-274)

Synthesized following the general procedure A using 1-(4-phenylthiazol-2-yl)guanidine (1.00 g, 4.58 mmol), sodium hydride (60% dispersion in mineral oil, 1.5 eq., 275 mg, 6.87 mmol) and 4-pyridinecarbonitrile (477 mg, 4.58 mmol) to afford the titled compound as a yellowish powder (871 mg, 59%). $^1$H NMR (500 MHz, DMSO-d6): δ 10.30 (br. s, 1H), 9.20 (br. s, 1H), 8.86 (br. s, 1H), 8.75 (dd, J=4.5, 1.6 Hz, 2H), 7.92 (dd, J=4.5, 1.6 Hz, 2H), 7.88 (d, br. s, J=7.2 Hz, 3H), 7.50 (s, 1H), 7.43 (t, J=7.7 Hz, 2H), 7.32 (t, J=7.3 Hz, 1H). $^{13}$C NMR (50 MHz, DMSO-d6): δ 173.00, 160.64, 159.63, 150.09, 149.90, 142.74, 134.50, 128.72, 127.63, 125.61, 121.49, 106.75. HRMS-ESI (m/z): [M+H]$^+$ calc. for $C_{16}H_{14}N_6S^+$, 323.10734; Found: 323.10757. HPLC ($\lambda_{280}$): Purity 95.2%; $t_R$: 6.058 min (method 1).

2-chloro-N—(N-(4-(3-nitrophenyl)thiazol-2-yl)carbamimidoyl)benzimidamide (MTF-276)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 2-chlorobenzonitrile (523 mg, 3.80 mmol) to afford the titled compound as a brown powder (30 mg, 2%). $^1$H NMR (400 MHz, DMSO-d6): δ 10.08 (br. s, 1H), 8.83 (br. s, 1H), 8.70 (br. s, 1H), 8.62 (s, 1H), 8.34 (d, J=7.7 Hz, 1H), 8.15 (d, J=7.4 Hz, 1H), 8.03-7.64 (br. s, 1H), 7.81 (s, 1H), 7.72 (t, J=7.7 Hz, 1H), 7.52 (t, J=7.8 Hz, 2H), 7.49-7.37 (m, 2H). $^{13}$C NMR (101 MHz, DMSO-d6): δ 173.55, 162.25, 160.72, 148.36, 147.36, 136.69, 136.00, 131.76, 130.52, 130.25 (2C), 129.51, 129.39, 126.87, 121.95, 119.70, 109.25. HRMS-ESI (m/z): [M+H]$^+$ calc. for $C_{17}H_{13}ClN_6O_2S^+$, 401.05820; Found: 401.05820. HPLC ($\lambda_{280}$): Purity 95.2%; $t_R$: 6.858 min (method 1).

3-chloro-N—(N-(4-(3-nitrophenyl)thiazol-2-yl)carbamimidoyl)benzimidamide (MTF-277)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 3-chlorobenzonitrile (523 mg, 3.80 mmol) to afford the titled compound as a brown powder (457 mg, 30%). $^1$H NMR (500 MHz, DMSO-d6): δ 10.22 (br. s, 1H), 8.77 (br. s, 1H), 8.62 (s, 1H), 8.34 (d, J=7.7 Hz, 1H), 8.23-7.91 (br. s, 1H), 8.15 (d, J=8.0 Hz, 1H), 8.09 (s, 1H), 7.97 (d, J=7.7 Hz, 1H), 7.80 (s, 1H), 7.72 (t, J=8.0 Hz, 1H), 7.63 (d, J=7.9 Hz, 1H), 7.54 (t, J=7.9 Hz, 1H). $^{13}$C NMR (50 MHz, DMSO-d6): δ 173.31, 160.75, 160.02, 148.34, 147.48, 137.34, 136.02, 133.17, 131.83, 131.05, 130.24, 130.17, 127.45, 126.11, 122.02, 119.78, 109.32. HRMS-ESI (m/z): [M+H]$^+$ calc. for $C_{17}H_{13}ClN_6O_2S^+$, 401.05820; Found: 401.05835. HPLC ($\lambda_{280}$): Purity 95.5%; $t_R$: 7.025 min (method 1).

4-chloro-N—(N-(4-(3-nitrophenyl)thiazol-2-yl)carbamimidoyl)benzimidamide (MTF-281)

Synthesized following the general procedure A using 1-(4-(3-nitrophenyl)thiazol-2-yl)guanidine (1.00 g, 3.80 mmol), sodium hydride (60% dispersion in mineral oil, 1.5 eq., 228 mg, 5.70 mmol) and 4-chlorobenzonitrile (523 mg, 3.80 mmol) to afford the titled compound as a yellow powder (640 mg, 42%). $^1$H NMR (200 MHz, DMSO-d6): δ 10.15 (br. s, 1H), 8.74 (br. s, 2H), 8.68-8.60 (m, 1H), 8.55-7.90 (br. s, 1H), 8.39-8.30 (m, 1H), 8.16 (ddd, J=8.2, 2.3, 0.8 Hz, 1H), 8.10-7.97 (m, 2H), 7.82 (s, 1H), 7.72 (t, J=8.0 Hz, 1H), 7.66-7.48 (m, 2H). $^{13}$C NMR (50 MHz, DMSO-d6): δ 173.37, 160.84, 160.46, 148.30, 147.47, 136.17, 136.04, 134.10, 131.77, 130.16, 129.40 (2C), 128.29 (2C), 121.96, 119.77, 109.19. HRMS-ESI (m/z): [M+H]$^+$ calc. for $C_{17}H_{13}ClN_6O_2S^+$, 401.05820; Found: 401.05820. HPLC ($\lambda_{280}$): Purity 96.7%; $t_R$: 7.033 min (method 1).

N—(N-(4-methylthiazol-2-yl)carbamimidoyl)benzimidamide (MTF-283)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and benzonitrile (0.66 mL, 6.41 mmol) to afford the titled compound as a brown powder (382 mg, 23%). $^1$H NMR (500 MHz, DMSO-d6): δ 10.42 (br. s, 1H), 9.11 (br. s, 1H), 8.61 (br. s, 1H), 8.02-7.96 (m, 2H), 7.57-7.52 (m, 1H), 7.85-7.39 (br. s, 4H), 7.51-7.46 (m, 2H), 6.57 (d, J=1.0 Hz, 1H), 2.24 (d, J=0.9 Hz, 3H). $^{13}$C NMR (50 MHz, DMSO-d6): δ 172.99, 161.63, 160.69, 147.64, 135.50, 131.20, 128.21, 127.45, 105.64, 17.56. HRMS-ESI (m/z): [M+H]⁺ calc. for $C_{12}H_{13}N_5S^+$, 260.09644; Found: 260.09653. HPLC ($\lambda_{280}$): Purity 95.7%; $t_R$: 5.167 min (method 1).

2-chloro-N—(N-(4-methylthiazol-2-yl)carbamimidoyl)benzimidamide (MTF-284)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 2-chlorobenzonitrile (881 mg, 6.41 mmol) to afford the titled compound as a white powder (132 mg, 7%). ¹H NMR (400 MHz, DMSO-d6): δ 10.27 (br. s, 1H), 9.06 (br. s, 1H), 8.63 (br. s, 1H), 7.63 (br. s, 1H), 7.46 (m, 4H), 6.57 (s, 1H), 2.24 (s, 3H). ¹³C NMR (101 MHz, DMSO-d6): δ 172.87, 162.18, 160.47, 147.49, 136.79, 130.49, 130.27, 129.55, 129.40, 126.88, 105.69, 17.46. HRMS-ESI (m/z): [M+H]⁺ calc. for $C_{12}H_{12}ClN_5S^+$, 294.05747; Found: 294.05747. HPLC ($\lambda_{280}$): Purity 95.0%; $t_R$: 5.500 min (method 1).

3-chloro-N—(N-(4-methylthiazol-2-yl)carbamimidoyl)benzimidamide (MTF-285)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 3-chlorobenzonitrile (881 mg, 6.41 mmol) to afford the titled compound as a white-yellowish (1.24 g, 66%). ¹H NMR (500 MHz, DMSO-d6): δ 10.43 (br. s, 1H), 9.13 (br. s, 1H), 8.71 (br. s, 1H), 8.11-8.05 (m, 1H), 7.95 (d, J=7.9 Hz, 1H), 7.64-7.59 (m, 1H), 7.58 (br.s, 1H), 7.53 (t, J=7.9 Hz, 1H), 6.59 (d, J=0.9 Hz, 1H), 2.25 (d, J=0.5 Hz, 3H). ¹³C NMR (50 MHz, DMSO-d6): δ 172.82, 160.44, 159.91, 147.64, 137.47, 133.18, 130.97, 130.15, 127.39, 126.00, 105.82, 17.53. HRMS-ESI (m/z): [M+H]⁺ calc. for $C_{12}H_{12}ClN_5S^+$, 294.05747; Found: 294.05768. HPLC ($\lambda_{280}$): Purity 95.0%; $t_R$: 5.933 min (method 1).

4-chloro-N—(N-(4-methylthiazol-2-yl)carbamimidoyl)benzimidamide (MTF-286)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 4-chlorobenzonitrile (881 mg, 6.41 mmol) to afford the titled compound as a white-yellowish (923 mg, 49%). ¹H NMR (500 MHz, DMSO-d6): δ 10.42 (br. s, 1H), 9.13 (br. s, 1H), 8.67 (br. s, 1H), 8.01 (d, J=8.6 Hz, 2H), 7.57 (d, br. s J=8.6 Hz, 3H), 6.57 (d, J=1.0 Hz, 1H), 2.24 (d, J=0.7 Hz, 3H). ¹³C NMR (50 MHz, DMSO-d6): δ 172.87, 160.50, 160.37, 147.63, 136.08, 134.23, 129.30, 128.29, 105.74, 17.53. HRMS-ESI (m/z): [M+H]⁺ calc. for $C_{12}H_{12}ClN_5S^+$, 294.05747; Found: 294.05762. HPLC ($\lambda_{280}$): Purity 95.3%; $t_R$: 5.958 min (method 1).

2-bromo-N—(N-(4-methylthiazol-2-yl)carbamimidoyl)benzimidamide (MTF-287)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 2-bromobenzonitrile (1.17 g, 6.41 mmol) to afford the titled compound as a white-yellowish (499 mg, 23%). ¹H NMR (400 MHz, DMSO-d6): δ 10.27 (br. s, 1H), 9.07 (br. s, 1H), 8.63 (br. s, 1H), 7.67 (d, br. s, J=7.9 Hz, 2H), 7.46-7.43 (m, 2H), 7.36 (ddd, J=8.1, 6.0, 3.2 Hz, 1H), 6.57 (s, 1H), 2.24 (s, 3H). ¹³C NMR (101 MHz, DMSO-d6): δ 172.89, 163.29, 160.49, 147.50, 138.85, 132.49, 130.57, 129.44, 127.37, 119.62, 105.68, 17.46. HRMS-ESI (m/z): [M+H]⁺ calc. for $C_{12}H_{12}BrN_5S^+$, 338.00696; Found: 338.00705. HPLC ($\lambda_{280}$): Purity 95.8%; $t_R$: 5.192 min (method 1).

3-bromo-N—(N-(4-methylthiazol-2-yl)carbamimidoyl)benzimidamide (MTF-288)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 3-bromobenzonitrile (1.17 g, 6.41 mmol) to afford the titled compound as a white-yellowish (1.11 g, 51%). ¹H NMR (500 MHz, DMSO-d6): δ 10.42 (s, 1H), 9.12 (s, 1H), 8.72 (s, 1H), 8.21 (t, J=1.7 Hz, 1H), 7.98 (d, J=8.0 Hz, 1H), 7.75 (dd, br. s, J=8.0, 1.1 Hz, 2H), 7.46 (t, J=7.9 Hz, 1H), 6.59 (d, J=0.9 Hz, 1H), 2.24 (d, J=0.8 Hz, 3H). ¹³C NMR (50 MHz, DMSO-d6): δ 172.80, 160.42, 159.83, 147.63, 137.63, 133.86, 130.38, 130.27, 126.35, 121.66, 105.81, 17.53. HRMS-ESI (m/z): [M+H]⁺ calc. for $C_{12}H_{12}BrN_5S^+$, 338.00696; Found: 338.00760. HPLC ($\lambda_{280}$): Purity 95.1%; $t_R$: 6.042 min (method 1).

N—(N-(4-methylthiazol-2-yl)carbamimidoyl)picolinimidamide (MTF-289)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 2-pyridinecarbonitrile (0.617 mL, 6.41 mmol) to afford the titled compound as a yellow powder (1.05 g, 63%). ¹H NMR (200 MHz, DMSO-d6): δ 10.20 (s, 1H), 9.15 (s, 1H), 8.77 (s, 1H), 8.73-8.65 (m, 1H), 8.34 (d, J=8.5 Hz, 1H), 8.00 (td, J=7.8, 1.7 Hz, 1H), 7.61 (ddd, J=7.4, 4.8, 1.1 Hz, 2H), 6.60 (d, J=1.0 Hz, 1H), 2.25 (s, 3H). ¹³C NMR (101 MHz, DMSO-d6): δ 172.90, 160.61, 158.17, 150.75, 148.52, 147.60, 137.32, 126.26, 121.87, 105.82, 17.46. HRMS-ESI (m/z): [M+H]⁺ calc. for $C_{11}H_{12}N_6S^+$, 261.09169; Found: 261.09174. HPLC ($\lambda_{280}$): Purity 95.7%; $t_R$: 5.708 min (method 1).

N—(N-(4-methylthiazol-2-yl)carbamimidoyl)nicotinimidamide (MTF-290)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 3-pyridinecarbonitrile (0.667 mg, 6.41 mmol) to afford the titled compound as a yellow powder (751 mg, 45%). ¹H NMR (500 MHz, DMSO-d6): δ 10.39 (br. s, 1H), 9.15 (d, br. s, J=1.7 Hz, 2H), 8.77 (br. s, 1H), 8.71 (dd, J=4.7, 1.5 Hz, 1H), 8.36-8.23 (m, 1H), 7.65 (br. s, 1H), 7.52 (dd, J=7.5, 4.8 Hz, 1H), 6.59 (d, J=0.7 Hz, 1H), 2.25 (s, 3H). ¹³C NMR (50 MHz, DMSO-d6): δ 172.84, 160.46, 159.79, 151.75, 148.72, 147.67, 135.03, 131.09, 123.24, 105.89, 17.54. HRMS-ESI (m/z): [M+H]⁺ calc. for $C_{11}H_{12}N_6S^+$, 261.09169; Found: 261.09171. HPLC ($\lambda_{280}$): Purity 97.1%; $t_R$: 5.508 min (method 1).

N—(N-(4-methylthiazol-2-yl)carbamimidoyl)isonicotinimidamide (MTF-291)

Synthesized following the general procedure A using 1-(4-methylthiazol-2-yl)guanidine (1.00 g, 6.41 mmol), sodium hydride (60% dispersion in mineral oil, 384 mg, 9.61 mmol) and 4-pyridinecarbonitrile (0.667 mg, 6.41 mmol) to afford the titled compound as a yellow powder (985 mg, 59%). $^1$H NMR (500 MHz, DMSO-d6): δ 10.37 (br. s, 1H), 9.15 (br. s, 1H), 8.80 (br. s, 1H), 8.74 (dd, J=4.5, 1.6 Hz, 2H), 7.89 (dd, J=4.5, 1.6 Hz, 2H), 7.68 (br. s, 1H), 6.60 (d, J=0.9 Hz, 1H), 2.25 (d, J=0.8 Hz, 3H). $^{13}$C NMR (50 MHz, DMSO-d6): δ 172.77, 160.43, 159.58, 150.08, 147.74, 142.81, 121.45, 106.08, 17.54. HRMS-ESI (m/z): [M+H]$^+$ calc. for $C_{11}H_{12}N_6S^+$, 261.09169; Found: 261.09174. HPLC ($\lambda_{280}$): Purity 99.5%; $t_R$: 4.525 min (method 1).

4-methoxy-N—(N-(4-methylthiazol-2-yl)carbamimidoyl)benzimidamide (MTF-292)

Synthesized following the general procedure A using 1-(4-methylthiazol-2-yl)guanidine (1.00 g, 6.41 mmol), sodium hydride (60% dispersion in mineral oil, 1.5 eq., 384 mg, 9.61 mmol) and 4-methoxybenzonitrile (0.853 mg, 6.41 mmol) to afford the titled compound as a beige powder (167 mg, 9%). $^1$H NMR (500 MHz, DMSO-d6): δ 10.40 (br. s, 1H), 9.06 (br. s, 1H), 8.50 (br. s, 1H), 7.98 (d, J=8.9 Hz, 2H), 7.49 (br. s, 1H), 7.02 (d, J=8.9 Hz, 2H), 6.55 (d, J=0.8 Hz, 1H), 3.83 (s, 3H), 2.24 (s, 3H). $^{13}$C NMR (101 MHz, DMSO-d6): δ 172.97, 161.71, 160.99, 160.62, 147.51, 129.13, 127.43, 113.43, 105.33, 55.34, 17.48. HRMS-ESI (m/z): [M+H]$^+$ calc. for $C_{13}H_{15}N_5OS^+$, 290.10701; Found: 290.10709. HPLC ($\lambda_{280}$): Purity 100.0%; $t_R$: 5.308 min (method 1).

2-bromo-N—(N-(4,5-dimethylthiazol-2-yl)carbamimidoyl)benzimidamide (MTF-295)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and 2-bromobenzonitrile (1.07 g, 5.88 mmol) to afford the titled compound as a brown powder (746 mg, 36%). $^1$H NMR (500 MHz, DMSO-d6): δ 10.28 (br. s, 1H), 9.01 (br. s, 1H), 8.58 (br. s, 1H), 7.70-7.30 (br. s, 1H), 7.67 (d, J=7.9 Hz, 1H), 7.44 (dd, J=8.1, 5.2 Hz, 2H), 7.40-7.33 (m, 1H), 2.21 (s, 3H), 2.14 (s, 3H). $^{13}$C NMR (101 MHz, DMSO-d6): δ 169.26, 163.14, 160.22, 142.62, 138.85, 132.48, 130.54, 129.44, 127.36, 119.64, 116.98, 14.58, 10.71. HRMS-ESI (m/z): [M+H]$^+$ calc. for $C_{13}H_{14}BrN_5S^+$, 352.02261; Found: 352.02289. HPLC ($\lambda_{280}$): Purity 97.8%; $t_R$: 5.717 min (method 1).

2-bromo-N—(N-(4,5-dimethylthiazol-2-yl)carbamimidoyl)benzimidamide (MTF-296)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and 3-bromobenzonitrile (1.07 g, 5.88 mmol) to afford the titled compound as a brown powder brown powder (746 mg, 36%). $^1$H NMR (200 MHz, DMSO-d6): δ 10.45 (br. s, 1H), 9.01 (br. s, 1H), 8.70 (br. s, 1H), 8.20 (t, J=1.7 Hz, 1H), 8.06-7.28 (br. s, 1H), 7.97 (d, J=8.0 Hz, 1H), 7.74 (ddd, J=7.9, 1.9, 0.8 Hz, 1H), 7.46 (t, J=7.9 Hz, 1H), 2.21 (s, 3H), 2.15 (s, 3H). $^{13}$C NMR (50 MHz, DMSO-d6): δ 169.14, 160.12, 159.63, 142.74, 137.65, 133.81, 130.41, 130.18, 126.29, 121.61, 117.13, 14.63, 10.76. HRMS-ESI (m/z): [M+H]$^+$ calc. for $C_{13}H_{15}BrN_5S^+$, 352.02261; Found: 352.02377. HPLC ($\lambda_{280}$): Purity 97.3%; $t_R$: 5.767 min (method 1).

N—(N-(4,5-dimethylthiazol-2-yl)carbamimidoyl)picolinimidamide (MTF-297)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and 2-pyridinecarbonitrile (0.566 mL, 5.88 mmol) to afford the titled compound as a yellow powder (726 mg, 45%). $^1$H NMR (500 MHz, DMSO-d6): δ 10.19 (br. s, 1H), 9.09 (br. s, 1H), 8.68 (d, br. s. J=4.1 Hz, 2H), 8.33 (d, J=7.9 Hz, 1H), 7.99 (td, J=7.7, 1.3 Hz, 1H), 7.60 (dd, br. s., J=6.5, 5.0 Hz, 2H), 2.21 (s, 3H), 2.15 (s, 3H). $^{13}$C NMR (101 MHz, DMSO-d6): δ 169.29, 160.32, 158.01, 150.80, 148.50, 142.71, 137.28, 126.19, 121.80, 117.16, 14.56, 10.69. HRMS-ESI (m/z): [M+H]$^+$ calc. for $C_{12}H_{14}N_6S^+$, 275.10734; Found: 275.10742. HPLC ($\lambda_{280}$): Purity 100.0%; $t_R$: 5.475 min (method 1).

N—(N-(4,5-dimethylthiazol-2-yl)carbamimidoyl)nicotinimidamide (MTF-298)

Synthesized following the general procedure A using 1-(4,5-dimethylthiazol-2-yl)guanidine (1.00 g, 5.88 mmol), sodium hydride (60% dispersion in mineral oil, 353 mg, 8.82 mmol) and 3-pyridinecarbonitrile (612 mg, 5.88 mmol) to afford the titled compound as a yellow powder (742 mg, 46%). $^1$H NMR (500 MHz, DMSO-d6): δ 10.43 (br. s, 1H), 9.04 (br. s, 1H), 8.67 (br. s, 1H), 8.20 (t, J=1.6 Hz, 1H), 7.97 (d, J=8.0 Hz, 1H), 7.80-7.70 (m, 1H), 7.88-7.29 (br. s, 1H), 7.46 (t, J=7.9 Hz, 1H), 2.21 (s, 3H), 2.15 (s, 3H). $^{13}$C NMR (101 MHz, DMSO-d6): δ 169.13, 160.11, 159.55, 151.63, 148.60, 142.72, 134.89, 131.06, 123.17, 117.16, 14.57, 10.69. HRMS-ESI (m/z): [M+H]$^+$ calc. for $C_{12}H_{14}N_6S^+$, 275.10734; Found: 275.10736. HPLC ($\lambda_{280}$): Purity 97.0%; $t_R$: 5.458 min (method 1).

N—(N-(4,5-dimethylthiazol-2-yl)carbamimidoyl)isonicotinimidamide (MTF-299)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and 4-pyridinecarbonitrile (612 mg, 5.88 mmol) to afford the titled compound as a yellow powder (548 mg, 34%). $^1$H NMR (500 MHz, DMSO-d6): δ 10.40 (br. s, 1H), 9.09 (br. s, 1H), 8.73 (d, br. s., J=5.7 Hz, 3H), 7.88 (d, J=5.5 Hz, 2H), 7.61 (br. s, 1H), 2.21 (s, 3H), 2.15 (s, 3H). $^{13}$C NMR (101 MHz, DMSO-d6): δ 169.05, 160.06, 159.33, 149.98, 142.78, 121.31, 117.38, 14.55, 10.68. HRMS-ESI (m/z): [M+H]$^+$ calc. for $C_{12}H_{14}N_6S^+$, 275.10734; Found: 275.10739. HPLC ($\lambda_{280}$): Purity 99.5%; $t_R$: 5.108 min (method 1).

2-chloro-N—(N-(4,5-dimethylthiazol-2-yl)carbamimidoyl)benzimidamide (MTF-300)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and 2-chlorobenzonitrile (809 mg, 5.88 mmol) to afford the titled compound as a yellow powder (109 mg, 6%). $^1$H NMR (500 MHz, DMSO-d6): δ 10.30 (br. s, 1H), 9.01 (br. s, 1H), 8.59 (br. s, 1H), 7.46 (m, 5H), 2.21 (s, 3H), 2.14 (s, 3H). $^{13}$C NMR (101 MHz, DMSO-d6): δ 169.26, 162.01, 160.22, 142.63, 136.82, 130.47, 130.28, 129.56, 129.39, 126.88, 117.00, 14.58, 10.71. HRMS-ESI (m/z): [M+H]$^+$ calc. for $C_{13}H_{14}CN_5S^+$, 308.07312; Found: 308.07318. HPLC ($\lambda_{280}$): Purity 95.4%; $t_R$: 5.425 min (method 1).

3-chloro-N—(N-(4,5-dimethylthiazol-2-yl)carbamimidoyl)benzimidamide (MTF-301)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and 3-chlorobenzonitrile (809 mg, 5.88 mmol) to afford the titled compound as a yellow powder (416 mg, 23%). $^1$H NMR (500 MHz, DMSO-d6): δ 10.44 (br. s, 1H), 9.04 (br. s, 1H), 8.68 (br. s, 1H), 8.08-8.03 (m, 1H), 7.93 (d, J=7.9 Hz, 1H), 7.61 (ddd, J=8.0, 2.1, 0.9 Hz, 1H), 7.78-7.39 (br. s, 1H), 7.52 (t, J=7.9 Hz, 1H), 2.21 (s, 3H), 2.15 (s, 3H). $^{13}$C NMR (50 MHz, DMSO-d6): δ 169.15, 160.14, 159.71, 142.73, 137.49, 133.13, 130.91, 130.15, 127.31, 125.93, 117.14, 14.62, 10.75. HRMS-ESI (m/z): [M+H]$^+$ calc. for $C_{13}H_{14}CN_5S^+$, 308.07312; Found: 308.07321. HPLC ($\lambda_{280}$): Purity 95.2%; $t_R$: 6.075 min (method 1).

4-chloro-N—(N-(4,5-dimethylthiazol-2-yl)carbamimidoyl)benzimidamide (MTF-302)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) 4-chlorobenzonitrile (809 mg, 5.88 mmol to afford the titled compound as a yellow powder (90 mg, 5%). $^1$H NMR (500 MHz, DMSO-d6): δ 10.44 (br. s, 1H), 9.04 (br. s, 1H), 8.64 (br. s, 1H), 8.01 (d, J=8.6 Hz, 2H), 7.57 (d, br. s, J=8.6 Hz, 3H), 2.22 (s, 3H), 2.15 (s, 3H). $^{13}$C NMR (101 MHz, DMSO-d6): δ 169.15, 160.16, 160.11, 142.66, 135.93, 134.23, 129.19 (2C), 128.22 (2C), 117.02, 14.57, 10.70. HRMS-ESI (m/z): [M+H]$^+$ calc. for $C_{13}H_{14}ClN_5S^+$, 308.07312; Found: 308.07315. HPLC ($\lambda_{280}$): Purity 98.0%; $t_R$: 6.267 min (method 1).

N—(N-(4,5-dimethylthiazol-2-yl)carbamimidoyl)benzimidamide (MTF-303)

Synthesized following the general procedure A using 1-(4,5-dimethylthiazol-2-yl)guanidine (1.00 g, 5.88 mmol), sodium hydride (60% dispersion in mineral oil, 1.5 eq., 353 mg, 8.82 mmol) and benzonitrile (0.605 mL, 5.88 mmol) to afford the titled compound as a yellow powder (113 mg, 7%). $^1$H NMR (200 MHz, DMSO-d6): δ 10.45 (s, 1H), 8.94 (s, 1H), 8.61 (s, 1H), 7.98 (dd, J=7.9, 1.7 Hz, 2H), 7.84-7.31 (m, 4H), 2.21 (d, J=0.6 Hz, 3H), 2.15 (s, 3H). $^{13}$C NMR (101 MHz, DMSO-d6): δ 169.26, 161.31, 160.33, 142.65, 135.47, 131.06, 128.12, 127.30, 116.88, 14.58, 10.70. HRMS-ESI (m/z): [M+H]$^+$ calc. for $C_{13}H_{15}N_5S^+$, 274.11209; Found: 274.11212. HPLC ($\lambda_{280}$): Purity 97.5%; $t_R$: 5.408 min (method 1).

N—(N-(benzo[d]thiazol-2-yl)carbamimidoyl)-2,2,2-trichloroacetimidamide (MTF-305)

A solution of 1-(benzo[d]thiazol-2-yl)guanidine (500 mg, 2.6 mmol) and trichloroacetonitrile (260 μL, 2.6 mmol) in technical grade ethanol (5 mL) was stirred at r.t. under argon atmosphere for 22 h. The precipitate that formed was filtered, washed with little amount of cold ethanol, then with a very little amount of diethyl ether, dried quickly at air (the compound oxidized over time at air) and stored under argon. Yellow solid (100 mg, 11%). TLC: $R_f$ (CHCl$_3$/MeOH, 95/5, v/v)=0.90. $^1$H NMR (400 MHz, Acetone-d6): δ 10.71 (s, 1H), 9.84 (s, 1H), 8.39 (s, 1H), 7.80 (dd, J=7.9, 1.3 Hz, 1H), 7.72 (d, J=8.0 Hz, 1H), 7.66 (s, 1H), 7.38 (td, J=8.2, 7.8, 1.3 Hz, 1H), 7.25 (td, J=7.6, 1.2 Hz, 1H). $^{13}$C NMR (101 MHz, Acetone-d6): δ 206.12, 126.63, 124.28, 121.93, 121.33. HRMS-ESI (m/z): [M+H]$^+$ calc. for $C_{10}H_9Cl_3N_5S^+$, 335.96388; Found: 335.96420. HPLC ($\lambda_{254}$): Purity 99.7%; $t_R$: 7.983 min (method 1).

N2-(2-(methylthio)phenyl)-6-(trichloromethyl)-1,3,5-triazine-2,4-diamine (MTF-316)

To suspension of N2,N2'-(disulfanediylbis(2,1-phenylene))bis(6-(trichloromethyl)-1,3,5-triazine-2,4-diamine) CRO15 (150 mg, 0.225 mmol) in methanol (10 mL) was added mercaptoethanol (350 μL, 4.5 mmol) and the mixture stirred at r.t. After 10 min stirring, total solubility was reached. TLC and LCMS showed total conversion into the reduced thiophenol. After 20 h stirring at r.t., K$_2$CO$_3$ (62.1 mg, 0.45 mmol) was added and the mixture sonicated until total solubilisation. Then MeI (28 μL, 0.45 mmol) was added and the solution stirred for 5 h at r.t. (reaction time not optimized). TLC and LCMS showed total conversion into two new compounds (ratio 2/1). The mixture was extracted with EtOAc twice and the combined organic layers were dried with Na$_2$SO$_4$ and evaporated under reduced pressure. Purification by silicagel flash chromatography (cyclohexane/EtOAc, 10/0 to 7/3, v/v) afforded the desired compound as white crystals (27.0 mg, 34% over 2 steps). $^1$H NMR (200 MHz, Acetone-d6): S 8.04 (s, 1H), 7.73 (d, J=7.9 Hz, 1H), 7.11 (dd, J=7.7, 1.7 Hz, 1H), 7.01-6.57 (m, 4H), 2.05 (s, 3H). $^{13}$C NMR (50 MHz, Acetone-d6): δ 174.04, 168.91, 166.25, 138.04, 131.38, 130.32, 128.05, 125.84, 124.21, 97.43. HRMS-ESI (m/z): [M+H]$^+$ calc. for $C_{11}H_{11}Cl_3N_5S^+$, 349.97953; Found: 349.97983. HPLC ($\lambda_{254}$): Purity 97.6%; $t_R$: 10.483 min (method 2).

6-(dichloromethyl)-N2-(2-(methylthio)phenyl)-1,3,5-triazine-2,4-diamine (MTF-317)

To suspension of N2,N2'-(disulfanediylbis(2,1-phenylene))bis(6-(trichloromethyl)-1,3,5-triazine-2,4-diamine) CRO15 (150 mg, 0.225 mmol) in methanol (10 mL) was added mercaptoethanol (350 μL, 4.5 mmol) and the mixture stirred at r.t. After 10 min stirring, total solubility was reached. TLC and LCMS showed total conversion into the reduced thiophenol. After 20 h stirring at r.t., K$_2$CO$_3$ (62.1 mg, 0.45 mmol) was added and the mixture sonicated until total solubilisation. Then MeI (28 μL, 0.45 mmol) was added and the solution stirred for 5 h at r.t. (reaction time not optimized). TLC and LCMS showed total conversion into two new compounds (ratio 2/1). The mixture was extracted with EtOAc twice and the combined organic layers were dried with Na$_2$SO$_4$ and evaporated under reduced pressure. Purification by silicagel flash chromatography (cyclohexane/EtOAc, 10/0 to 7/3, v/v) afforded the titled compound as white crystals (12.7 mg, 18% over 2 steps). $^1$H NMR (200 MHz, Acetone-d6): δ 8.27 (s, 1H), 8.19-8.07 (m, 1H), 7.49 (dd, J=7.6, 1.7 Hz, 1H), 7.32-7.23 (m, 1H), 7.16 (td, J=7.5, 1.5 Hz, 1H), 6.90 (s, 2H), 6.54 (s, 1H), 2.43 (s, 3H). $^{13}$C NMR (50 MHz, Acetone-d6): δ 173.85, 168.61, 166.05, 138.23, 131.54, 130.28, 128.11, 125.67, 124.06, 71.59, 17.73. HRMS-ESI (m/z): [M+H]$^+$ calc. for $C_{11}H_{12}Cl_2N_5S^+$, 316.01850; Found: 316.01892. HPLC ($\lambda_{254}$): Purity 97.3%; $t_R$: 10.658 min (method 2).

N2,N2'-(disulfanediylbis(2,1-phenylene))bis(6-(3-methoxyphenyl)-1,3,5-triazine-2,4-diamine (MTF-318)

Synthesized following the general procedure B using N—(N-(benzo[d]thiazol-2-yl)carbamimidoyl)-3-methoxybenzimidamide (325 mg, 1 mmol) to afford the titled compound as a white powder (272 mg, 84%). $^1$H NMR (200 MHz, DMSO-d6): δ 9.25 (s, 2H), 7.82 (dd, J=8.1, 5.1 Hz, 4H), 7.61 (dd, J=7.7, 1.4 Hz, 2H), 7.44-7.33 (m, 4H), 7.27 (td, J=7.5, 1.4 Hz, 2H), 7.22-6.97 (m, 8H), 3.78 (s, 6H). $^{13}$C NMR (50 MHz, DMSO-d6): δ 169.95, 167.28, 165.48, 159.19, 138.15, 136.69, 133.74, 129.31, 128.36, 127.63, 126.62, 126.32, 120.25, 117.26, 112.78, 55.10. HRMS-ESI (m/z): [M+H]+ calc. for $C_{15}H_{12}BrN_5S^+$, 374.00696; Found: 374.00797. HPLC (km): Purity 100.0%; $t_R$: 11.458 min (method 2).

N2,N2'-(disulfanediylbis(2,1-phenylene))bis(6-(3-ethoxyphenyl)-1,3,5-triazine-2,4-diamine) (MTF-319)

Synthesized following the general procedure B using N—(N-(benzo[d]thiazol-2-yl)carbamimidoyl)-3-ethoxybenzimidamide (339 mg, 1 mmol) to afford the titled compound as a white powder (291 mg, 86%). $^1$H NMR (200 MHz, DMSO-d6): δ 9.24 (s, 2H), 7.83 (d, J=8.8 Hz, 4H), 7.62 (dd, J=7.6, 1.1 Hz, 2H), 7.37 (t, J=7.8 Hz, 4H), 7.32-7.23 (m, 2H), 7.22-7.15 (m, 2H), 7.14-6.98 (m, 6H), 4.04 (q, J=6.9 Hz, 4H), 1.33 (t, J=6.9 Hz, 6H). $^{13}$C NMR (50 MHz, DMSO-d6): δ 169.98, 167.28, 165.48, 158.46, 138.12, 136.73, 133.68, 129.30, 128.39, 127.64, 126.61, 126.29, 120.13, 117.81, 113.27, 63.06, 14.68. HRMS-ESI (m/z): [M+H]$^+$ calc. for $C_{34}H_{33}N_{10}O_2S_2^+$, 677.22239; Found: 677.22253. HPLC ($\lambda_{280}$): Purity 100.0%; $t_R$: 13.058 min (method 2).

N2,N2'-(disulfanediylbis(2,1-phenylene))bis(6-(3-fluorophenyl)-1,3,5-triazine-2,4-diamine (MTF-320)

Synthesized following the general procedure B using N—(N-(benzo[d]thiazol-2-yl)carbamimidoyl)-3-fluorobenzimidamide (313 mg, 1 mmol) to afford the titled compound as a white powder (237 mg, 76%). $^1$H NMR (200 MHz, DMSO-d6): δ 9.32 (s, 2H), 8.08 (d, J=7.6 Hz, 2H), 7.93 (d, J=9.7 Hz, 2H), 7.62 (d, J=7.7 Hz, 2H), 7.57-7.45 (m, 2H), 7.45-7.06 (m, 12H). $^{19}$F NMR (188 MHz, DMSO-d6): δ −113.29. $^{13}$C NMR (50 MHz, DMSO-d6): δ 168.98, 167.26, 165.51, 164.58, 159.75, 139.31 (d, J=7.7 Hz), 136.52, 133.76, 130.39 (d, J=7.8 Hz), 128.22, 127.66, 126.62 (d, J=16.1 Hz), 123.79, 118.23 (d, J=20.5 Hz), 114.11 (d, J=22.6 Hz). HRMS-ESI (m/z): [M+H]$^+$ calc. for $C_{30}H_{23}F_2N_{10}S_2^+$, 625.15112; Found: 625.15125. HPLC ($\lambda_{280}$): Purity 97.5%; $t_R$: 12.817 min (method 2).

N2,N2'-(disulfanediylbis(2,1-phenylene))bis(6-(pyridin-2-yl)-1,3,5-triazine-2,4-diamine) (MTF-321)

Synthesized following the general procedure B using N—(N-(benzo[d]thiazol-2-yl)carbamimidoyl)picolinimidamide (296 mg, 1 mmol) to afford the titled compound as a white powder (266 mg, 90%). $^1$H NMR (200 MHz, DMSO-d6): δ 9.39 (s, 1H), 8.74-8.64 (m, 1H), 8.20 (d, J=7.8 Hz, 1H), 7.93 (td, J=7.7, 1.8 Hz, 1H), 7.61 (dd, J=7.6, 1.5 Hz, 1H), 7.51 (ddd, J=7.5, 4.7, 1.2 Hz, 1H), 7.39 (dd, J=7.7, 1.4 Hz, 1H), 7.35-7.08 (m, 4H). $^{13}$C NMR (50 MHz, DMSO-d6): δ 170.30, 167.53, 165.79, 154.32, 149.29, 136.74, 136.57, 133.61, 128.25, 127.64, 126.88, 126.47, 125.48, 123.33. HRMS-ESI (m/z): [M+H]$^+$ calc. for $C_{28}H_{23}N_{12}S_2^+$, 591.16048; Found: 591.16048. HPLC ($\lambda_{280}$): Purity 95.3%; $t_R$: 6.483 min (method 2).

N2,N2'-(disulfanediylbis(2,1-phenylene))bis(6-(3-chlorophenyl)-1,3,5-triazine-2,4-diamine) (MTF-322)

Synthesized following the general procedure B using N—(N-(benzo[d]thiazol-2-yl)carbamimidoyl)-3-chlorobenzimidamide (329 mg, 1 mmol) to afford the titled compound as a white powder (260 mg, 79%). $^1$H NMR (200 MHz, DMSO-d6): δ 9.33 (s, 2H), 8.24 (s, 2H), 8.16 (d, J=7.6 Hz, 2H), 7.58 (ddd, J=20.7, 9.4, 4.5 Hz, 6H), 7.44-7.08 (m, 10H). $^{13}$C NMR (50 MHz, DMSO-d6): δ 168.82, 167.23, 165.50, 138.80, 136.49, 133.81, 133.18, 131.14, 130.31, 128.22, 127.66, 127.45, 126.79, 126.51, 126.27. HRMS-ESI (m/z): [M+H]$^+$ calc. for $C_{30}H_{23}Cl_2N_{10}S_2^+$, 657.09201; Found: 657.09222. HPLC ($\lambda_{280}$): Purity 96.9%; $t_R$: 12.867 min (method 2).

N2,N2'-(disulfanediylbis(2,1-phenylene))bis(6-(3-bromophenyl)-1,3,5-triazine-2,4-diamine) (MTF-323)

Synthesized following the general procedure B using N—(N-(benzo[d]thiazol-2-yl)carbamimidoyl)-3-bromobenzimidamide (374 mg, 1 mmol) to afford the titled compound as a white powder (339 mg, 91%). $^1$H NMR (200 MHz, DMSO-d6): δ 9.34 (s, 2H), 8.40 (s, 2H), 8.20 (d, J=7.8 Hz, 2H), 7.74 (ddd, J=8.0, 2.0, 1.0 Hz, 2H), 7.62 (dd, J=7.5, 1.6 Hz, 2H), 7.46 (t, J=7.9 Hz, 2H), 7.40-7.13 (m, 10H). $^{13}$C NMR (50 MHz, DMSO-d6): δ 168.73, 167.22, 165.49, 138.97, 136.48, 134.02, 133.83, 130.60, 130.43, 128.22, 127.66, 126.81, 126.63, 126.55, 121.69. HRMS-ESI (m/z): [M+H]$^+$ calc. for $C_{30}H_{23}Br_2N_{10}S_2^+$, 744.99098; Found: 744.99098. HPLC ($\lambda_{280}$): Purity 100.0%; $t_R$: 17.600 min (method 2).

N2,N2'-(disulfanediylbis(2,1-phenylene))bis(6-(4-methoxyphenyl)-1,3,5-triazine-2,4-diamine) (MTF-324)

Synthesized following the general procedure B using N—(N-(benzo[d]thiazol-2-yl)carbamimidoyl)-4-methoxybenzimidamide (325 mg, 1 mmol) to afford the titled compound as a white powder (263 mg, 81%). $^1$H NMR (200 MHz, DMSO-d6): δ 9.13 (s, 2H), 8.20 (d, J=8.8 Hz, 4H), 7.62 (dd, J=7.8, 1.2 Hz, 2H), 7.40 (d, J=7.2 Hz, 2H), 7.32-7.22 (m, 2H), 7.22-7.12 (m, 2H), 7.01 (d, J=8.8 Hz, 8H), 3.82 (s, 6H). $^{13}$C NMR (50 MHz, DMSO-d6): δ 169.77, 167.19, 165.36, 161.99, 136.91, 133.33, 129.62 (2C), 128.90, 128.61, 127.72, 126.36, 126.10, 113.57 (2C), 55.30. HRMS-ESI (m/z): [M+H]$^+$ calc. for $C_{32}H_{29}N_{10}O_2S_2^+$, 649.19109; Found: 649.19116. HPLC ($\lambda_{280}$): Purity 100.0%; $t_R$: 10.800 min (method 2).

3,3'-(((disulfanediylbis(2,1-phenylene))bis(azanediyl))bis(6-amino-1,3,5-triazine-4,2-diyl))dibenzonitrile (MTF-325)

Synthesized following the general procedure B using N—(N-(benzo[d]thiazol-2-yl)carbamimidoyl)-3-cyanobenzimidamide (320 mg, 1 mmol) to afford the titled compound as a white powder (291 mg, 91%). $^1$H NMR (200 MHz, DMSO-d6): δ 9.37 (s, 2H), 8.49 (d, J=10.9 Hz, 4H), 8.02 (d, J=7.7 Hz, 2H), 7.72 (t, J=7.8 Hz, 2H), 7.63 (dd, J=7.6, 1.4 Hz, 2H), 7.42-7.15 (m, 10H). $^{13}$C NMR (50 MHz, DMSO-d6): δ 168.32, 167.24, 165.49, 137.79, 136.48, 134.74, 133.71, 132.16, 131.22, 129.88, 128.38, 127.79, 126.80, 126.59, 118.56, 111.54. HRMS-ESI (m/z): [M+H]$^+$ calc. for C$_{32}$H$_{23}$N$_{12}$S$_2^+$, 639.16046; Found: 639.16064. HPLC (λ$_{280}$): Purity 96.1%; t$_R$: 11.858 min (method 2).

N2,N2'-(disulfanediylbis(2,1-phenylene))bis(6-phenyl-1,3,5-triazine-2,4-diamine) (MTF-326)

Synthesized following the general procedure B using N—(N-(benzo[d]thiazol-2-yl)carbamimidoyl)benzimidamide (295 mg, 1 mmol) to afford the titled compound as a white powder (218 mg, 74%). $^1$H NMR (200 MHz, DMSO-d6): δ 9.23 (s, 2H), 8.24 (d, J=6.5 Hz, 4H), 7.62 (d, J=7.3 Hz, 2H), 7.57-7.34 (m, 8H), 7.33-7.01 (m, 8H). $^{13}$C NMR (50 MHz, DMSO-d6): δ 170.16, 167.29, 165.51, 136.71, 136.61, 133.59, 131.41, 128.37, 128.24 (2C), 127.82 (2C), 127.66, 126.61, 126.31. HRMS-ESI (m/z): [M+H]$^+$ calc. for C$_{30}$H$_{25}$N$_{10}$S$_2^+$, 589.16996; Found: 589.16992. HPLC (λ$_{280}$): Purity 100.0%; t$_R$: 11.792 min (method 2).

N2,N2'-(disulfanediylbis(2,1-phenylene))bis(6-(4-chlorophenyl)-1,3,5-triazine-2,4-diamine) (MTF-327)

Synthesized following the general procedure B using N—(N-(benzo[d]thiazol-2-yl)carbamimidoyl)-4-chlorobenzimidamide (329 mg, 1 mmol) to afford the titled compound as a white powder (283 mg, 86%). $^1$H NMR (200 MHz, DMSO-d6): δ 9.27 (s, 2H), 8.22 (d, J=8.5 Hz, 4H), 7.66-7.50 (m, 6H), 7.38 (dd, J=7.6, 1.0 Hz, 2H), 7.33-7.05 (m, 8H). $^{13}$C NMR (50 MHz, DMSO-d6): δ 169.18, 167.22, 165.46, 136.62, 136.20, 135.47, 133.52, 129.53 (2C), 128.42 (3C), 127.73, 126.65, 126.37. HRMS-ESI (m/z): [M+H]$^+$ calc. for C$_{30}$H$_{23}$O$_2$N$_{10}$S$_2^+$, 657.09201; Found: 657.09210. HPLC (λ$_{280}$): Purity 100.0%; t$_R$: 15.633 min (method 2).

N2,N2'-(disulfanediylbis(2,1-phenylene))bis(6-(4-iodophenyl)-1,3,5-triazine-2,4-diamine) (MTF-328)

Synthesized following the general procedure B using N—(N-(benzo[d]thiazol-2-yl)carbamimidoyl)-4-iodobenzimidamide (421 mg, 1 mmol) to afford the titled compound as a white powder (387 mg, 92%). $^1$H NMR (200 MHz, DMSO-d6): δ 9.26 (s, 2H), 8.00 (d, J=8.4 Hz, 4H), 7.87 (d, J=8.4 Hz, 4H), 7.61 (d, J=7.6 Hz, 2H), 7.39 (d, J=7.4 Hz, 2H), 7.33-6.99 (m, 8H). $^{13}$C NMR (50 MHz, DMSO-d6): δ 169.58, 167.21, 165.45, 137.24 (2C), 136.63, 136.19, 133.49, 129.70 (2C), 128.47, 127.73, 126.61, 126.34, 99.15. HRMS-ESI (m/z): [M+H]$^+$ calc. for C$_{30}$H$_{23}$I$_2$N$_{10}$S$_2^+$, 840.96324; Found: 840.96289. HPLC (λ$_{280}$): Purity 100.0%; t$_R$: 17.833 min (method 2).

N2,N2'-(disulfanediylbis(2,1-phenylene))bis(6-(pyridin-4-yl)-1,3,5-triazine-2,4-diamine) (MTF-329)

Synthesized following the general procedure B using N—(N-(benzo[d]thiazol-2-yl)carbamimidoyl)isonicotinimidamide (296 mg, 1 mmol) to afford the titled compound as a white powder (266 mg, 90%). $^1$H NMR (200 MHz, DMSO-d6): δ 9.41 (s, 2H), 8.73 (dd, J=4.5, 1.5 Hz, 4H), 8.05 (d, J=5.8 Hz, 4H), 7.62 (dd, J=7.4, 1.2 Hz, 2H), 7.43-7.08 (m, 10H). $^{13}$C NMR (50 MHz, DMSO-d6): δ 168.77, 167.33, 165.59, 150.23 (2C), 144.04, 136.41, 133.74, 128.33, 127.75, 126.86, 126.61, 121.55 (2C). HRMS-ESI (m/z): [M+H]$^+$ calc. for C$_{28}$H$_{23}$N$_{12}$S$_2^+$, 591.16046; Found: 591.16089. HPLC (λ$_{280}$): Purity 99.2%; t$_R$: 7.742 min (method 2).

N2,N2'-(disulfanediylbis(2,1-phenylene))bis(6-(pyridin-3-yl)-1,3,5-triazine-2,4-diamine) (MTF-330)

Synthesized following the general procedure B using N—(N-(benzo[d]thiazol-2-yl)carbamimidoyl)nicotinimidamide (296 mg, 1 mmol) to afford the titled compound as a white powder (266 mg, 90%). (277 mg, 94%). $^1$H NMR (200 MHz, DMSO-d6): δ 9.35 (s, 4H), 8.71 (dd, J=4.8, 1.7 Hz, 2H), 8.47 (d, J=8.1 Hz, 2H), 7.62 (dd, J=7.6, 1.2 Hz, 2H), 7.52 (dd, J=7.8, 4.6 Hz, 2H), 7.38 (dd, J=7.7, 1.4 Hz, 2H), 7.33-7.06 (m, 8H $^{13}$C NMR (50 MHz, DMSO-d6): δ 168.81, 167.12, 165.37, 151.99, 149.09, 136.50, 135.09, 133.66, 132.00, 128.31, 127.69, 126.77, 126.49, 123.51 HRMS-ESI (m/z): [M+H]$^+$ calc. for C$_{28}$H$_{23}$N$_{12}$S$_2^+$, 591.16046; Found: 591.16052. HPLC (λ$_{280}$): Purity 100.0%; t$_R$: 7.700 min (method 2).

2-((4-amino-6-(3-bromophenyl)-1,3,5-triazin-2-yl)amino)phenol (MTF-331)

Synthesized following the general procedure A using 1-(benzo[d]oxazol-2-yl)guanidine (1.00 g, 5.68 mmol), sodium hydride (60% dispersion in mineral oil, 1.5 eq., 341 mg, 8.52 mmol) and 3-bromobenzonitrile (1.034 g, 5.68 mmol) to afford the titled compound as a brown powder (1.46 g, 72%). $^1$H NMR (400 MHz, DMSO-d6): δ 9.97 (s, 1H), 8.44 (s, 1H), 8.36 (s, 1H), 8.26 (d, J=7.5 Hz, 1H), 7.90 (d, J=7.7 Hz, 1H), 7.76 (d, J=7.7 Hz, 1H), 7.48 (t, J=7.8 Hz, 1H), 7.29 (s, 2H), 6.99-6.92 (m, 1H), 6.89 (d, J=7.4 Hz, 1H), 6.82 (t, J=7.1 Hz, 1H). $^{13}$C NMR (50 MHz, DMSO-d6): δ 168.84, 167.06, 164.48, 148.30, 138.75, 133.26, 131.22, 130.38, 127.46, 126.84, 126.29, 124.12, 122.65, 118.99, 115.77. HRMS-ESI (m/z): [M+H]$^+$ calc. for C$_{15}$H$_{13}$BrN$_5$O$^+$, 358.02980 Found: 358.03094. HPLC (λ$_{280}$): Purity 97.1%; t$_R$: 9.808 min (method 1).

2-((4-amino-6-(3-chlorophenyl)-1,3,5-triazin-2-yl)amino)phenol (MTF-332)

Synthesized following the general procedure A using 1-(benzo[d]oxazol-2-yl)guanidine (1.00 g, 5.68 mmol), sodium hydride (60% dispersion in mineral oil, 1.5 eq., 341 mg, 8.52 mmol) and 3-chlorobenzonitrile (781 mg, 5.68 mmol) to afford the titled compound as a brown powder (1.45 g, 82%). $^1$H NMR (400 MHz, DMSO-d6): δ 10.03 (s, 1H), 8.36 (s, 1H), 8.29 (s, 1H), 8.23 (d, J=7.4 Hz, 1H), 7.92 (d, J=7.5 Hz, 1H), 7.62 (d, J=7.5 Hz, 1H), 7.55 (t, J=7.8 Hz, 1H), 7.29 (s, 2H), 6.99-6.92 (m, 1H), 6.89 (d, J=7.3 Hz, 1H), 6.82 (t, J=7.1 Hz, 1H). $^{13}$C NMR (50 MHz, DMSO-d6): δ 168.74, 167.02, 164.48, 148.21, 138.90, 134.11, 130.67, 130.40, 126.66 (2C), 124.17, 122.79, 121.73, 119.10, 115.78. HRMS-ESI (m/z): [M+H]$^+$ calc. for C$_{15}$H$_{13}$ClN$_5$O$^+$, 314.08031; Found: 314.08066. HPLC (λ$_{280}$): Purity 97.3%; t$_R$: 9.625 min (method 1).

N2,N2'-(disulfanediylbis(2,1-phenylene))bis(6-benzyl-1,3,5-triazine-2,4-diamine (MTF-333)

In a microwave tube, 1-(benzo[d]thiazol-2-yl)guanidine (100 mg, 0.52 mmol) was solubilized in NMP (2 mL) under argon atmosphere. The tube was subsequently cooled down to 0° C. before NaH (60% suspension in oil, 23 mg, 0.57 mmol) was added. After the gas evolution stopped, the tube was sealed and the mixture was warmed up to 110° C. under microwave irradiation for 15 min. The resulting slurry was taken in Et$_2$O and filtered. The precipitate was then purified by silicagel flash chromatography (dichloromethane/MeOH, 10/0 to 9/1) to give the desired product as a white powder (50 mg, 31%). TLC: R$_f$ (dichloromethane/MeOH, 9/1, v/v) =0.83. $^1$H NMR (400 MHz, DMSO-d6): δ 9.05 (s, 1H), 7.54 (dd, J=7.8, 0.9 Hz, 1H), 7.35-7.17 (m, 7H), 7.14 (t, J=7.7 Hz, 1H), 6.95 (d, J=16.0 Hz, 2H), 3.71 (s, 2H). $^{13}$C NMR (101 MHz, DMSO-d6): δ 176.6, 166.9, 165.3, 151.5, 139.2, 137.9, 136.6, 129.1, 128.2, 128.0, 127.6, 126.3, 124.9, 30.4. HRMS-ESI (m/z): [M+H]$^+$ calc. for C$_{32}$H$_{29}$N$_{10}$S$_2^+$ 617.20126, found 617.20154. HPLC (λ$_{254}$): Purity 96.2%; t$_R$: 10.742 min (method 2).

N—(N-(benzo[d]thiazol-2-yl)carbamimidoyl)-3-methoxybenzimidamide (MTF-342)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-methoxybenzonitrile (0.635 mL, 5.20 mmol) to afford the titled compound as a white powder (914 mg, 54%). $^1$H NMR (200 MHz, DMSO-d6): δ 10.26 (s, 1H), 9.33 (s, 1H), 8.82 (s, 1H), 8.05 (s, 1H), 7.80 (d, J=7.6 Hz, 1H), 7.73-7.52 (m, 3H), 7.48-7.29 (m, 2H), 7.17 (dd, J=14.6, 7.6 Hz, 2H), 3.83 (s, 3H). $^{13}$C NMR spectrum could not be properly recorded as this compound rearranges and dimerizes into compound MTF-318 during the time of the analysis. HRMS-ESI (m/z): [M+H]$^+$ calc. for C$_{16}$H$_{16}$N$_5$OS$^+$, 326.10701; Found: 326.10706. HPLC (λ$_{280}$): Purity 100.0%; t$_R$: 6.558 min (method 1).

N—(N-(benzo[d]thiazol-2-yl)carbamimidoyl)-3-(trifluoromethyl)benzimidamide (MTF-343)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-(trifluoromethyl)benzonitrile (890 mg, 5.20 mmol) to afford the titled compound as a white powder (435 mg, 23%). $^1$H NMR (200 MHz, DMSO-d6): δ 10.33 (br. s, 1H), 9.36 (br. s, 1H), 8.93 (br. s, 1H), 8.39 (s, 1H), 8.31 (d, J=7.9 Hz, 1H), 8.16 (br. s, 1H), 7.95 (d, J=7.9 Hz, 1H), 7.86-7.72 (m, 2H), 7.67 (d, J=8.0 Hz, 1H), 7.35 (t, J=7.6 Hz, 1H), 7.20 (t, J=7.5 Hz, 1H). $^{19}$F NMR (376 MHz, DMSO-d6): δ −61.04. $^{13}$C NMR spectrum could not be properly recorded as this compound rearranges and dimerizes during the time of the analysis. HRMS-ESI (m/z): [M+H]$^+$ calc. for C$_{16}$H$_{13}$F$_3$N$_5$S$^+$, 364.08383; Found: 364.08408. HPLC (λ$_{280}$): Purity 97.9%; t$_R$: 6.533 min (method 1).

N—(N-(benzo[d]thiazol-2-yl)carbamimidoyl)-3-ethoxybenzimidamide (MTF-344)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-ethoxybenzonitrile (765 mg, 5.20 mmol) to afford the titled compound as a white powder (830 mg, 47%). $^1$H NMR (200 MHz, DMSO-d6): δ 10.23 (br. s, 1H), 9.30 (br. s, 1H), 8.78 (br. s, 1H), 8.03 (br. s, 1H), 7.80 (dd, J=7.8, 0.8 Hz, 1H), 7.65 (dd, J=8.0, 0.6 Hz, 1H), 7.62-7.53 (m, 2H), 7.46-7.29 (m, 2H), 7.24-7.07 (m, 2H), 4.09 (q, J=6.9 Hz, 2H), 1.36 (t, J=6.9 Hz, 3H). $^{13}$C NMR (50 MHz, DMSO-d6): δ 172.24, 162.07, 161.82, 158.40, 151.49, 136.56, 131.16, 129.36, 125.63, 122.78, 121.13, 119.68, 119.65, 117.34, 113.64, 63.24, 14.63. HRMS-ESI (m/z): [M+H]$^+$ calc. for C$_{17}$H$_{18}$N$_5$OS$^+$, 340.12266; Found: 340.12296. HPLC (λ$_{280}$): Purity 100.0%; t$_R$: 6.733 min (method 1).

N—(N-(benzo[d]thiazol-2-yl)carbamimidoyl)pyrazine-2-carboximidamide (MTF-345)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and pyrazinecarbonitrile (0.465 mL, 5.20 mmol) to afford the titled compound as a yellow powder (959 mg, 62%). $^1$H NMR (200 MHz, DMSO-d6): δ 10.13 (br. s, 1H), 9.50 (s, 1H), 9.44 (br. s, 1H), 8.99 (br. s, 1H), 8.88 (d, J=2.5 Hz, 1H), 8.79 (dd, J=2.5, 1.4 Hz, 1H), 8.26 (br. s, 1H), 7.83 (d, J=7.7 Hz, 1H), 7.69 (d, J=7.9 Hz, 1H), 7.44-7.30 (m, 1H), 7.29-7.15 (m, 1H). $^{13}$C NMR (50 MHz, DMSO-d6): δ 172.18, 161.92, 157.68, 151.39, 147.21, 145.85, 143.84, 143.44, 131.22, 125.73, 123.01, 121.22, 119.90. HRMS-ESI (m/z): [M+H]$^+$ calc. for C$_{13}$H$_{12}$N$_7$S$^+$, 298.08694; Found: 298.08707. HPLC (λ$_{280}$): Purity 95.7%; t$_R$: 5.508 min (method 1).

N—(N-(benzo[d]thiazol-2-yl)carbamimidoyl)-3-fluorobenzimidamide (MTF-346)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3-fluorobenzonitrile (0.56 mL, 5.20 mmol) to afford the titled compound as a white powder (895 mg, 55%). $^1$H NMR (200 MHz, DMSO-d6): δ 10.26 (s, 1H), 9.34 (s, 1H), 8.89 (s, 1H), 8.09 (s, 1H), 7.95-7.76 (m, 3H), 7.70-7.51 (m, 2H), 7.50-7.28 (m, 2H), 7.19 (td, J=7.6, 1.2 Hz, 1H). $^{19}$F NMR (376 MHz, DMSO-d6): δ −112.99. $^{13}$C NMR spectrum could not be properly recorded as this compound rearranges and dimerizes into compound MTF-320 during the time of the analysis. HRMS-ESI (m/z): [M+H]$^+$ calc. for C$_{15}$H$_{13}$FN$_5$S$^+$, 314.08702; Found: 314.08722. HPLC (λ$_{280}$): Purity 98.7%; t$_R$: 6.442 min (method 1).

N—(N-(benzo[d]thiazol-2-yl)carbamimidoyl)-3-cyanobenzimidamide (MTF-347)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 1,3-dicyanobenzene (667 mg, 5.20 mmol) to afford the titled compound as a white-yellowish powder (1.23 g, 74%). $^1$H NMR (200 MHz, DMSO-d6): δ 10.27 (br. s, 1H), 9.37 (br. s, 1H), 8.97 (br. s, 1H), 8.45 (s, 1H), 8.33 (dd, J=8.0, 1.0 Hz, 1H), 8.15 (br. s, 1H), 8.06 (dd, J=7.7, 1.0 Hz, 1H), 7.89-7.62 (m, 3H), 7.35 (t, J=7.6 Hz, 1H), 7.20 (t, J=7.5 Hz, 1H). $^{13}$C NMR (50 MHz, DMSO-d6): δ 172.17, 161.83, 159.93, 151.42, 136.30, 134.69, 132.15, 131.40, 131.24, 129.67, 125.67, 122.89, 121.17, 119.81, 118.39, 111.50. HRMS-ESI (m/z): [M+H]$^+$ calc. for C$_{16}$H$_{13}$N$_6$S$^+$, 321.09169; Found: 321.09167. HPLC (λ$_{280}$): Purity 96.4%; t$_R$: 6.342 min (method 1).

N2,N2'-(disulfanediylbis(2,1-phenylene))bis(6-(pyrazin-2-yl)-1,3,5-triazine-2,4-diamine) (MTF-348)

Synthesized following the general procedure B using N—(N-(benzo[d]thiazol-2-yl)carbamimidoyl)pyrazine-2- carboximidamide (297 mg, 1 mmol) to afford the titled compound as a yellowish powder (279 mg, 94%). $^1$H NMR (400 MHz, DMSO-d6): δ 9.48 (br. s, 1H), 9.33 (br. s, 1H), 8.77 (m, 2H), 7.61 (d, J=7.7 Hz, 1H), 7.38 (d, J=6.7 Hz, 2H), 7.23 (m, 3H). $^{13}$C NMR (50 MHz, DMSO-d6): δ 168.83, 167.37, 165.65, 149.51, 146.27, 144.58, 144.38, 136.35, 133.76, 128.18, 127.66, 127.06, 126.68. HRMS-ESI (m/z): [M+H]$^+$ calc. for $C_{28}H_{23}N_{12}S_2^+$, 591.16046; Found: 591.16052. HPLC ($\lambda_{280}$): Purity 99.2%; $t_R$: 8.875 min (method 2).

N—(N-(benzo[d]thiazol-2-yl)carbamimidoyl)-6-chloronicotinimidamide (MTF-379)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 6-chloro-3-pyridinecarbonitrile (720 mg, 5.20 mmol) to afford the titled compound as a beige powder (1.48 g, 86%). $^1$H NMR (400 MHz, DMSO-d6): δ 10.21 (s, 1H), 9.37 (s, 1H), 9.01 (d and br. s, J=2.1 Hz, 2H), 8.38 (dd, J=8.4, 2.3 Hz, 1H), 8.12 (s, 1H), 7.80 (d, J=7.8 Hz, 1H), 7.69 (d, J=8.4 Hz, 1H), 7.66 (d, J=8.1 Hz, 1H), 7.34 (t, J=7.6 Hz, 1H), 7.19 (t, J=7.5 Hz, 1H). $^{13}$C NMR (101 MHz, DMSO-d6): δ 172.16, 161.79, 159.12, 152.70, 151.42, 149.28, 138.70, 131.29, 130.36, 125.68, 123.98, 122.91, 121.17, 119.83. HPLC ($\lambda_{280}$): Purity 97.2%; $t_R$: 7.033 min (method 1).

N—(N-(benzo[d]thiazol-2-yl)carbamimidoyl)-2-chloroisonicotinimidamide (MTF-380)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2-chloro-4-pyridinecarbonitrile (720 mg, 5.20 mmol) to afford the titled compound as a beige powder (327 mg, 19%). $^1$H NMR (400 MHz, DMSO-d6): δ 10.22 (br. s, 1H), 9.39 (br. s, 1H), 9.04 (br. s, 1H), 8.60 (d, J=5.1 Hz, 1H), 8.21 (br. s, 1H), 8.05 (s, 1H), 7.94 (dd, J=5.2, 1.3 Hz, 1H), 7.81 (d, J=7.3 Hz, 1H), 7.67 (d, J=7.9 Hz, 1H), 7.38-7.31 (m, 1H), 7.24-7.17 (m, 1H). $^{13}$C NMR (101 MHz, DMSO-d6): δ 172.08, 161.68, 158.50, 151.36, 150.84, 150.52, 146.10, 131.31, 125.70, 122.99, 122.27, 121.20, 120.99, 119.90. HPLC ($\lambda_{280}$): Purity 97.8%; $t_R$: 7.108 min (method 1).

N—(N-(benzo[d]thiazol-2-yl)carbamimidoyl)thiophene-2-carboximidamide (MTF-381)

Synthesized following the general procedure 1-(benzo[d]thiazol-2-yl)guanidine (1.00 g, 5.20 mmol), sodium hydride (60% dispersion in mineral oil, 1.5 eq., 312 mg, 7.81 mmol) and 2-thiophenecarbonitrile (0.48 mL, 5.20 mmol) to afford the titled compound as a yellowish powder (815 mg, 52%). $^1$H NMR (400 MHz, DMSO-d6): δ 10.22 (br. s, 1H), 9.34 (br. s, 1H), 8.88 (br. s, 1H), 7.94 (dd, J=3.7, 0.9 Hz, 2H), 7.79 (d, J=6.2 Hz, 2H), 7.65 (d, J=7.9 Hz, 1H), 7.39-7.28 (m, 1H), 7.24-7.14 (m, 2H). $^{13}$C NMR (101 MHz, DMSO-d6): δ 172.22, 161.71, 157.31, 151.46, 140.40, 131.89, 131.13, 128.97, 128.11, 125.65, 122.79, 121.12, 119.68. HPLC ($\lambda_{280}$): Purity 99.2%; $t_R$: 6.975 min (method 1).

N—(N-(benzo[d]thiazol-2-yl)carbamimidoyl)-3,4,5-trimethoxybenzimidamide (MTF-382)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3,4,5-trimethoxybenzonitrile (1 g, 5.20 mmol) to afford the titled compound as a beige powder (441 mg, 22%). $^1$H NMR (200 MHz, DMSO-d6): δ 10.22 (br. s, 1H), 9.29 (br. s, 1H), 8.77 (br. s, 1H), 8.01 (br. s, 1H), 7.80 (d, J=7.0 Hz, 1H), 7.65 (d, J=7.5 Hz, 1H), 7.39 (s, 2H), 7.38-7.27 (m, 1H), 7.19 (td, J=7.7, 1.1 Hz, 1H), 3.87 (s, 6H), 3.74 (s, 3H). $^{13}$C NMR (50 MHz, DMSO-d6): δ 172.28, 161.97, 161.53, 152.51 (2C), 151.54, 140.27, 131.19, 130.33, 125.63, 122.75, 121.12, 119.66, 105.29 (2C), 60.14, 56.06 (2C). HPLC ($\lambda_{280}$): Purity 96.1%; $t_R$: 7.175 min (method 1).

N—(N-(benzo[d]thiazol-2-yl)carbamimidoyl)benzo[d][1,3]dioxole-5-carboximidamide (MTF-383)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and piperonylonitrile (765 mg, 5.20 mmol) to afford the titled compound as a beige powder (600 mg, 34%). $^1$H NMR (400 MHz, DMSO-d6): δ 10.27 (s, 1H), 9.29 (s, 1H), 8.68 (s, 1H), 7.95 (s, 1H), 7.79 (d, J=7.7 Hz, 1H), 7.68-7.62 (m, 2H), 7.60 (d, J=1.6 Hz, 1H), 7.37-7.29 (m, 1H), 7.22-7.15 (m, 1H), 7.04 (d, J=8.2 Hz, 1H), 6.13 (s, 2H). $^{13}$C NMR (50 MHz, DMSO-d6): δ 172.25, 161.95, 161.27, 151.52, 150.06, 147.38, 131.13, 128.99, 125.62, 122.74, 122.56, 121.11, 119.65, 107.85, 107.61, 101.80. HPLC ($\lambda_{280}$): Purity 96.0%; $t_R$: 7.133 min (method 1).

N—(N-(benzo[d]thiazol-2-yl)carbamimidoyl)-2-naphthimidamide (MTF-384)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and naphthalene-2-carbonitrile (796 mg, 5.20 mmol) to afford the titled compound as a beige powder (1.04 g, 58%). $^1$H NMR (400 MHz, DMSO-d6): δ 10.38 (br. s, 1H), 9.42 (br. s, 1H), 8.99 (br. s, 1H), 8.64 (s, 1H), 8.16 (br. s and dd, J=8.6, 1.4 Hz, 2H), 8.08-7.96 (m, 3H), 7.81 (d, J=7.7 Hz, 1H), 7.67 (d, J=7.9 Hz, 1H), 7.66-7.57 (m, 2H), 7.40-7.31 (m, 1H), 7.25-7.15 (m, 1H). $^{13}$C NMR (50 MHz, DMSO-d6): δ 172.34, 162.16 (2C), 151.53, 134.30, 132.66, 132.15, 131.22, 128.83, 127.84, 127.75 (2C), 127.66, 126.80, 125.65, 124.55, 122.81, 121.14, 119.73. HPLC ($\lambda_{280}$): Purity 95.7%; $t_R$: 7.392 min (method 1).

N—(N-(benzo[d]thiazol-2-yl)carbamimidoyl)-4-(trifluoromethyl)benzimidamide (MTF-385)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-(trifluoromethyl)benzonitrile (889 mg, 5.20 mmol) to afford the titled compound as a beige powder (1.38 g, 73%). $^1$H NMR (400 MHz, DMSO-d6): δ 10.28 (br. s, 1H), 9.38 (br. s, 1H), 8.97 (br. s, 1H), 8.22 (d, J=8.2 Hz, 2H), 8.11 (br. s, 1H), 7.90 (d, J=8.3 Hz, 2H), 7.80 (d, J=7.3 Hz, 1H), 7.67 (d, J=7.7 Hz, 1H), 7.39-7.30 (m, 1H), 7.24-7.16 (m, 1H). $^{19}$F NMR (377 MHz, DMSO-d6): δ −61.28. $^{13}$C NMR (50 MHz, DMSO-d6): δ 172.11, 161.89, 160.69, 151.37, 139.09, 131.19, 131.40 (q, J=31.8 Hz), 128.36 (2C), 125.57, 125.16 (q, J=3.8 Hz, 2C), 123.91 (q, J=67.7 Hz), 122.79, 121.07, 119.72. HPLC ($\lambda_{280}$): Purity 96.4%; $t_R$: 7.442 min (method 1).

N—(N-(benzo[d]thiazol-2-yl)carbamimidoyl)-2-bromoisonicotinimidamide (MTF-386)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2-bromo-4-cyanopyridine (952 mg, 5.20 mmol) to afford the titled compound as a yellow powder (859 mg, 44%). $^1$H NMR (400 MHz, DMSO-d6): δ 10.19 (br. s, 1H), 9.38 (br. s, 1H), 9.04 (br. s, 1H), 8.58 (d, J=5.1 Hz, 1H), 8.18 (s and br. s, 2H), 7.96 (dd, J=5.1, 1.3 Hz, 1H), 7.81 (d, J=7.4 Hz, 1H), 7.67 (d, J=7.9 Hz, 1H), 7.39-7.32 (m, 1H), 7.24-7.17 (m, 1H). $^{13}$C NMR (50 MHz, DMSO-d6): δ 172.08, 161.67, 158.42, 151.36, 151.00, 145.67, 141.81, 131.32, 125.94, 125.71, 123.00, 121.25, 121.21, 119.91. HPLC ($\lambda_{280}$): Purity 97.0%; $t_R$: 7.192 min (method 1).

N—(N-(benzo[d]thiazol-2-yl)carbamimidoyl)-4-bromothiophene-3-carboximidamide (MTF-387)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-bromothiophene-3-carbonitrile (978 mg, 5.20 mmol) to afford the titled compound as a brown powder (969 mg, 49%). $^1$H NMR (400 MHz, DMSO-d6): δ 10.03 (br. s, 1H), 9.30 (br. s, 1H), 8.60 (br. s, 1H), 7.98 (br.s and d, J=3.4 Hz, 2H), 7.80 (d, J=7.7 Hz, 1H), 7.77 (d, J=3.4 Hz, 1H), 7.64 (d, J=8.0 Hz, 1H), 7.38-7.30 (m, 1H), 7.20 (d, J=7.3 Hz, 1H). $^{13}$C NMR (50 MHz, DMSO-d6): δ 172.41, 161.84, 159.08, 151.48, 137.36, 131.24, 129.06, 125.66, 125.44, 122.85, 121.16, 119.75, 108.70. HPLC ($\lambda_{280}$): Purity 96.6%; $t_R$: 6.967 min (method 1).

N—(N-(benzo[d]thiazol-2-yl)carbamimidoyl)-2,2-dimethyl-2H-chromene-6-carboximidamide (MTF-388)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 2,2-dimethyl-2H-1-benzopyran-6-carbonitrile (963 mg, 5.20 mmol) to afford the titled compound as a beige powder (118 mg, 6%). $^1$H NMR (400 MHz, DMSO-d6): δ 10.25 (br. s, 1H), 9.29 (br. s, 1H), 8.66 (br. s, 1H), 7.91 (br. s, 1H), 7.84-7.75 (m, 3H), 7.64 (d, J=7.8 Hz, 1H), 7.37-7.30 (m, 1H), 7.22-7.15 (m, 1H), 6.85 (d, J=8.5 Hz, 1H), 6.45 (d, J=9.9 Hz, 1H), 5.84 (d, J=9.8 Hz, 1H), 1.41 (s, 6H). $^{13}$C NMR (101 MHz, DMSO-d6): δ 169.68, 167.16, 165.32, 155.42, 136.88, 133.37, 131.25, 129.27, 129.18, 128.53, 127.69, 126.40, 126.16, 126.10, 121.61, 120.27, 115.66, 76.97, 27.93 (2C). HPLC ($\lambda_{280}$): Purity 98.4%; $t_R$: 7.492 min (method 1).

N—(N-(benzo[d]thiazol-2-yl)carbamimidoyl)-3,5-dichloropicolinimidamide (MTF-389)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 3,5-dichloropyridine-2-carbonitrile (900 mg, 5.20 mmol) to afford the titled compound as a brown powder (779 mg, 41%). $^1$H NMR (400 MHz, DMSO-d6): δ 9.73 (br. s, 1H), 9.29 (br. s, 1H), 8.73 (br. s, 1H), 8.67 (d, J=1.5 Hz, 1H), 8.37 (s, 1H), 8.12 (br. s, 1H), 7.77 (d, J=7.7 Hz, 1H), 7.62 (d, J=7.9 Hz, 1H), 7.32 (t, J=7.5 Hz, 1H), 7.18 (t, J=7.5 Hz, 1H). $^{13}$C NMR (50 MHz, DMSO-d6): δ 172.48, 161.60, 160.60, 151.43, 150.95, 145.79, 137.15, 131.46, 131.19, 129.02, 125.59, 122.77, 121.12, 119.67. HPLC ($\lambda_{280}$): Purity 95.3%; $t_R$: 7.192 min (method 1).

N2,N2'-(disulfanediylbis(2,1-phenylene))bis(6-(4-(trifluoromethyl)phenyl)-1,3,5-triazine-2,4-diamine) (MTF-394)

Synthesized following the general procedure B using N—(N-(benzo[d]thiazol-2-yl)carbamimidoyl)-4-(trifluoromethyl)benzimidamide (363 mg, 1 mmol) to afford the titled compound as a white powder (239 mg, 66%). $^1$H NMR (400 MHz, DMSO-d6): δ 9.34 (s, 1H), 8.42 (d, J=7.8 Hz, 2H), 7.86 (d, J=8.4 Hz, 2H), 7.64 (d, J=7.7 Hz, 1H), 7.41 (d, J=7.4 Hz, 1H), 7.25 (ddd, J=34.2, 11.4, 4.1 Hz, 4H). $^{19}$F NMR (377 MHz, DMSO-d6): δ −61.24. $^{13}$C NMR (101 MHz, DMSO-d6): δ 168.98, 167.28, 165.53, 140.54, 136.56, 133.57, 131.18, 128.46 (2C), 127.76, 126.75, 126.48, 125.50, 125.30 (2C), 122.80. HPLC ($\lambda_{254}$): Purity 97.0%; $t_R$: 16.125 min (method 2).

N2,N2'-(disulfanediylbis(2,1-phenylene))bis(6-(thiophen-2-yl)-1,3,5-triazine-2,4-diamine) (MTF-396)

Synthesized following the general procedure B using N—(N-(benzo[d]thiazol-2-yl)carbamimidoyl)thiophene-2-carboximidamide (301 mg, 1 mmol) to afford the titled compound as a white powder (250 mg, 83%). $^1$H NMR (400 MHz, DMSO-d6): δ 9.21 (s, 1H), 7.84 (d, J=2.9 Hz, 1H), 7.75 (dd, J=5.0, 1.1 Hz, 1H), 7.61 (dd, J=7.9, 1.1 Hz, 1H), 7.37 (d, J=7.4 Hz, 1H), 7.26 (td, J=7.7, 1.2 Hz, 1H), 7.21-7.16 (m, 2H), 7.09 (d, J=15.2 Hz, 2H). $^{13}$C NMR (101 MHz, DMSO-d6): δ 166.91, 166.58, 165.13, 142.40, 136.55, 133.67, 131.03, 129.34, 128.37, 128.08, 127.60, 126.68, 126.35. HPLC ($\lambda_{280}$): Purity 97.1%; $t_R$: 11.817 min (method 2).

N2,N2'-(disulfanediylbis(2,1-phenylene))bis(6-(4-bromothiophen-3-yl)-1,3,5-triazine-2,4-diamine) (MTF-397)

Synthesized following the general procedure B using N—(N-(benzo[d]thiazol-2-yl)carbamimidoyl)-4-bromothiophene-3-carboximidamide (380 mg, 1 mmol) to afford the titled compound as a white powder (167 mg, 44%). $^1$H NMR (400 MHz, DMSO-d6): δ 9.14 (s, 1H), 8.11 (d, J=3.6 Hz, 1H), 7.73 (d, J=3.6 Hz, 1H), 7.57 (d, J=7.3 Hz, 1H), 7.42 (d, J=7.7 Hz, 1H), 7.28-7.22 (m, 1H), 7.12 (t, J=7.4 Hz, 1H), 7.07 (s, 2H). $^{13}$C NMR (101 MHz, DMSO-d6): δ 167.68, 166.88, 165.20, 137.92, 136.60, 133.26, 130.88, 128.44, 127.69, 126.98, 126.29, 126.03, 109.03. HPLC ($\lambda_{254}$): Purity 97.1%; $t_R$: 12.483 min (method 2).

N—(N-(benzo[d]thiazol-2-yl)carbamimidoyl)-4-nitrobenzimidamide (MTF-398)

Synthesized following the general procedure A using 1-(benzo[d]thiazol-2-yl)guanidine (1.00 g, 5.20 mmol), sodium hydride (60% dispersion in mineral oil, 1.5 eq., 312 mg, 7.81 mmol) and 4-nitrobenzonitrile (770 mg, 5.20 mmol) to afford the titled compound as a yellow powder (212 mg, 12%). $^1$H NMR (500 MHz, DMSO-d6): δ 10.30 (br. s, 1H), 9.37 (br. s, 1H), 8.90 (br. s, 1H), 8.12 (t, br. s, J=1.8 Hz, 2H), 7.99 (d, J=7.9 Hz, 1H), 7.80 (d, J=7.7 Hz, 1H), 7.66 (d, J=7.9 Hz, 1H), 7.65-7.60 (m, 1H), 7.54 (t, J=7.9 Hz, 1H), 7.38-7.30 (m, 1H), 7.22-7.17 (m, 1H). $^{13}$C NMR (50 MHz, DMSO-d6): δ 172.22, 161.95, 160.57, 151.47, 137.26, 133.22, 131.23, 131.20, 130.20, 127.53, 126.14, 125.67, 122.87, 121.16, 119.79. HPLC ($\lambda_{280}$): Purity 99.2%; $t_R$: 6.792 min (method 1).

2-((4-amino-6-(trichloromethyl)-1,3,5-triazin-2-yl) amino)phenol (MTF373)

Synthesized following the general procedure D using 1-(benzo[d]oxazol-2-yl)guanidine (100 mg, 0.6 mmol) and trichloroacetonitrile (600 μL, 6 mmol) to afford the title compound as a beige powder (61 mg, 32%). $^1$H NMR (400 MHz, Acetone-d6): δ 9.10 (s, 1H), 8.38 (br. s, 1H), 7.99 (br. s, 1H), 7.28 (br. s, 1H), 7.15 (br. s, 1H), 7.05-6.92 (m, 2H), 6.87 (td, J=7.8, 1.7 Hz, 1H). $^{13}$C NMR (101 MHz, Acetone-d6): δ 174.0, 168.9, 165.8, 148.6, 127.6, 125.6, 123.2, 120.8, 117.2, 97.4. HRMS-ESI (m/z): [M+H]$^+$ calc. for $C_{10}H_9ON_5Cl_3$$^+$319.98672; Found 319.98709. HPLC ($\lambda_{254}$): 97.9%; $t_R$: 9.108 min (method 4).

2-((4-amino-6-(trichloromethyl)-1,3,5-triazin-2-yl) amino)-4-chlorophenol (MTF374)

Synthesized following the general procedure D using 2-(5-chlorobenzo[d]oxazol-2-yl)guanidine (100 mg, 0.48 mmol) and trichloroacetonitrile (450 μL, 4.8 mmol) to afford the title compound as a light pink powder (55 mg, 32%). $^1$H NMR (400 MHz, Acetone-d6): δ 9.48 (s, 1H), 8.30 (s, 1H), 8.18 (s, 1H), 7.43 (s, 1H), 7.20 (s, 1H), 7.01-6.92 (m, 2H). $^{13}$C NMR (101 MHz, Acetone-d6): δ 174.0, 168.9, 165.6, 146.6, 128.8, 124.9, 124.3, 121.9, 117.3, 97.3. HRMS-ESI (m/z): [M+H]$^+$ calc. for $C_{10}H_8ON_5Cl_4$$^+$353.94775; Found 353.94830. HPLC ($\lambda_{254}$): 97.1%; $t_R$: 10.504 min (method 4).

2-(4-amino-6-(trichloromethyl)-1,3,5-triazin-2-yl) amino)-5-chlorophenol (MTF375)

Synthesized following the general procedure D using 2-(6-chlorobenzo[d]oxazol-2-yl)guanidine (100 mg, 0.48 mmol) and trichloroacetonitrile (480 μL, 4.8 mmol) to afford the title compound as a light green powder (59 mg, 35%). $^1$H NMR (400 MHz, Acetone-d6): δ 9.66 (br. s, 1H), 8.32 (br. s, 1H), 8.04 (br. s, 1H), 7.29 (br. s, 1H), 7.18 (br. s, 1H), 6.99 (d, J=2.2 Hz, 1H), 6.90 (dd, J=8.7, 2.1 Hz, 1H). $^{13}$C NMR (101 MHz, Acetone-d6): δ 174.0, 168.9, 165.7, 149.5, 129.5, 126.7, 124.1, 120.4, 116.8, 97.3. HRMS-ESI (m/z): [M+H]$^+$ calc. for $C_{10}H_8ON_5Cl_4$$^+$353.94775; Found 353.94837. HPLC ($\lambda_{254}$): 95.3%; $t_R$: 10.615 min (method 4).

2-((4-amino-6-(trichloromethyl)-1,3,5-triazin-2-yl) amino)-5-nitrophenol (MTF376)

Synthesized following the general procedure D using 2-(6-nitrobenzo[d]oxazol-2-yl)guanidine (100 mg, 0.45 mmol) and trichloroacetonitrile (450 μL, 4.5 mmol) to afford the title compound as a light yellow powder (50 mg, 30%). $^1$H NMR (400 MHz, MeOD): δ 8.72 (d, J=9.1 Hz, 1H), 7.78 (dd, J=9.1, 2.5 Hz, 1H), 7.70 (d, J=2.5 Hz, 1H). $^{13}$C NMR (101 MHz, Acetone-d6): δ 174.3, 169.1, 165.7, 147.1, 143.7, 134.5, 120.3, 116.6, 110.4, 97.1. HRMS-ESI (m/z): [M+H]$^+$ calc. for $C_{10}H_8O_3N_6Cl_3$$^+$ 364.97180; Found 364.97208. HPLC ($\lambda_{254}$): 95.1%; $t_R$: 10.623 min (method 4).

2-((4-amino-6-(trichloromethyl)-1,3,5-triazin-2-yl) amino)-4-nitrophenol (MTF377)

Synthesized following the general procedure D using 2-(5-nitrobenzo[d]oxazol-2-yl)guanidine (100 mg, 0.45 mmol) and trichloroacetonitrile (450 μL, 4.5 mmol) to afford the title compound as a light orange powder (117 mg, 71%). $^1$H NMR (400 MHz, Acetone-d6): δ 9.29 (br. s, 1H), 8.32 (br. s, 1H), 7.91 (dd, J=8.9, 2.6 Hz, 1H), 7.54 (br. s, 1H), 7.23 (br. s, 1H), 7.11 (d, J=8.9 Hz, 1H), 6.61 (br. s, 1H). $^{13}$C NMR (101 MHz, Acetone-d6): δ 174.3, 168.9, 165.6, 146.9, 143.6, 134.3, 120.3, 116.7, 110.3, 97.1. HRMS-ESI (m/z): [M+H]$^+$ calc. for $C_{10}H_8O_3N_6Cl_3$$^+$364.97180; Found 364.97229. HPLC ($\lambda_{254}$): 97.7%; $t_R$: 9.434 min (method 4).

2-((4-amino-6-phenyl-1,3,5-triazin-2-yl)amino)-4-chlorophenol (MTF409)

Synthesized following the general procedure E using 1-(5-chlorobenzo[d]oxazol-2-yl)guanidine (500 mg, 2.4 mmol), sodium hydride (60% oil suspension, 104 mg, 2.6 mmol) and benzonitrile (0.25 mL, 2.4 mmol) to afford the title compound as a beige powder (210 mg, 28%). $^1$H NMR (400 MHz, Acetone-d6): δ 9.88 (br. s, 1H), 8.41-8.37 (m, 2H), 8.16 (s, 2H), 7.56 (t, J=7.2 Hz, 1H), 7.50 (t, J=7.3 Hz, 2H), 7.01-6.92 (m, 2H), 6.81 (br. s, 2H). $^{13}$C NMR (101 MHz, Acetone-d6): δ 172.1, 168.6, 165.7, 147.0, 137.3, 132.6, 129.9, 129.1 (2C), 129.0 (2C), 124.8, 124.1, 121.9, 118.4. HRMS-ESI (m/z): [M+H]$^+$ calc. for $C_{15}H_{13}OClN_5$$^+$ 314.08031; Found 314.08044. HPLC ($\lambda_{254}$): 98.1%; $t_R$: 9.916 min (method 4).

2-((6-imino-4-(trichloromethyl)-1,6-dihydro-1,3,5-triazin-2-yl)amino)-5-methylphenol (MTF410)

Synthesized following the general procedure D using 1-(6-methylbenzo[d]oxazol-2-yl)guanidine (500 mg, 2.6 mmol) and trichloroacetonitrile (2.6 mL, 26 mmol) to afford the title compound as a light grey powder (480 mg, 55%). $^1$H NMR (400 MHz, Acetone-d6): δ 9.01 (br. s, 1H), 8.31 (br. d, J=75.1 Hz, 1H), 7.79 (br. d, J=51.9 Hz, 1H), 7.25 (br. s, 1H), 7.14 (br. s, 1H), 6.79 (d, J=0.9 Hz, 1H), 6.69 (dd, J=8.1, 1.0 Hz, 1H), 2.25 (s, 3H). $^{13}$C NMR (101 MHz, Acetone-d6): δ 173.8, 168.7, 165.6, 149.0, 135.8, 124.7, 123.6, 121.3, 118.0, 97.3, 20.9. HRMS-ESI (m/z): [M+H]$^+$ calc. for $C_{11}H_{11}OCl_3N_5$$^+$334.00237; Found 334.00250. HPLC ($\lambda_{254}$): 100%; $t_R$: 9.948 min (method 4).

2-((4-amino-6-phenyl-1,3,5-triazin-2-yl)amino)-5-methylphenol (MTF411)

Synthesized following the general procedure E using 1-(6-methylbenzo[d]oxazol-2-yl)guanidine (500 mg, 2.6 mmol), sodium hydride (60% oil suspension, 114 mg, 2.9 mmol) and benzonitrile (0.27 mL, 2.6 mmol) to afford the title compound as a beige powder (410 mg, 54%). $^1$H NMR (400 MHz, Acetone-d6): δ 9.75 (br. s, 1H), 8.37 (d, J=7.4 Hz, 2H), 8.30 (br. s, 1H), 7.59-7.53 (m, 2H), 7.48 (t, J=7.3 Hz, 2H), 6.80 (s, 1H), 6.74 (br. s, 2H), 6.69 (d, J=8.0 Hz, 1H), 2.26 (s, 3H). $^{13}$C NMR (101 MHz, Acetone-d6): δ 171.9, 168.4, 165.6, 149.1, 137.4, 135.4, 132.5, 129.1, 129.0 (2C), 125.9, 123.3, 121.3 (2C), 119.2, 20.9. HRMS-ESI (m/z): [M+H]$^+$ calc. for $C_{16}H_{16}ON_5$$^+$294.13494; Found 294.13495. HPLC ($\lambda_{254}$): 99.7%; $t_R$: 8.456 min (method 4).

2-((4-amino-6-phenyl-1,3,5-triazin-2-yl)amino)phenol (MTF412)

Synthesized following the general procedure E using 1-(benzo[d]oxazol-2-yl)guanidine (500 mg, 2.8 mmol), sodium hydride (60% suspension in oil, 123 mg, 3.1 mmol) and benzonitrile (0.29 mL, 2.8 mmol) to afford the title compound as a light brown powder (53 mg, 7%). $^1$H NMR (400 MHz, Acetone-d6): δ 9.82 (br. s, 1H), 8.39 (d, J=7.1 Hz, 2H), 8.31 (br. s, 1H), 7.83 (d, J=7.7 Hz, 1H), 7.58-7.52 (m, 1H), 7.52-7.46 (m, 2H), 7.03-6.94 (m, 2H), 6.90-6.84 (m, 1H), 6.77 (br. s, 2H). $^{13}$C NMR (101 MHz, Acetone-d6): δ 172.0, 168.5, 165.7, 148.9, 137.4, 132.6, 129.1 (2C), 129.0 (2C), 128.5, 125.3, 123.1, 120.7, 118.3. HRMS-ESI (m/z): [M+H]$^+$ calc. for $C_{15}H_{14}ON_5^+$ 280.11929; Found 280.11929. HPLC ($\lambda_{254}$): 98.9%; $t_R$: 8.100 min (method 4).

2-((6-imino-4-phenyl-1,6-dihydro-1,3,5-triazin-2-yl)amino)-4-nitrophenol (MTF413)

Synthesized following the general procedure E using 1-(6-nitrobenzo[d]oxazol-2-yl)guanidine (500 mg, 2.3 mmol), sodium hydride (60% suspension in oil, 100 mg, 2.5 mmol) and benzonitrile (0.24 mL, 2.3 mmol) to afford the title compound as a light yellow powder (62 mg, 8%). $^1$H NMR (400 MHz, DMSO-d6): δ 11.39 (br. s, 1H), 8.63 (d, J=9.0 Hz, 1H), 8.36-8.30 (m, 2H), 8.26 (s, 1H), 7.80 (dd, J=9.0, 2.6 Hz, 1H), 7.70 (d, J=2.6 Hz, 1H), 7.61-7.56 (m, 1H), 7.52 (dd, J=11.4, 4.4 Hz, 2H), 7.45 (br. s, 2H). $^{13}$C NMR (101 MHz, DMSO-d6): δ 170.7, 167.2, 164.2, 146.4, 141.5, 136.1, 134.5, 131.9, 128.5 (2C), 128.0 (2C), 118.9, 115.4, 108.9. HRMS-ESI (m/z): [M+H]$^+$ calc. for $C_{15}H_{13}O_3N_6^+$ 325.10436; Found 325.10446. HPLC ($\lambda_{254}$): 99.1%; $t_R$: 10.242 min (method 4).

2-((6-imino-4-(pyrazin-2-yl)-1,6-dihydro-1,3,5-triazin-2-yl)amino)phenol (MTF439)

Synthesized following the general procedure E using 1-(benzo[d]oxazol-2-yl)guanidine (500 mg, 2.8 mmol), sodium hydride (60% oil suspension, 123 mg, 3.08 mmol) and pyrazinecarbonitrile (250 μL, 2.8 mmol) to afford the title compound as a bright yellow powder (510 mg, 65%). The biguanide was then dissolved in DMSO and stirred for 8 h at r.t. to give the desired product as a bright yellow powder. $^1$H NMR (400 MHz, DMSO-d6): δ 10.07 (br. s, 1H), 9.41 (s, 1H), 8.79 (s, 2H), 8.57 (s, 1H), 7.88 (dd, J=8.0, 0.6 Hz, 1H), 7.53 (br. s, 1H), 7.41 (br. s, 1H), 6.99-6.93 (m, 1H), 6.90 (dd, J=8.0, 1.4 Hz, 1H), 6.85-6.79 (m, 1H). $^{13}$C NMR (101 MHz, DMSO-d6): δ 168.7, 167.2, 164.6, 149.4, 148.4, 146.4, 144.6, 144.5, 126.8, 124.4, 123.0, 119.2, 116.1. HRMS-ESI (m/z): [M+H]$^+$ calc. for $C_{13}H_{12}ON_7^+$ 282.10978; Found 282.10977. HPLC ($\lambda_{254}$): 98.8%; $t_R$: 4.209 min (method 4).

N—(N-(benzo[d]oxazol-2-yl)carbamimidoyl)pyrazine-2-carboximidamide (MTF440)

Synthesized following the general procedure E using 1-(benzo[d]oxazol-2-yl)guanidine (500 mg, 2.8 mmol), sodium hydride (60% oil suspension, 123 mg, 3.08 mmol) and 3-pyridinecarbonitrile (292 mg, 2.8 mmol) to afford the title compound as a bright yellow powder (510 mg, 65%). $^1$H NMR (400 MHz, DMSO-d6): δ 9.98 (s, 1H), 9.40 (d, J=1.4 Hz, 1H), 8.73 (dd, J=4.8, 1.7 Hz, 1H), 8.54 (d, J=8.0 Hz, 1H), 8.34 (s, 1H), 7.93 (dd, J=7.9, 1.4 Hz, 1H), 7.54 (ddd, J=8.0, 4.8, 0.5 Hz, 1H), 7.32 (s, 2H), 6.98-6.93 (m, 1H), 6.91-6.88 (m, 1H), 6.86-6.80 (m, 1H). $^{13}$C NMR (101 MHz, DMSO-d6): δ 168.8, 167.0, 164.4, 152.1, 149.1, 148.1, 135.2, 132.0, 126.8, 124.1, 123.6, 122.7, 119.1, 115.7. HRMS-ESI (m/z): [M+H]$^+$ calc. for $C_{14}H_{13}ON_6^+$ 281.11454; Found 281.11450. HPLC ($\lambda_{254}$): 99.7%; $t_R$: 4.165 min (method 4).

N2,N2'-(disulfanediylbis(2,1-phenylene))bis(6-(naphthalen-2-yl)-1,3,5-triazine-2,4-diamine) (MTF443)

Synthesized following the general procedure B using N—(N-(benzo[d]thiazol-2-yl)carbamimidoyl)-2-naphthimidamide (345 mg, 1 mmol) to afford the title compound as a white powder (299 mg, 87%). $^1$H NMR (400 MHz, DMSO-d6): δ 9.30 (s, 1H), 8.87 (s, 1H), 8.36 (d, J=8.5 Hz, 1H), 7.99 (dd, J=19.5, 10.4 Hz, 3H), 7.68 (d, J=7.8 Hz, 1H), 7.63-7.53 (m, 2H), 7.48 (d, J=7.7 Hz, 1H), 7.29 (t, J=7.2 Hz, 1H), 7.25-7.11 (m, 3H). $^{13}$C NMR (101 MHz, DMSO-d6): δ 170.19, 167.33, 165.53, 136.81, 134.58, 134.17, 133.57, 132.40, 128.98, 128.66, 128.16, 127.74, 127.65 (2C), 127.51, 126.55 (2C), 126.26, 124.75. HPLC ($\lambda_{280}$): Purity 97.3%; $t_R$: 15.642 min (method 2).

N2,N2'-(disulfanediylbis(2,1-phenylene))bis(6-(2,2-dimethyl-2H-chromen-6-yl)-1,3,5-triazine-2,4-diamine) (MTF444)

Synthesized following the general procedure B using N—(N-(benzo[d]thiazol-2-yl)carbamimidoyl)-2,2-dimethyl-2H-chromene-6-carboximidamide (377 mg, 1 mmol) to afford the title compound as a white powder (241 mg, 64%). $^1$H NMR (400 MHz, DMSO-d6): δ 9.10 (s, 1H), 8.00 (d, J=8.5 Hz, 1H), 7.95 (s, 1H), 7.61 (d, J=9.0 Hz, 1H), 7.41 (d, J=7.1 Hz, 1H), 7.27 (t, J=7.0 Hz, 1H), 7.16 (t, J=7.5 Hz, 1H), 6.99 (s, 2H), 6.81 (d, J=8.5 Hz, 1H), 6.45 (d, J=9.9 Hz, 1H), 5.80 (d, J=9.8 Hz, 1H), 1.40 (s, 6H). $^{13}$C NMR (101 MHz, DMSO-d6): δ 169.67, 167.15, 165.33, 155.42, 136.86, 133.39, 131.25, 129.26, 129.18, 128.51, 127.69, 126.41, 126.16 (2C), 121.61, 120.26, 115.65, 76.97, 27.93 (2C). HPLC ($\lambda_{280}$): Purity 95.2%; $t_R$: 15.767 min (method 2).

N2,N2'-(disulfanediylbis(2,1-phenylene))bis(6-(3-nitrophenyl)-1,3,5-triazine-2,4-diamine) (MTF445)

Synthesized following the general procedure B using N—(N-(benzo[d]thiazol-2-yl)carbamimidoyl)-3-nitrobenzimidamide (340 mg, 1 mmol) to afford the title compound as a white powder (265 mg, 78%). $^1$H NMR (400 MHz, DMSO-d6): δ 9.41 (s, 1H), 9.04 (s, 1H), 8.60 (d, J=6.8 Hz, 1H), 8.39 (dd, J=8.2, 1.4 Hz, 1H), 7.79 (t, J=8.0 Hz, 1H), 7.64 (d, J=7.9, 0.9 Hz, 1H), 7.39 (dd, J=7.8, 0.9 Hz, 1H), 7.36-7.17 (m, 4H). $^{13}$C NMR (101 MHz, DMSO-d6): δ 168.16, 167.23, 165.49, 147.97, 138.33, 136.42, 133.75 (2C), 130.10, 128.35, 127.72, 126.82, 126.57, 125.93, 122.27. HPLC ($\lambda_{280}$): Purity 95.3%; $t_R$: 13.550 min (method 2).

N2,N2'-(disulfanediylbis(2,1-phenylene))bis(6-(3,4,5-trimethoxyphenyl)-1,3,5-triazine-2,4-diamine) (MTF446)

Synthesized following the general procedure B using N—(N-(benzo[d]thiazol-2-yl)carbamimidoyl)-3,4,5-trimethoxybenzimidamide (385 mg, 1 mmol) to afford the title compound as a white powder (358 mg, 93%). $^1$H NMR (400 MHz, DMSO-d6): δ 9.24 (s, 1H), 7.59 (s, 3H), 7.40 (d, J=7.7 Hz, 1H), 7.27 (t, J=7.5 Hz, 1H), 7.12 (dd, J=23.2, 15.8 Hz, 3H), 3.79 (s, 6H), 3.73 (s, 3H). $^{13}$C NMR (101 MHz, DMSO-d6): δ 169.55, 167.26, 165.29, 152.58 (2C), 140.36, 136.92, 133.81, 131.90, 128.71, 127.66, 126.37, 126.11, 105.08 (2C), 60.11, 55.74 (2C). HPLC ($\lambda_{280}$): Purity 96.6%; $t_R$: 10.367 min (method 2).

N2,N2'-(disulfanediylbis(2,1-phenylene))bis(6-(benzo[d][1,3]dioxol-5-yl)-1,3,5-triazine-2,4-diamine) (MTF449)

Synthesized following the general procedure B using N—(N-(benzo[d]thiazol-2-yl)carbamimidoyl)benzo[d][1,3]dioxole-5-carboximidamide (340 mg, 1 mmol) to afford the title compound as a white powder (247 mg, 73%). $^1$H NMR (400 MHz, DMSO-d6): δ 9.14 (s, 1H), 7.87 (d, J=8.1 Hz, 1H), 7.68 (s, 1H), 7.61 (d, J=7.8 Hz, 1H), 7.39 (d, J=7.7 Hz, 1H), 7.27 (t, J=7.4 Hz, 1H), 7.17 (t, J=7.5 Hz, 1H), 7.08-6.97 (m, 3H), 6.10 (s, 2H). $^{13}$C NMR (101 MHz, DMSO-d6): δ 169.41, 167.15, 165.34, 150.10, 147.37, 136.77, 133.53, 130.76, 128.41, 127.66, 126.47, 126.21, 122.88, 107.97, 107.44, 101.60. HPLC ($\lambda_{280}$): Purity 95.1%; $t_R$: 10.767 min (method 2).

N2,N2'-(disulfanediylbis(2,1-phenylene))bis(6-(2-chlorophenyl)-1,3,5-triazine-2,4-diamine) (MTF450)

Synthesized following the general procedure B using N—(N-(benzo[d]thiazol-2-yl)carbamimidoyl)-2-chlorobenzimidamide (329 mg, 1 mmol) to afford the title compound as a white powder (273 mg, 83%). $^1$H NMR (400 MHz, DMSO-d6): δ 9.30 (s, 1H), 7.58 (dt, J=9.4, 4.8 Hz, 2H), 7.51 (dd, J=7.8, 1.0 Hz, 1H), 7.45 (td, J=7.7, 2.0 Hz, 1H), 7.41 (dd, J=7.4, 1.3 Hz, 1H), 7.38 (d, J=6.8 Hz, 1H), 7.28-7.22 (m, 1H), 7.22-7.09 (m, 3H). $^{13}$C NMR (101 MHz, DMSO-d6): δ 172.24, 166.83, 165.19, 137.48, 136.34, 133.55, 130.93, 130.50, 130.47, 129.82, 128.16, 127.59, 127.08, 126.87, 126.52. HPLC ($\lambda_{280}$): Purity 95.1%; $t_R$: 10.517 min (method 2).

N2,N2'-(disulfanediylbis(2,1-phenylene))bis(6-(p-tolyl)-1,3,5-triazine-2,4-diamine) (MTF451)

Synthesized following the general procedure B using N—(N-(benzo[d]thiazol-2-yl)carbamimidoyl)-4-methylbenzimidamide (309 mg, 1 mmol) to afford the title compound as a white powder (179 mg, 58%). $^1$H NMR (400 MHz, DMSO-d6): δ 9.15 (s, 1H), 8.14 (d, J=8.0 Hz, 2H), 7.61 (d, J=7.9 Hz, 1H), 7.41 (d, J=7.1 Hz, 1H), 7.26 (dd, J=8.8, 4.7 Hz, 3H), 7.17 (t, J=7.5 Hz, 1H), 7.04 (s, 2H), 2.36 (s, 3H). $^{13}$C NMR (101 MHz, DMSO-d6): δ 170.14, 167.25, 165.46, 141.31, 136.80, 133.90, 133.44, 128.86 (2C), 128.52, 127.86 (2C), 127.71, 126.51, 126.21, 21.09. HPLC ($\lambda_{280}$): Purity 96.7%; $t_R$: 12.958 min (method 2).

N2,N2'-(disulfanediylbis(2,1-phenylene))bis(6-(2-fluorophenyl)-1,3,5-triazine-2,4-diamine) (MTF452)

Synthesized following the general procedure B using N—(N-(benzo[d]thiazol-2-yl)carbamimidoyl)-2-fluorobenzimidamide (313 mg, 1 mmol) to afford the title compound as a white powder (191 mg, 61%). $^1$H NMR (400 MHz, DMSO-d6): δ 9.26 (s, 1H), 7.87 (td, J=7.7, 1.6 Hz, 1H), 7.59 (dd, J=7.9, 1.0 Hz, 1H), 7.56-7.49 (m, 1H), 7.39 (d, J=7.6 Hz, 1H), 7.30-7.23 (m, 3H), 7.20-7.10 (m, 3H). $^{13}$C NMR (101 MHz, DMSO-d6): δ 169.77 (d), 166.97, 165.31, 160.33 (d), 136.49, 133.54, 132.19 (d), 131.13 (d), 128.26, 127.65, 126.92, 126.46, 125.89 (d), 124.09 (d), 116.50 (d). HPLC ($\lambda_{280}$): Purity 95.4%; $t_R$: 10.333 min (method 2).

N2,N2'-(disulfanediylbis(2,1-phenylene))bis(6-(2,6-dichlorophenyl)-1,3,5-triazine-2,4-diamine) (MTF455)

Synthesized following the general procedure B using N—(N-(benzo[d]thiazol-2-yl)carbamimidoyl)-2,6-dichlorobenzimidamide (364 mg, 1 mmol) to afford the title compound as a white powder (320 mg, 88%). $^1$H NMR (400 MHz, DMSO-d6): δ 9.44 (s, 1H), 7.55 (dd, J=13.4, 7.9 Hz, 3H), 7.45 (dd, J=9.0, 7.1 Hz, 1H), 7.33 (d, J=7.7 Hz, 1H), 7.30-7.22 (m, 3H), 7.18 (t, J=7.1 Hz, 1H). $^{13}$C NMR (101 MHz, DMSO-d6): δ 170.75, 166.93, 165.40, 136.69, 135.98, 133.90, 132.08 (2C), 130.63, 128.12 (2C), 127.88, 127.50, 127.25, 126.83. HPLC ($\lambda_{280}$): Purity 95.8%; $t_R$: 10.150 min (method 2).

N2,N2'-(disulfanediylbis(2,1-phenylene))bis(6-(3,5-dibromopyridin-4-yl)-1,3,5-triazine-2,4-diamine) (MTF456)

Synthesized following the general procedure B using N—(N-(benzo[d]thiazol-2-yl)carbamimidoyl)-3,5-dibromoisonicotinimidamide (454 mg, 1 mmol) to afford the title compound as a white powder (412 mg, 91%). $^1$H NMR (400 MHz, DMSO-d6): δ 9.56 (s, 1H), 8.84 (s, 2H), 7.57 (d, J=7.7 Hz, 1H), 7.39 (d, J=14.8 Hz, 2H), 7.31 (d, J=7.6 Hz, 1H), 7.25 (t, J=7.2 Hz, 1H), 7.20 (d, J=5.4 Hz, 1H). $^{13}$C NMR (101 MHz, DMSO-d6): δ 170.93, 166.78, 165.27, 150.32 (2C), 146.43, 135.71, 133.98, 127.70, 127.49, 127.35, 127.02, 119.05 (2C). HPLC ($\lambda_{280}$): Purity 95.1%; $t_R$: 9.700 min (method 2).

N2,N2'-(disulfanediylbis(2,1-phenylene))bis(6-(6-bromobenzo[d][1,3]dioxol-5-yl)-1,3,5-triazine-2,4-diamine) (MTF458)

Synthesized following the general procedure B using N—(N-(benzo[d]thiazol-2-yl)carbamimidoyl)-6-bromobenzo[d][1,3]dioxole-5-carboximidamide (418 mg, 1 mmol) to afford the title compound as a white powder (300 mg, 72%). $^1$H NMR (400 MHz, DMSO-d6): δ 9.31 (s, 1H), 7.57 (d, J=7.6 Hz, 1H), 7.38 (d, J=7.3 Hz, 1H), 7.28-7.23 (m, 2H), 7.22-7.11 (m, 4H), 6.12 (s, 2H). $^{13}$C NMR (101 MHz, DMSO-d6): δ 172.43, 166.50, 165.08, 148.68, 146.86, 136.29, 133.50, 132.49, 128.17, 127.63, 127.08, 126.58, 112.81, 111.49, 109.98, 102.31. HPLC ($\lambda_{280}$): Purity 96.1%; $t_R$: 10.475 min (method 12).

N2,N2'-(disulfanediylbis(2,1-phenylene))bis(6-(3-aminophenyl)-1,3,5-triazine-2,4-diamine) (MTF460)

Synthesized following the general procedure B using 3-amino-N—(N-(benzo[d]thiazol-2-yl)carbamimidoyl)benzimidamide (310 mg, 1 mmol) to afford the title compound as a yellow powder (241 mg, 78%). $^1$H NMR (400 MHz, DMSO-d6): δ 9.06 (s, 1H), 7.61 (dd, J=7.9, 1.2 Hz, 1H), 7.49 (s, 1H), 7.43 (d, J=7.8 Hz, 2H), 7.27 (td, J=7.7, 1.3 Hz, 1H), 7.17 (t, J=7.6 Hz, 1H), 7.09 (t, J=7.8 Hz, 1H), 6.98 (s, 2H), 6.71 (dd, J=7.9, 1.4 Hz, 1H), 5.18 (s, 2H). $^{13}$C NMR (101 MHz, DMSO-d6): δ 170.95, 167.23, 165.44, 148.52, 137.33, 136.87, 133.20, 128.59, 128.55, 127.72, 126.43, 126.12, 116.94, 115.86, 113.34. HPLC ($\lambda_{280}$): Purity 97.8%; $t_R$: 7.167 min (method 2).

1,1'-((((disulfanediylbis(2,1-phenylene))bis(azanediyl))bis(6-amino-1,3,5-triazine-4,2-diyl))bis(3,1-phenylene))bis(ethan-1-one) (MTF462)

Synthesized following the general procedure B using 3-acetyl-N—(N-(benzo[d]thiazol-2-yl)carbamimidoyl)benzimidamide (337 mg, 1 mmol) to afford the title compound as a white powder (225 mg, 67%). $^1$H NMR (400 MHz, DMSO-d6): δ 9.32 (s, 1H), 8.83 (s, 1H), 8.46 (d, J=7.4 Hz, 1H), 8.13 (d, J=7.8 Hz, 1H), 7.64 (t, J=7.1 Hz, 2H), 7.40 (d, J=7.1 Hz, 1H), 7.23 (dt, J=15.3, 8.0 Hz, 4H), 2.61 (s, 3H). $^{13}$C NMR (101 MHz, DMSO-d6): δ 197.57, 169.41, 167.28, 165.49, 137.06, 136.86, 136.62, 133.74, 132.14, 131.24, 128.80, 128.46, 127.69, 127.32, 126.67, 126.40, 26.77. HPLC ($\lambda_{280}$): Purity 96.9%; $t_R$: 10.908 min (method 2).

N2,N2'-(disulfanediylbis(2,1-phenylene))bis(6-(2-nitrophenyl)-1,3,5-triazine-2,4-diamine) (MTF463)

Synthesized following the general procedure B using N—(N-(benzo[d]thiazol-2-yl)carbamimidoyl)-2-nitrobenzimidamide (340 mg, 1 mmol) to afford the title compound as a white powder (278 mg, 82%). $^1$H NMR (400 MHz, DMSO-d6): δ 9.29 (s, 1H), 7.92 (d, J=7.6 Hz, 1H), 7.86 (d, J=7.3 Hz, 1H), 7.77 (t, J=7.3 Hz, 1H), 7.70 (t, J=7.6 Hz, 1H), 7.57 (d, J=7.8 Hz, 1H), 7.32 (d, J=7.6 Hz, 1H), 7.28-7.07 (m, 4H). $^{13}$C NMR (101 MHz, DMSO-d6): δ 170.32, 166.77, 165.14, 149.12, 136.11, 133.49, 132.58, 132.34, 130.89, 130.51, 128.06, 127.58, 127.11, 126.63, 123.88. HPLC ($\lambda_{280}$): Purity 98.9%; $t_R$: 10.350 min (method 2).

Cell Cultures

Fresh sterile tissues were obtained from surgical waste from patients diagnosed with metastatic melanoma at the Nice CHU hospital. Epidermal cell suspensions were obtained from foreskins of Caucasian children by overnight digestion in phosphate-buffered saline containing 0.5% dispase grade II at 4° C., followed by a 20 min digestion with 0.05% trypsin-0.02% EDTA in phosphate-buffered saline (V/V) at 37° C. Human primary melanocytes were grown in MCDB153 medium supplemented with 2% FCS, 0.4 µg/ml hydrocortisone, 5 µg/ml insulin, 16 nM phorbol-12 myristate 13-acetate, 1 ng/ml basic fibroblast growth factor, 10 µg/ml bovine pituitary extract and penicillin/streptomycin (100 U/ml/50 µg/ml). Human primary keratinocytes were cultured in KSFM medium in which 0.1 ng/ml epidermal growth factor, 15 µg/ml bovine pituitary extract and penicillin/streptomycin (100 U/ml/50 µg/ml) were added. Human primary fibroblasts and melanoma cells, derived from the corresponding dermis, were grown in DMEM 7% Foetal Calf Serum (FCS) and penicillin/streptomycin (100 U/ml/50 µg/ml). Written informed consent was obtained from each patient included in this study, and the study was approved by the hospital ethics committee (Nice Hospital Center and University of Nice Sophia Antipolis, no. 210-2998).

Different melanoma cell lines were purchased from the American Tissue Culture Collection: A375 and WM9 cells are mutated on B-Raf, CDKN2A and PTEN proteins; SKmel28 cells are mutated on B-Raf and P53 proteins; 1205Lu cells are mutated on B-Raf and PTEN proteins; G-361 cells are mutated on B-Raf and CDKN2A proteins; C8161 cells are mutated on B-Raf and K-Ras proteins; WM3912 cells are mutated on B-Raf and CDKN2A proteins; MeWo cells are mutated on P53 and CDKN2A proteins; WM3918 presents no mutations on characteristic proteins.

Resistant melanoma cell lines A375 and SKMel28 were a gift from Professor P. Marchetti and described in Corazao-Rozas et al. (2013). Cells were grown in RPMI 1640 or in DMEM supplemented with 10% of Foetal Calf Serum (FCS) and penicillin/streptomycin (100 U/ml/50 mg/ml) at 37° C. and 5% CO2.

Trypan Blue Exclusion Assay

For trypan blue staining, 200 mL of cells (melanoma and normal human cells) were aseptically transferred to a 1.5 mL clear Eppendorf tube and incubated for 3 min at room temperature with an equal volume of 0.4% trypan blue solution. Viable cells were counted and the results are expressed as the percentage of the value of control cells. All the experiments are performed 3 times in triplicate.

Viability Test

A375 Sensitive cells were treated with different concentrations of the synthesized molecules (5.0 µM or 10 µM) for different times (24 hr or 48 hr) or with DMSO (Control) for 12 or 48 hr. At the end of the stimulation, viable cells were counted using the trypan blue dye exclusion method. The results are normalized as percentages compare to the control. The results are shown in Table 1. They show that compounds of formula (I), (II) and (III) induce a decrease of the viability of melanoma cells.

Kinetic of CRO15

A375 Sensitive cells were treated with 5 µM of CRO15 for different times (2 hr, 4 hr, 6 hr, 8 hr, 12 hr, 24 hr or 48 hr) or with 5 µM of PLX4032 (B-Raf inhibitor) for 48 hr or with DMSO (Control) for 48 hr. At the end of stimulation, viable cells were counted using the trypan blue dye exclusion method. The results are normalized as percentages compare to the control and data means±SEM of three independent experiments performed in triplicate *p<0.05; p<0.01; *p<0.001. The results are shown in FIG. 1A. They show that CRO15 induces a decrease of the viability of melanoma cells and that the decrease of the viability after 48 hr is more important with CRO15 than with PLX4032.

IC50 of CRO15

A375 Sensitive cells were treated with different concentrations of CRO15 (0.5 µM, 2.5 µM, 5.0 µM, 7.5 µM, 50 µM) for 48 hr or with 5 µM of PLX4032 (B-Raf inhibitor) for 48 hr or with DMSO (Control) for 48 hr. At the end of the stimulation, viable cells were counted using the trypan blue dye exclusion method. The results are normalized as percentages compare to the control and data means±SEM of three independent experiments performed in triplicate *p<0.05; p<0.01; *p<0.001. IC50 of CRO15 have been determined at 3.75 µM at 48 hr. The results are shown in FIG. 1B. They show that there is a dose-response relationship for CRO15 on melanoma cells viability.

Viability Test with CRO15

Different melanoma cell lines with various mutations, patient cells with various mutations and normal human cells, were treated with 5 µM of CRO15 for 48 hours or DMSO (Control). At the end of stimulation, viable cells were counted using the trypan blue dye exclusion method. The results are normalized as percentages compare to the control and data means±SEM of three independent experiments performed in triplicate *p<0.05; p<0.01; *p<0.001. The results are shown in FIG. 1C (melanoma cell lines with various mutations) and 1D (patient cells with various mutations) and 1E (normal human cells). They show that CRO15 induces a decrease of the viability of different melanoma cell lines with various mutations and different patient cells with various mutations, while CRO15 is not toxic for normal cells.

Viability Test of CRO15 on Resistant Melanoma Cells

A375 sensitive and resistant melanoma cells were treated with 5 µM of CRO15 for 48 hr or with 5 µM of PLX4032 for 48 hr or with DMSO (Control). At 48 hours, viable cells were counted using the trypan blue dye exclusion method. The results are normalized as percentages compare to the control and data means±SEM of three independent experiments performed in triplicate *p<0.05; p<0.01; *p<0.001. The results are shown in FIG. 4A. They show that CRO15 induces a decrease of the cell viability in both sensitive and resistant melanoma cells and that the decrease of the viability is more important with CRO15 than with PLX4032.

Viability Test of CRO15 on Double Resistant Cells to BRAF and MEK Inhibitors

Melanoma cell line DR6 resistant cells to B-Raf inhibitor (Vemurafenib=PLX4032) and to MEK inhibitor (Cobimetinib) were treated with DMSO (control), with 5 µM or 10 µM of CRO15 or with a combination of 1 µM of vemurafenib and 0.5 µM of cobimetinib. After 24 hours of stimulation, viable cells were counted using the trypan blue dye exclusion method. The results are normalized as percentages compare to the control. Error bars represents ±SEM of triplicate.

The results are shown in FIG. 5. They show that CRO15 induces a decrease of the cell viability of melanoma cell line resistant to B-Raf inhibitor (PLX4032) and to MEK inhibitor (Cobimetinib).

Western Blot Assays

Western blot analyses were performed as described (Lehraiki et al., 2014). Proteins were extracted in buffer containing 50 mmol/l Tris-HCl (pH 7.5), 15 mmol/1, NaCl, 1% Triton X-100, and 1× protease and phosphatase inhibitors. Briefly, cell lysates (30 mg) were separated by SDS-PAGE, transferred onto a polyvinylidene fluoride membrane (Millipore), and then exposed to the appropriate antibodies. Proteins were visualized with the ECL System from Amersham. The western blot analyses shown are representative of at least three independent experiments.

Western Blot analysis: A375 Sensitive cells were treated with 5 µM of CRO15 for different time (6 hr, 12 hr or 24 hr) or with DMSO (Control) for 24 hr.

The results are shown in FIG. 2. They show that CRO15 induces an activation of AMPK.

In Vivo Murine Cancer Model

Animal experiments were carried out in accordance with the Declaration of Helsinki and were approved by a local ethical committee CIEPAL (Comité Institutionnel d'Ethique Pour l'Animal de Laboratoire-Azur). Female immune-deficient BALB/c nu/nu (nude) mice were obtained at 5 weeks of age from Envigo Laboratory (Gannat, France). Nude mice were inoculated subcutaneously with A375 sensitive or resistant melanoma cells (1.0×106 cells/mouse). After tumor apparition (±5 days), animals received intraperitoneal injection of Labrafil (Control), PLX4032 (0.7 mg/mouse/day) or CRO15 (0.7 mg/mouse/day) dissolved in Labrafil. The growth tumor curves were determined by measuring the tumor volume using the equation V=(L*W2)/2 (V=tumor volume, W=tumor width, L=tumor length). At the end of the experiment, mice were euthanized by cervical dislocation and tumors were taken for western blot and immunofluorescence experiments (LC3, Cleaved Caspase 3). TUNEL assay was performed using the In Situ Cell Death Detection Kit (Roche, Meylan, France). The results are shown in FIGS. 3A and 3B (A375 sensitive melanoma cells), and 4B and 4C (A375 resistant melanoma cells). They show that CRO15 reduces both the tumor volume and weight of mice inoculated with both sensitive and resistant melanoma cells.

Xenograft—A375 Resistant cells (Riv)

In Vivo Murine Cancer Model Animal experiments were carried out in accordance with the Declaration of Helsinki and were approved by a local ethical committee CIEPAL (Comite Institutionnel d'Ethique Pour l'Animal de Laboratoire-Azur). Female immune-deficient BALB/c nu/nu (nude) mice were obtained at 5 weeks of age from Envigo Laboratory (Gannat, France). Nude mice were inoculated subcutaneously with A375 resistant melanoma cells (1.0× 106 cells/mouse). After tumor apparition (+5 days), animals received intraperitoneal injection of Labrafil (Control), PLX4032 (0.7 mg/mouse/day) or MTF319 (0.7 mg/mouse/day) dissolved in Labrafil. The growth tumor curves were determined by measuring the tumor volume using the equation V=(L*W2)/2 (V=tumor volume, W=tumor width, L=tumor length). At the end of the experiment, mice were euthanized by cervical dislocation.

The results are shown in FIGS. 6A and 6B. They show a decrease in tumor volume when mice were injected with MTF319. The tumor weight also indicates that MTF319 had an effect on the tumor growth.

CRO15 Inhibits Tumor Growth of Murine Melanoma BP Cells Allografted into C57BL6 Mice In Vivo Murine Cancer Model Animal experiments were carried out in accordance with the Declaration of Helsinki and were approved by a local ethical committee CIEPAL (Comite Institutionnel d'Ethique Pour l'Animal de Laboratoire-Azur). Female C57BL6/J mice were obtained at 5 weeks of age from Envigo Laboratory (Gannat, France). Mice were inoculated subcutaneously with BP melanoma cells (1×10$^6$ cells/mouse). After tumor apparition (+5 days), animals received intraperitoneal injection of Labrafil (vehicle) or CRO15 (0.7 mg/mouse/day). The growth tumor curves were determined by measuring the tumor volume using the equation V=(L*W2)/2, (V=tumor volume, W=tumor width, L=tumor length). At the end of the experiment, mice were euthanized by cervical dislocation.

The results are shown in FIG. 7A. The bars indicate the mean±SEM. *p<0.05; **p<0.01. They show that immunocompetent mice (C57BL/6) subcutaneously injected with murine melanoma cells (BP cells) showed no tumor growth when treated daily with CRO15 compared with those treated with vehicle.

To study weither melanoma cells WM9 would develop resistance to CRO15, these cells were kept in culture during 8 weeks in presence of increasing concentrations of either, DMSO (control), PLX4032, CRO15 or MTF255. The starting concentration was 0.2 µM. Every 2 passages, drug concentration was slightly increased (+0.2 µM) until reaching resistance to PLX4032 when channeling with 10 µM as observed in the FIG. 7B.

Along with non-treated WM9S (naive cells), drug-treated WM9S were then stimulated with 10 µM of each drug during 48 hrs. Viable cells were counted using the trypan blue dye exclusion method. The results are normalized as percentages compare to the control (DMSO). Error bars represents ±SEM of triplicate.

The results are shown in FIG. 7B. They show that that PLX-treated WM9 became resistant to PLX4032 while CRO15 is still able to induce cell death in CRO15-treated WM9.

TABLE 1

| ID | Structure | Viab A375 10 μM/ 24 h | Viab A375 5 μM/ 24 h | Viab A375 10 μM/ 48 h | Viab A375 5 μM/ 48 h |
| --- | --- | --- | --- | --- | --- |
| CRO15 | Molecular Weight: 671,2220 | 23% | 36% | 2.6% | 27% |
| MTF 232 | Molecular Weight: 731,2740 | 33.9% ±2 | 83.3% ±5.3 | 16.4 ±4.9% | 24.9% ±8.5 |
| MTF 233 | Molecular Weight: 740,1060 | 7% ±0.6 | 13.9% ±3.6 | 4.7% ±1.7 | 8.9% ±2.1 |
| MTF 234 | Molecular Weight: 707,2028 | 9.6% ±3.2 | 29.6% ±6.1 | 7.8% ±3.6 | 17.4% ±3.6 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 242 | (benzothiazol-2-yl guanidine with 3-bromophenyl) Molecular Weight: 374,2600 | 13.4% ±4.5 | 29.2% ±0.0 | 2.9% ±4 | 8.1% ±3.1 |
| MTF 243 | (benzothiazol-2-yl guanidine with 3-chlorophenyl) Molecular Weight: 329,8060 | 12.1% ±3.1 | 22.1% ±3.8 | 2.7% ±1.7 | 7% ±11.1 |
| MTF 244 | (benzothiazol-2-yl guanidine with 2-chlorophenyl) Molecular Weight: 329,8060 | 84.9% ±9.9 | 81.6% ±22.6 | 68.4% ±13.4 | 68% ±26 |
| MTF 245 | (benzothiazol-2-yl guanidine with 4-chlorophenyl) Molecular Weight: 329,8060 | 83% ±16.3 | 95% ±9.2 | 79.6% ±7.8 | 100% ±8.5 |
| MTF 246 | (benzothiazol-2-yl guanidine with 4-methylphenyl) Molecular Weight: 309,3910 | 94% ±58 | 137% ±33.7 | 115% ±26 | 91% ±7.8 |
| MTF 247 | (benzothiazol-2-yl guanidine with 4-iodophenyl) Molecular Weight: 421,2605 | 122% ±79 | 100% ±33 | 100% ±49 | 135% ±39 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 248 | 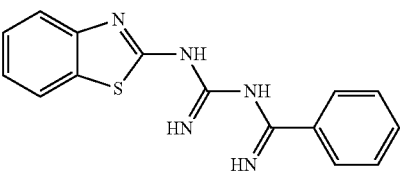 Molecular Weight: 295,3640 | 80% ±7.2 | 100% ±31 | 138% ±59 | 100% ±16 |
| MTF 249 | 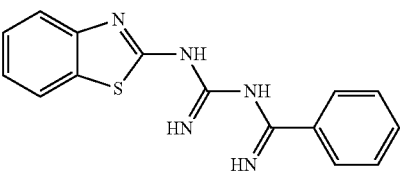 Molecular Weight: 313,3544 | 14.4% ±1 | 25.4% ±8.1 | 8.9% ±2.9 | 10.6% ±6.7 |
| MTF 250 | 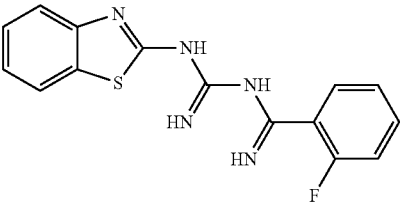 Molecular Weight: 374,2600 | 12% ±1.5 | 25.4% ±4.2 | 2.4% ±1.2 | 8.9% ±5.6 |
| MTF 251 | 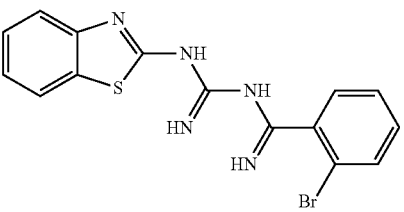 Molecular Weight: 296,3520 | 45.1% ±3.1 | 48.9% ±3.6 | 19.5% ±7.8 | 44.7% ±2.9 |
| MTF 252 | 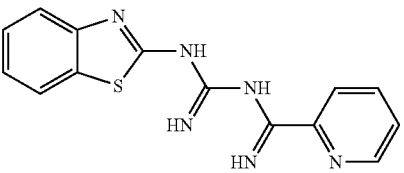 Molecular Weight: 296,3520 | 12.9% ±1 | 8.6% ±3 | 2.6% ±1 | 5.2% ±4.6 |
| MTF 253 | 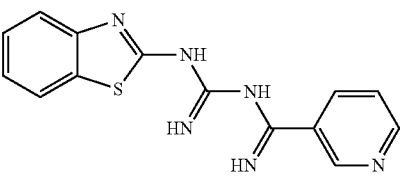 Molecular Weight: 296,3520 | 14.9% ±2.5 | 27.8% ±7.6 | 4.1% ±3.5 | 6.9% ±5 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 254 | Molecular Weight: 325,3900 | 100% ±31 | 100% ±23 | 100% ±12 | 100% ±55 |
| MTF 255 | Molecular Weight: 337,4010 | 3.2% ±1.7 IC50 = 2.3 μM | 26.1% ±7.1 | 3.8% ±0.6 | 4.7% ±5.3 |
| MTF 256 | Molecular Weight: 400,29800 | 66% ±3.2 | 93.9% ±2.3 | 95.7% ±20 | 60% ±7.1 |
| MTF 257 | Molecular Weight: 445,29500 | 106% ±18 | 100% ±10 | 62% ±11 | 80.5% ±7.1 |
| MTF 259 | Molecular Weight: 367,38700 | 98% ±24 | 157% ±1.7 | 96.5% ±11 | 95.7% ±26.3 |

TABLE 1-continued

| ID | Structure | Viab A375 10 µM/ 24 h | Viab A375 5 µM/ 24 h | Viab A375 10 µM/ 48 h | Viab A375 5 µM/ 48 h |
|---|---|---|---|---|---|
| MTF 260 | 4-(3-nitrophenyl)thiazol-2-yl guanidine with nicotinamidine<br>Molecular Weight: 367,38700 | 76.7% ±21 | 57% ±2.5 | 78% ±65 | 32% ±24 |
| MTF 261 | 4-(3-nitrophenyl)thiazol-2-yl guanidine with isonicotinamidine<br>Molecular Weight: 367,38700 | 71.9% ±6.4 | 24.6% ±11 | 115% ±1.4 | 63.6% ±9.9 |
| MTF 262 | 4-phenylthiazol-2-yl guanidine with 4-methoxybenzamidine<br>Molecular Weight: 351,42800 | 40.8% ±9.1 | 61.4% ±15.7 | 27.3% ±5.3 | 43.7% ±17.6 |
| MTF 263 | 4-phenylthiazol-2-yl guanidine with picolinamidine<br>Molecular Weight: 322,39000 | 100% ±7.6 | 89.5% ±8.4 | 66% ±8 | 91% ±6.8 |

TABLE 1-continued

| ID | Structure | Viab A375 10 µM/ 24 h | Viab A375 5 µM/ 24 h | Viab A375 10 µM/ 48 h | Viab A375 5 µM/ 48 h |
|---|---|---|---|---|---|
| MTF 264 | Molecular Weight: 404,2860 | 89% ±19 | 87% ±15 | 99% ±28 | 94.9% v46 |
| MTF 265 | Molecular Weight: 388,2870 | 84% ±3.8 | 91% ±8.7 | 60% ±8.4 | 100% ±10 |
| MTF 267 | Molecular Weight: 355,84400 | 134% ±5.4 | 113% ±11.9 | 73.3% ±39 | 113% ±29 |
| MTF 268 | Molecular Weight: 355,84400 | 146% ±13.7 | 67% ±6.1 | 122% ±43 | 47% ±5.5 |
| MTF 272 | Molecular Weight: 321,40200 | 88% ±10 | 100% ±6.2 | 54.6% ±32 | 81% ±21 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 273 | Molecular Weight: 322,39000 | 100% ±6.6 | 46% ±2.9 | 100% ±12 | 48% ±8.2 |
| MTF 274 | Molecular Weight: 322,39000 | 84% ±11 | 83% ±5.9 | 89% ±20 | 93% ±15 |
| MTF 276 | Molecular Weight: 400,84100 | 73.9% ±24.4 | 91.6% ±5.1 | 64.9% ±7.2 | 95.3% ±13.9 |
| MTF 277 | Molecular Weight: 400,84100 | 76.4% ±5.2 | 77.6% ±16 | 85.8% ±10 | 88% ±12 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 281 | (3-nitrophenyl-thiazol-2-yl)-N'-(4-chlorobenzimidamide)guanidine<br>Molecular Weight: 400,84100 | 57.4% ±4.9 | 79% ±15 | 78% ±15 | 112% ±2 |
| MTF 283 | (4-methylthiazol-2-yl)-N'-benzimidamide guanidine<br>Molecular Weight: 259,3310 | 100% ±9 | 100% ±10 | 150% ±4 | 56% ±5.6 |
| MTF 284 | (4-methylthiazol-2-yl)-N'-(2-chlorobenzimidamide)guanidine<br>Molecular Weight: 293,7730 | 104.1% ±11.4 | 80.1% ±3.1 | 76.9% ±9.2 | 117.3% ±13.1 |
| MTF 285 | (4-methylthiazol-2-yl)-N'-(3-chlorobenzimidamide)guanidine<br>Molecular Weight: 293,7730 | 77.8% ±8 | 45% ±4.5 | 78.7% ±3.8 | 100% ±8 |
| MTF 286 | (4-methylthiazol-2-yl)-N'-(4-chlorobenzimidamide)guanidine<br>Molecular Weight: 293,7730 | 65.3% ±7.3 | 48% ±2.3 | 120% ±11.5 | 155% ±16 |
| MTF 287 | (4-methylthiazol-2-yl)-N'-(2-bromobenzimidamide)guanidine<br>Molecular Weight: 328,2270 | 53.7% ±3.8 | 60.9% ±11.7 | 69.5% ±14.2 | 86.7% ±19.8 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 288 | Molecular Weight: 338,2270 | 70% ±4.6 | 50% ±10 | 53.5% ±14.9 | 96.7% ±17 |
| MTF 289 | Molecular Weight: 260,3190 | 78.7% ±29 | 81.1% ±7.2 | 58.2% ±12.5 | 90.4% ±26.5 |
| MTF 290 | Molecular Weight: 260,3190 | 50.5% ±5.6 | 43.4% ±8.3 | 14.4% ±2.4 | 21.6% ±15.9 |
| MTF 291 | Molecular Weight: 260,3190 | 100% ±11 | 100% ±12 | 41.3% ±1.8 | 95.2% ±15.9 |
| MTF 292 | Molecular Weight: 289,3570 | 141.9% ±12.9 | 88.1% ±8.9 | 71.9% ±8 | 83.3% ±18.7 |
| MTF 295 | Molecular Weight: 352,2540 | 66.1% ±7.2 | 108.9% ±18.9 | 39.3% ±4.2 | 37.3% ±15 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 296 | 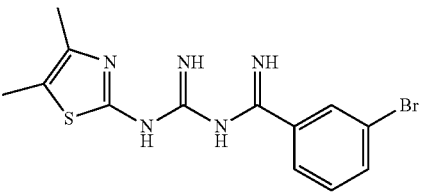<br>Molecular Weight: 352,2540 | 21.1% ±9.5 | 39.4% ±7.1. | 6.8% ±6.1 | 11.7% ±6.8 |
| MTF 297 | 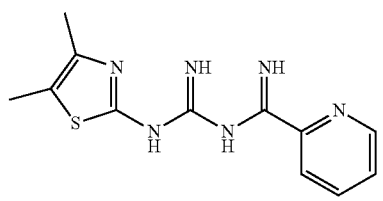<br>Molecular Weight: 274,3460 | 97.9% ±8.1 | 86.2% ±7.5 | 24.9% ±7.2 | 59.8% ±5.5 |
| MTF 298 | 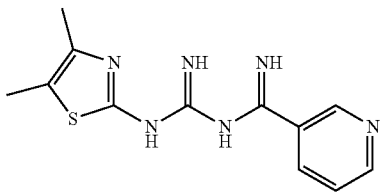<br>Molecular Weight: 274,3460 | 87.5% ±5.1 | 97.2% ±13 | 54.7% ±21.8 | 73.6% ±15.1 |
| MTF 299 | 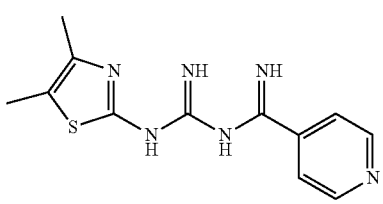<br>Molecular Weight: 274,3460 | 72.8% ±14.6 | 91.1% ±7.2 | 46.2% ±2.8 | 76.6% ±32.5 |
| MTF 300 | 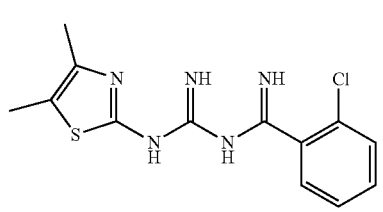<br>Molecular Weight: 307,800 | 50.8% ±6.4 | 96% ±9.3 | 35.9% ±6 | 60% ±16.1 |
| MTF 301 | 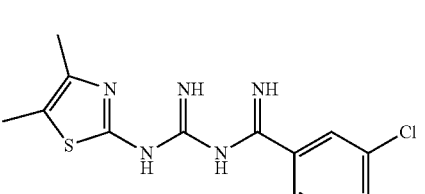<br>Molecular Weight: 307,8000 | 106.4% ±14.2 | 74% ±15 | 31.6% ±20 | 47% ±23 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 302 | (4,5-dimethylthiazol-2-yl)-guanidine-benzamidine with 4-Cl phenyl<br>Molecular Weight: 307,8000 | 94.8% ±3.5 | 104.6% ±9 | 39.3% ±8.7 | 52.3% ±24.3 |
| MTF 303 | (4,5-dimethylthiazol-2-yl)-guanidine-benzamidine<br>Molecular Weight: 273,3580 | 66.1% ±6.1 | 85.6% ±23.2 | 39.1% ±16 | 44.2% ±4.9 |
| MTF 305 | benzothiazol-2-yl-guanidine-trichloroacetamidine<br>Molecular Weight: 336,61900 | 5.5% ±0 | 11% ±4.6 | 4.7% ±2.5 | 20.7% ±13.1 |
| MTF 316 | $H_2N$-triazine-$CCl_3$ with 2-(methylthio)phenyl-NH<br>Molecular Weight: 350,6460 | 103.8% ±13.3 | 124.5% ±9.3 | 48.2% ±8.5 | 69.6% ±37.5 |
| MTF 317 | $H_2N$-triazine-$CHCl_2$ with 2-(methylthio)phenyl-NH<br>Molecular Weight: 316,2040 | 108.6% ±6.6 | 106.4% ±9.5 | 70% ±17.7 | 58.7% ±21.1 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
| --- | --- | --- | --- | --- | --- |
| MTF 318 | 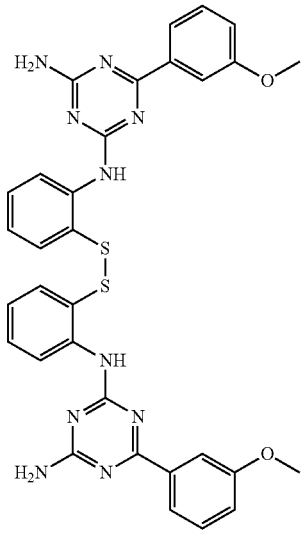<br>Molecular Weight: 648,7640 | 20.5% ±0.6 | 74.1% ±3.8 | 6.3% ±3.2 | 21.6% ±5 |
| MTF 319 | 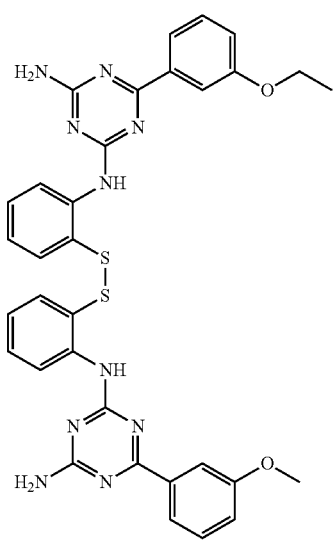<br>Molecular Weight: 676,8180 | 8.6% ±4 | 8.6% ±2.1 | 0.6% ±0.6 | 3.1% ±1.2 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 320 | 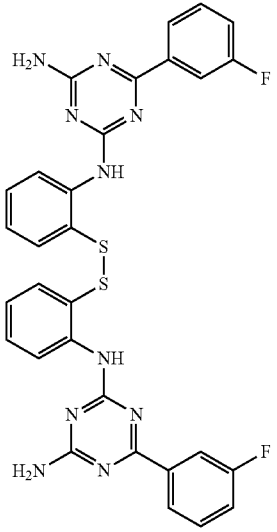<br>Molecular Weight: 624,6928 | 10.8% ±2.5 | 18.3% ±3.1 | 8.5% ±1.5 | 11.5% ±1.5 |
| MTF 321 | 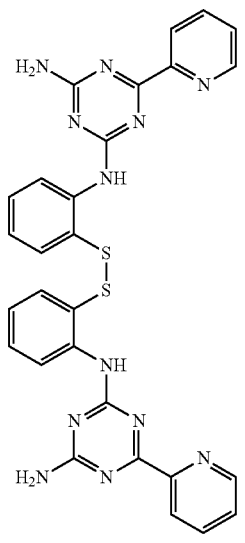<br>Molecular Weight: 590,6880 | 53.8% ±5.8 | 59.7% ±2.1 | 32.1% ±9.1 | 34.5% ±1.4 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 322 | 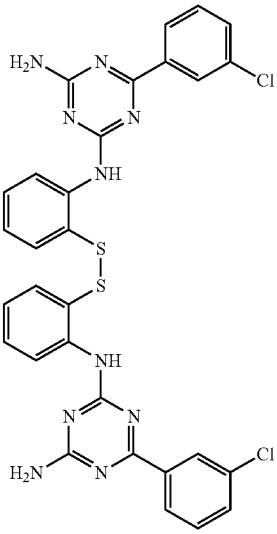 Molecular Weight: 657,5960 | 26.9% ±2.6 | 57.4% ±4 | 5.7% ±2 | 12.1% ±1.5 |
| MTF 323 | 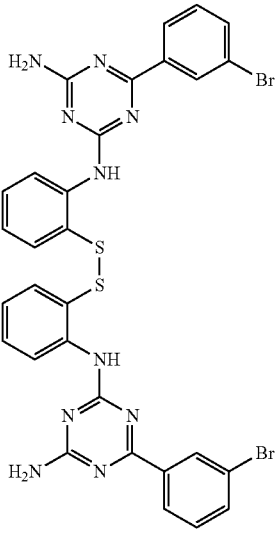 Molecular Weight: 746,5040 | 47.4% ±1.5 | 34.6% ±4.6 | 8.3% ±3.1 | 23.5% ±3.2 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 324 | 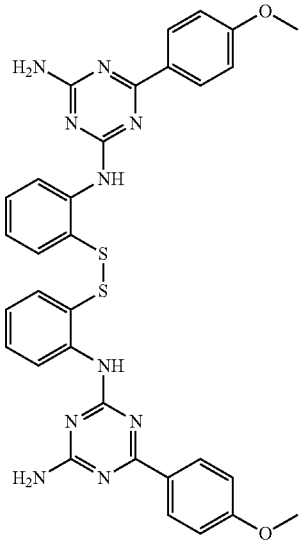 Molecular Weight: 648,7640 | 12.9% ±3 | 44.1% ±7.5 | 8.2% ±0.7 | 13.3% ±3.25 |
| MTF 325 | 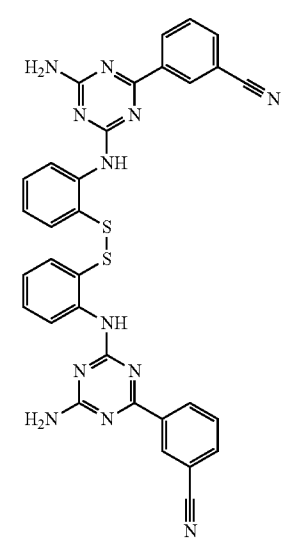 Molecular Weight: 638,7320 | 71% ±1 | 58.1% ±0 | 29.7% ±3.2 | 30.9% ±5.7 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 326 | 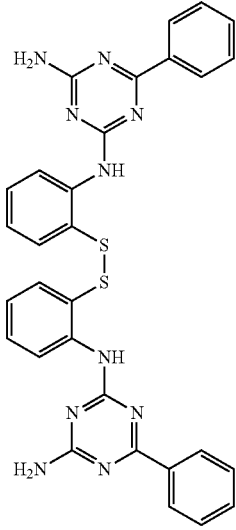 Molecular Weight: 588,7120 | 12.9% ±0 | 27.4% ±0.7 | 6.7% ±3.1 | 27.9% ±0.7 |
| MTF 327 | 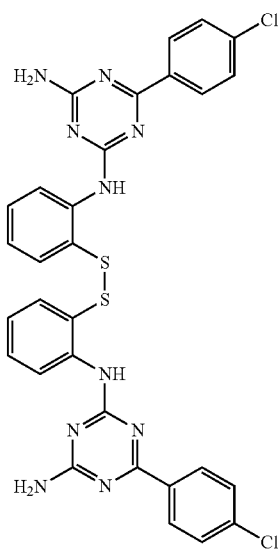 Molecular Weight: 657,5960 | 23.7% ±0.6 | 19.4% ±1.7 | 14.5% ±4.6 | 14.5% ±1 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 328 | 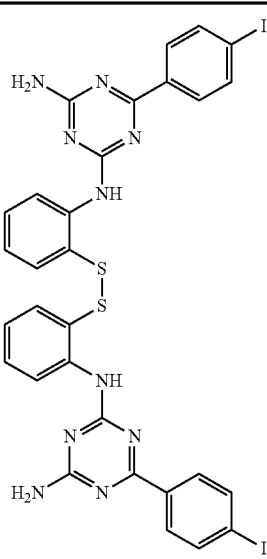<br>Molecular Weight: 840,5049 | 27.8% ±6.4 | 50% ±8.2 | 3.4% ±3 | 9.4% ±4.4 |
| MTF 329 | 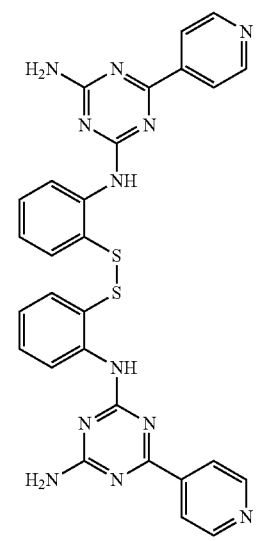<br>Molecular Weight: 590,6880 | 74.2% ±6.1 | 96.2% ±3.5 | 22.5% ±13.1 | 69.7% ±2.1 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 330 | Molecular Weight: 590,6880 | 60.1% ±10.7 | 122.7% ±17 | 41.6% ±9.1 | 73.9% ±3.5 |
| MTF 331 | Molecular Weight: 358,1990 | 150.8% ±3.5 | 104.5% ±2.8 | 77.4% ±16.3 | 82.9% ±4.2 |
| MTF 332 | Molecular Weight: 313,7450 | 104.5% ±8.2 | 122% ±9.2 | 65.4% ±6.4 | 87.6% ±6.4 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
| --- | --- | --- | --- | --- | --- |
| MTF 333 | Molecular Weight: 616,77 | 28.7% ±3.2 | 94.9% ±0.9 | 24.1% ±3.9 | 35.4% ±1 |
| MTF 342 | Molecular Weight: 325,3900 | 32.2% ±5.7 | 48.6% ±5.5 | 8.6% ±3.2 | 8.6% ±3.2 |
| MTF 343 | Molecular Weight: 363,3622 | 34.8% ±5.5 | 67.7% ±21 | 24.1% ±14.2 | 52.9% ±13.4 |
| MTF 344 | Molecular Weight: 339,4170 | 38.7% ±7.8 | 84.3% ±0.7 | 26.1% ±11.6 | 26.1% ±11.6 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
| --- | --- | --- | --- | --- | --- |
| MTF 345 | Molecular Weight: 297,3400 | 17.1% ±2.8 | 25.9% ±2.5 | 1% ±0.6 | 1.8% ±0.6 |
| MTF 346 | Molecular Weight: 313,3544 | 43.2% ±0 | 66.9% ±1.4 | 12.9% ±7.2 | 10.6% ±5.6 |
| MTF 347 | Molecular Weight: 320,3740 | 27.6% ±2.1 | 26.9% ±2.1 | 6.8% ±3.5 | 6.6% ±3.2 |
| MTF 348 | Molecular Weight: 592,6640 | 110% ±9.2 | 101.8% ±11 | 35.8% ±4.9 | 79.6% ±44.5 |
| MTF 379 | Molecular Weight: 330,7940 | 95.7% ±14.8 | 148.2% ±10.3 | 86.2% ±0 | 76.9% ±12.7 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 380 | *benzothiazole-NH-C(=NH)-NH-C(=NH)-(2-chloropyridin-4-yl)*  Molecular Weight: 330,7940 | 36.2% ±6 | 47.3% ±5.7 | 2.3% ±1 | 4.9% ±1.2 |
| MTF 381 | *benzothiazole-NH-C(=NH)-NH-C(=NH)-thiophen-2-yl*  Molecular Weight: 301,3860 | 90.6% ±13.2 | 88.3% ±8.5 | 61.4% ±24.4 | 61.6% ±31.8 |
| MTF 382 | *benzothiazole-NH-C(=NH)-NH-C(=NH)-(3,4,5-trimethoxyphenyl)*  Molecular Weight: 385,4420 | 17.4% ±1.5 | 14.7% ±5.5 | 4.5% ±3.1 | 1.8% ±0.7 |
| MTF 383 | *benzothiazole-NH-C(=NH)-NH-C(=NH)-(benzo[d][1,3]dioxol-5-yl)*  Molecular Weight: 339,3730 | 41.6% ±6.4 | 43.1% ±11.5 | 7.1% ±6.4 | 40.6% ±23.3 |
| MTF 384 | *benzothiazole-NH-C(=NH)-NH-C(=NH)-(naphthalen-2-yl)*  Molecular Weight: 345,4240 | 93.3% ±4.7 | 76.1% ±7.5 | 72.2% ±10.6 | 119.3% ±13.4 |
| MTF 385 | *benzothiazole-NH-C(=NH)-NH-C(=NH)-(4-trifluoromethylphenyl)*  Molecular Weight: 363,3622 | 86.6% ±11.5 | 52.3% ±6.4 | 81.5% ±10.6 | 68.1% ±3.5 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 386 | Molecular Weight: 375,2480 | 18.1% ±5.3 | 28.9% ±8.7 | 3.7% ±0.6 | 6.6% ±3.5 |
| MTF 387 | Molecular Weight: 380,2820 | 67.8% ±1.5 | 70.1% ±14.4 | 55.6% ±14 | 56.2% ±5 |
| MTF 388 | Molecular Weight: 377,4660 | 55.7% ±7.5 | 61.4% ±15.5 | 18.4% ±2.1 | 65.1% ±7.8 |
| MTF 389 | Molecular Weight: 365,2360 | 75.8% ±4 | 74.6% ±2.6 | 76.4% ±11.3 | 85.6% ±13.4 |
| MTF 394 | Molecular Weight: 724,70842 | 4.5% ±1 | 13.1% ±1.2 | 1.1% ±0.6 | 4.4% ±1.2 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 396 | (structure) Molecular Weight: 600,75600 | 7.5% ±1.2 | 19.2% ±5.1 | 0% ±0 | 12.1% ±4.9 |
| MTF 397 | (structure) Molecular Weight: 758,54800 | 13.4% ±1 | 35.4% ±3.1 | 7.3% ±2.1 | 33.7% ±4 |
| MTF 398 | (structure) Molecular Weight: 340,36100 | 91% ±9.5 | 91.9% ±2.3 | 108.6% ±11.3 | 132.4% ±0.7 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 373 | Molecular Weight: 320,5580 | 38.6% ±5.7 | 34.3% ±2.1 | 22.8% ±3.2 | 22.5% ±10.6 |
| MTF 374 | Molecular Weight: 355,0000 | 24.0% ±7.1 | 47.0% ±7.3 | 27.7% ±9.2 | 69.2% ±0.0 |
| MTF 375 | Molecular Weight: 355,00000 | 30.9% ±8.7 | 47.2% ±2.1 | 15.5% ±0.7 | 29.5% ±3.5 |
| MTF 376 | Molecular Weight: 365,5550 | 24.3% ±7.6 | 44.7% ±5.7 | 20.9% ±7.5 | 38.9% ±2.1 |
| MTF 377 | Molecular Weight: 365,5550 | 22.7% ±9.2 | 27.3% ±3.5 | 33.5% ±4.2 | 34.4% ±2.1 |
| MTF 443 | Molecular Weight: 365,5550 | 13.8% ±6.4 | 42.3% ±7.1 | 7.8% ±4.2 | 10.2% ±4.0 |

TABLE 1-continued
| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 445 | 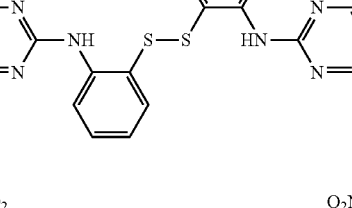<br>Molecular Weight: 678,7060 | 72.4% ±7.4 | 62.6% ±10.3 | 16.3% ±0.0 | 35.2% ±10.6 |
| MTF 446 | 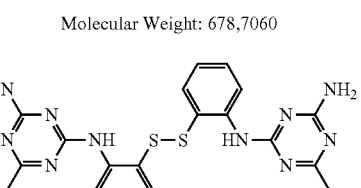<br>Molecular Weight: 768,8680 | 16.3% ±1.5 | 62.6% ±3.5 | 1.8% ±1.4 | 13.0% ±6.8 |
| MTF 449 | 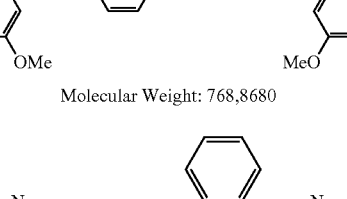<br>Molecular Weight: 676,7300 | 59.1% ±8.5 | 74.2% ±14.6 | 53.0% ±5.0 | 67.8% ±23.3 |
| MTF 450 | 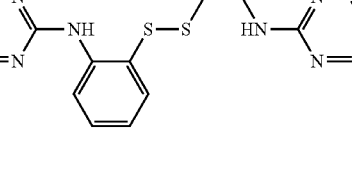<br>Molecular Weight: 657,5960 | 38.3% ±15.0 | 38.6% ±17.1 | 49.9% ±17.6 | 54.8% ±16.4 |
| MTF 451 | 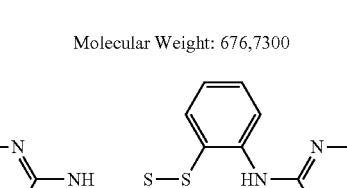<br>Molecular Weight: 616,7660 | 10.6% ±4.9 | 26.1% ±7.5 | 12.5% ±9.3 | 23.9% ±17.7 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 452 | Molecular Weight: 624,6928 | 22.3% ±11.6 | 43.6% ±1.5 | 40.3% ±6.8 | 60.5% ±14.0 |
| MTF 455 | Molecular Weight: 726,4800 | 32.3% ±0.6 | 89.0% ±13.1 | 69.5% ±17.1 | 108.1% ±9.9 |
| MTF 456 | Molecular Weight: 906,2720 | 52.3% ±3.6 | 66.5% ±1.5 | 76.1% ±30.8 | 87.5% ±23.4 |
| MTF 458 | Molecular Weight: 834,5220 | 46.5% ±9.9 | 58.7% ±3.2 | 103.7% ±7.2 | 86.8% ±11.5 |
| MTF 460 | Molecular Weight: 618,7420 | 64.5% ±12.1 | 61.9% ±6.1 | 38.6% ±2.8 | 69.5% ±7.1 |

TABLE 1-continued

| ID | Structure | Viab A375 10 μM/ 24 h | Viab A375 5 μM/ 24 h | Viab A375 10 μM/ 48 h | Viab A375 5 μM/ 48 h |
|---|---|---|---|---|---|
| MTF 462 | Molecular Weight: 672,7860 | 4.8% ±17.4 | 101.3% ±37.3 | 44.1% ±6.9 | 80.0% ±17.7 |
| MTF 463 | Molecular Weight: 678,7060 | 56.1% ±5.2 | 80.0% ±6.8 | 43.4% ±7.1 | 74.3% ±21.4 |

The invention claimed is:

1. A compound of formula (II) or (III)

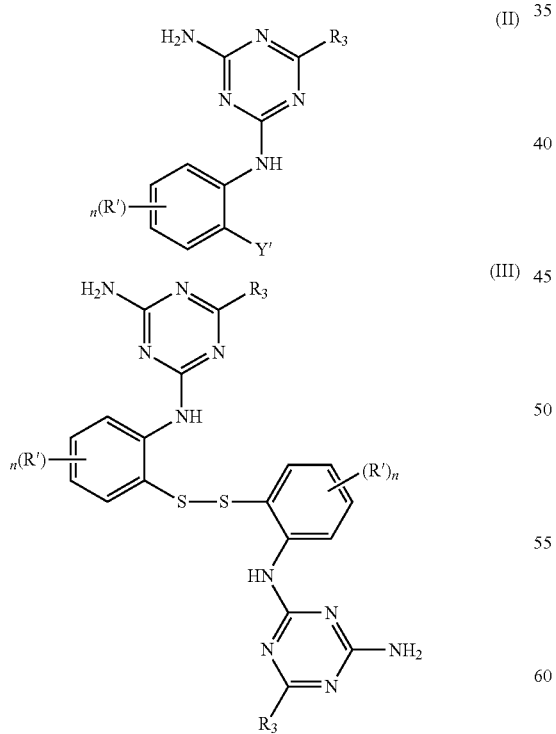

wherein

Y' is —SR$_4$ or —OR$_5$,

R$_4$ is selected from C$_1$-C$_6$ alkyl and protecting groups selected from any group linked by a disulfide function, thioesters, alkyl, alkenyl and alkynyl thioethers, benzyl thioethers, alkylarylmethyl thioethers, and triarylmethylthioethers;

R$_5$ is selected from protecting groups selected from esters, silylated ethers, alkoxymethyl ethers, benzyl ethers tetrahydropyranyl ethers, pentoses, and hexoses;

each R' is independently selected from halogen, C$_1$-C$_6$ alkyl, C$_1$-C$_6$ alkoxy, C$_1$-C$_6$ haloalkyl, —OH, —NR"R'", —NO$_2$, —CN and —(CO)—R;

n is 0 to 4;

R$_3$ is selected from C$_1$-C$_6$ alkyl, C$_3$-C$_6$ cycloalkyl, C$_1$-C$_6$ haloalkyl, C$_2$-C$_6$ alkenyl, C$_2$-C$_6$ alkynyl, heterocyclyl having 5 to 10 ring atoms, aryl having 6 to 10 ring atoms, heteroaryl having 5 to 10 ring atoms and C$_7$-C$_{16}$ aralkyl, said alkyl, cycloalkyl, haloalkyl, alkenyl, alkynyl, heterocyclyl, aryl, heteroaryl and aralkyl being optionally substituted with one or more substituents independently selected from halogen, C$_1$-C$_6$ alkyl, C$_1$-C$_6$ alkoxy, C$_1$-C$_6$haloalkyl, —OH, —NR"R", —NO$_2$, —CN and —(CO)—R;

each R is independently selected from H, C$_1$-C$_6$ alkyl, C$_1$-C$_6$ alkoxy and —NR"R" ';

each R" and R' is independently selected from H and C$_1$-C$_6$ alkyl.

2. The compound of claim 1, wherein

Y' is —SR$_4$, R$_4$ being selected from C$_1$-C$_6$ alkyl;

each R' is independently selected from halogen and C$_1$-C$_6$ alkoxy;

n is 0 to 1;

R$_3$ is selected from C$_1$-C$_6$ haloalkyl, aryl having 6 to 10 ring atoms, heteroaryl having 5 to 10 ring atoms, and C$_7$-C$_{16}$ aralkyl, said aryl, heteroaryl and aralkyl being optionally substituted with one or more substituents independently selected from halogen, C$_1$-C$_6$ alkoxy, and —CN.

3. The compound of claim 1, wherein the compound is
CRO 15
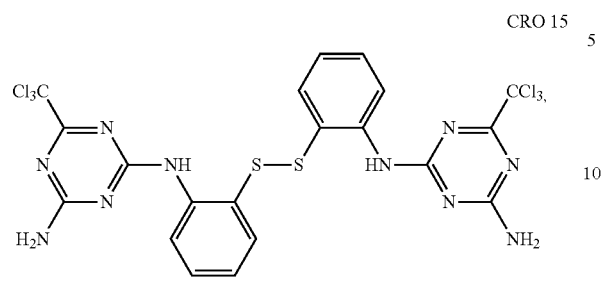
MTF 232
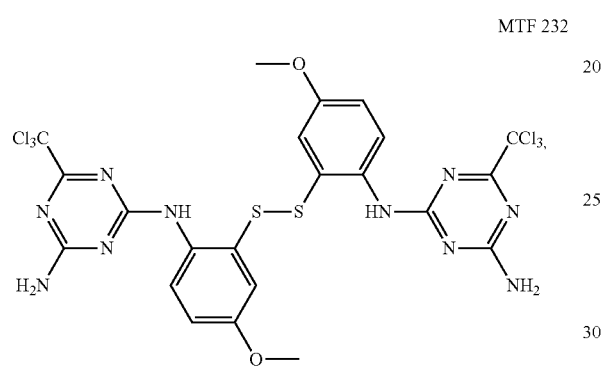
MTF 233
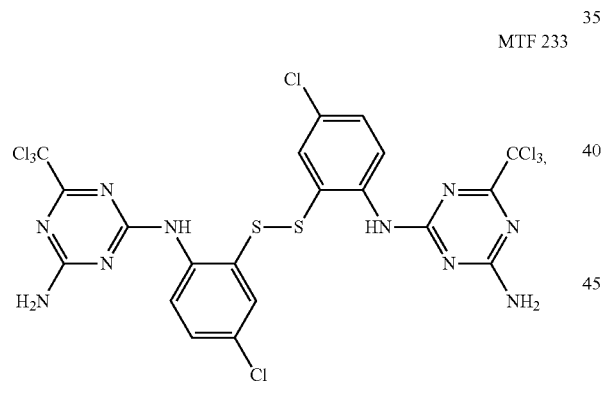
MTF 234
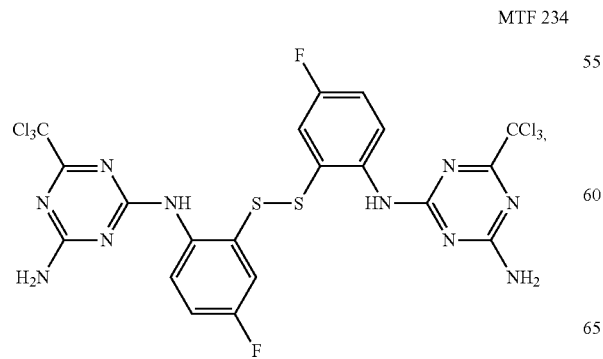
-continued
MTF 318
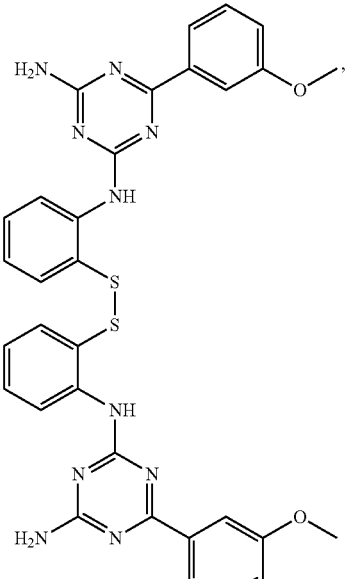
MTF 319
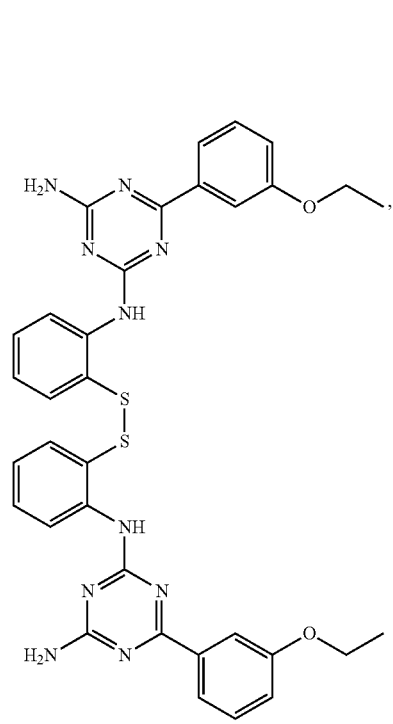

MTF 320
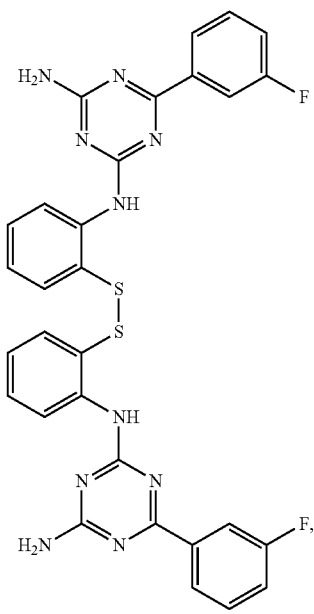
MTF 322
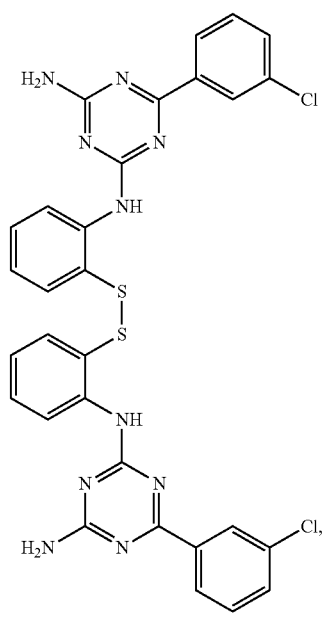
MTF 321
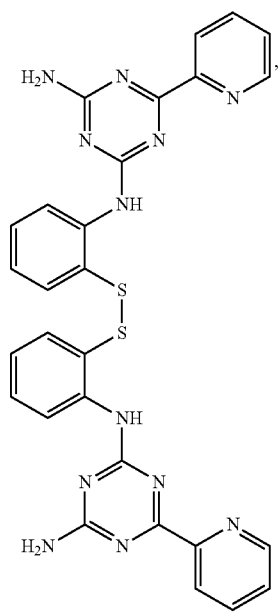
MTF 323
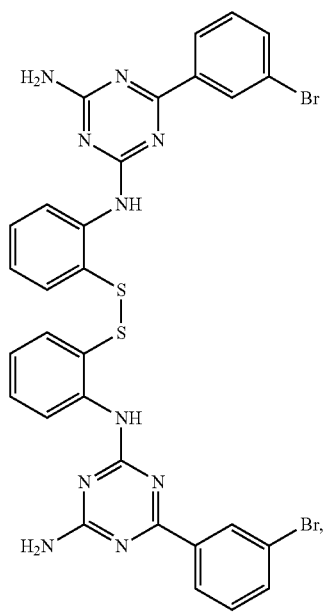

MTF 324
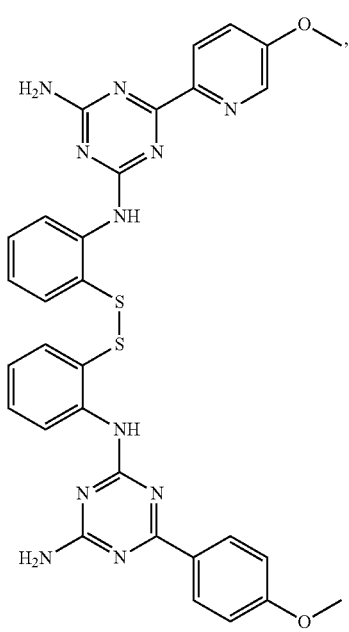
MTF 326
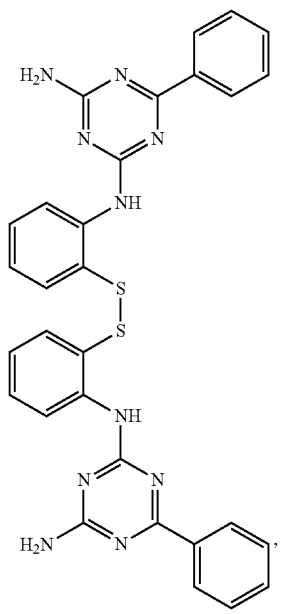
MTF 325
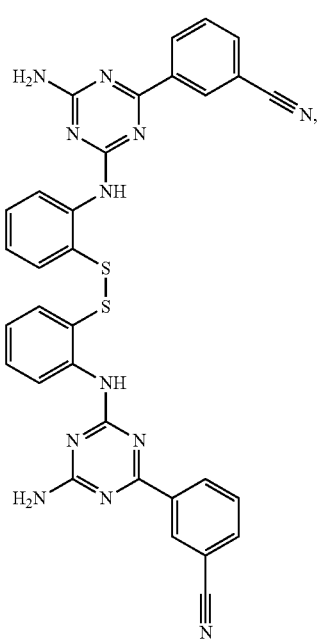
MTF 327
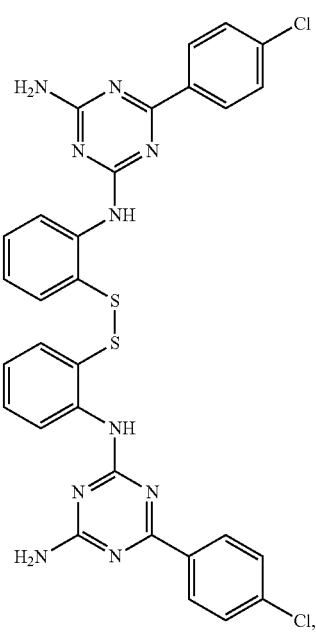

161
-continued
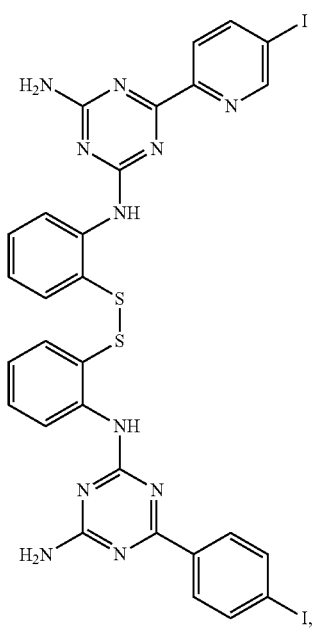
MTF 328
162
-continued
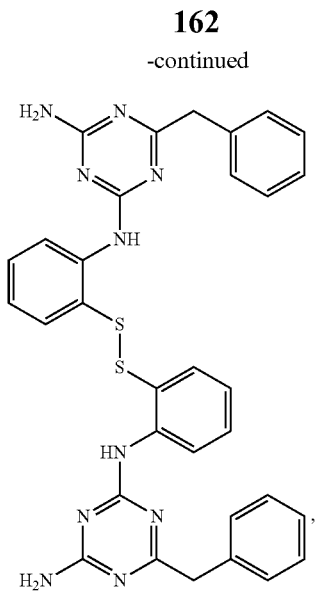
MTF 333
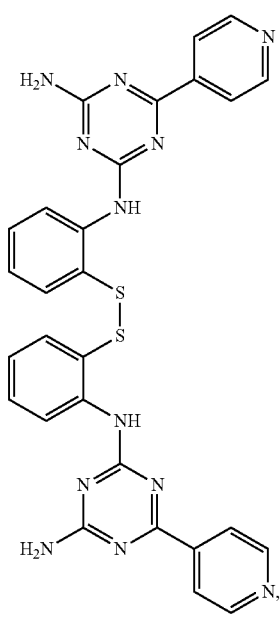
MTF 329
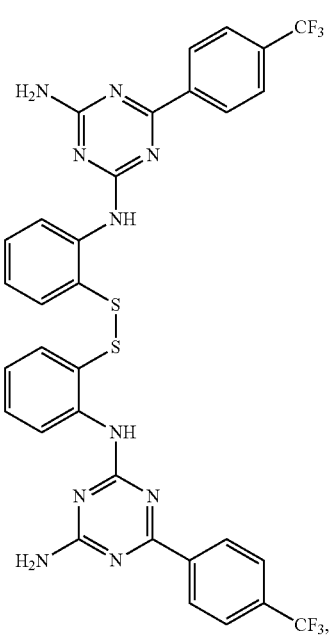
MTF 394

MTF 396
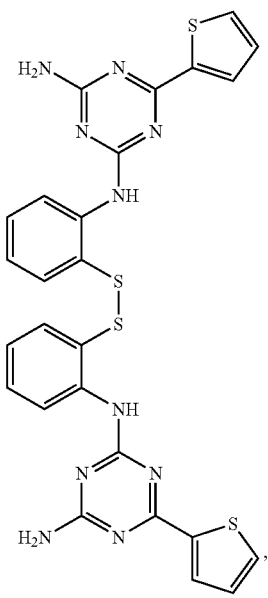
MTF 397
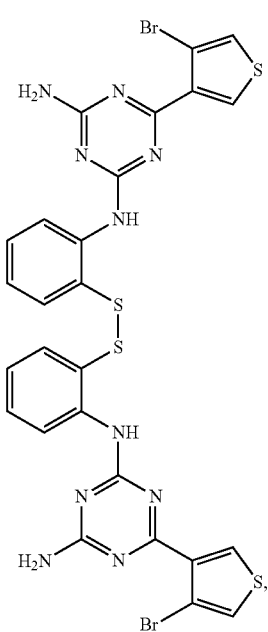
MTF 443
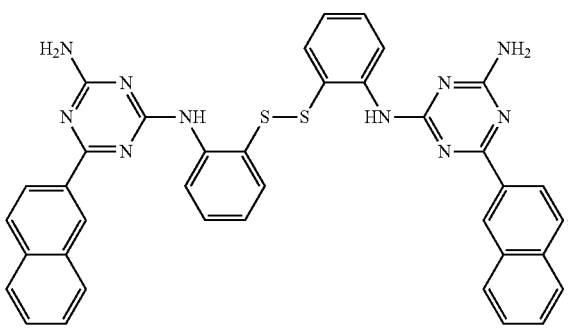
Molecular Weight: 688,8320
MTF 445
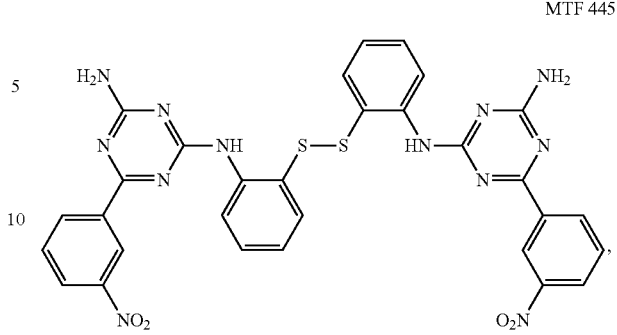
Molecular Weight: 678,7060
MTF 446
Molecular Weight: 768, 8680
MTF 449
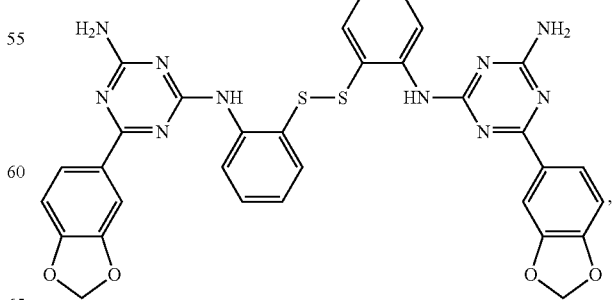
Molecular Weight: 676,7300

MTF 450
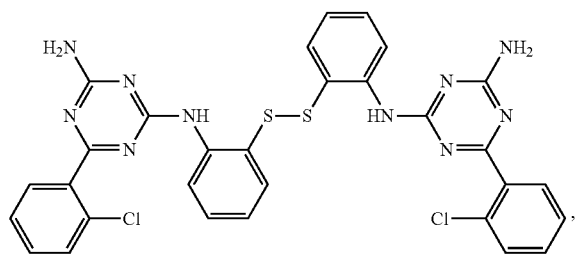
Molecular Weight: 657,5960
MTF 451
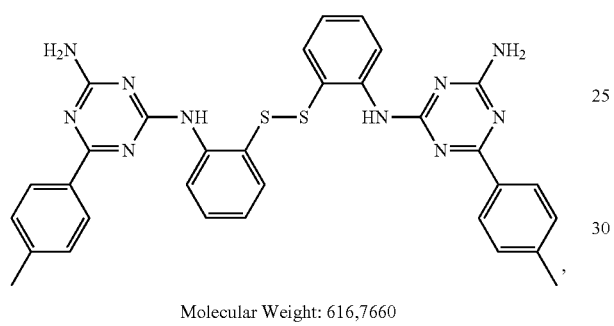
Molecular Weight: 616,7660
MTF 452
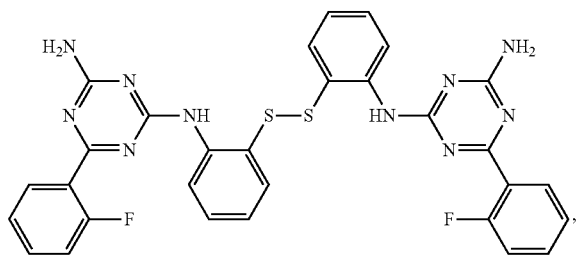
Molecular Weight: 624,6928
MTF 456
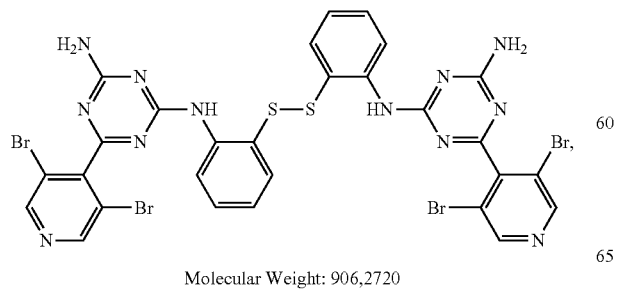
Molecular Weight: 906,2720
MTF 460
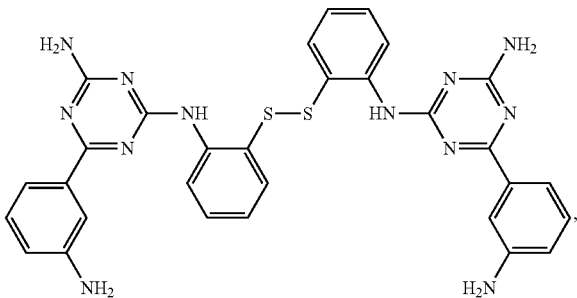
Molecular Weight: 618,7420
MTF 463
Molecular Weight: 678,7060
4. The compound of claim 1, wherein the compound is selected from
CRO 15
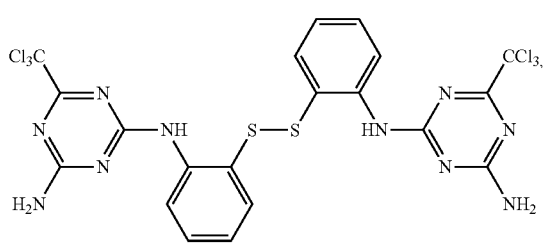

167
-continued
MTF 233
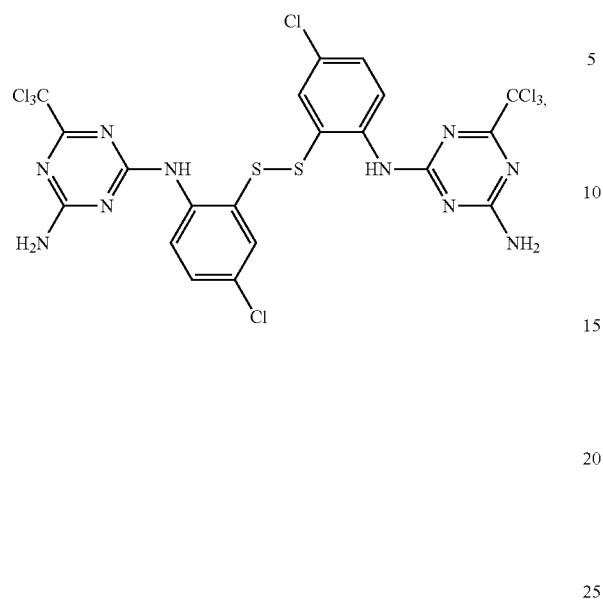
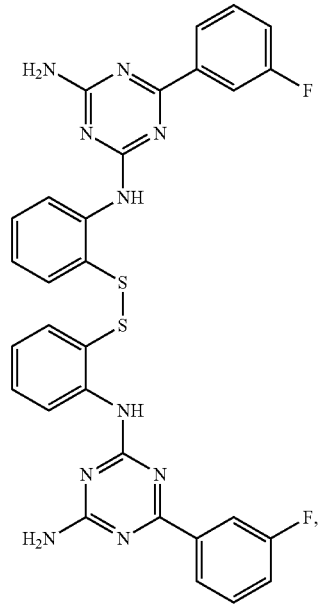
MTF 319
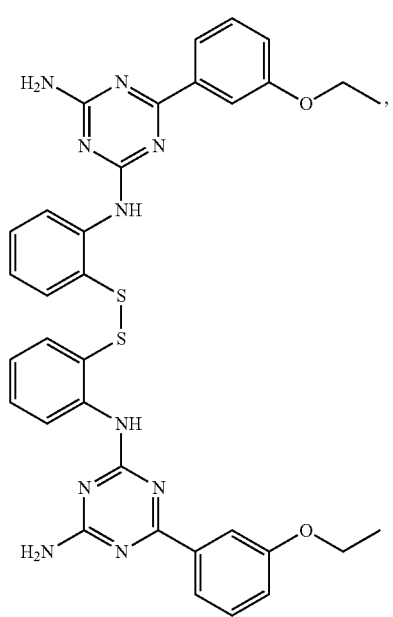
168
-continued
MTF 320
MTF 322
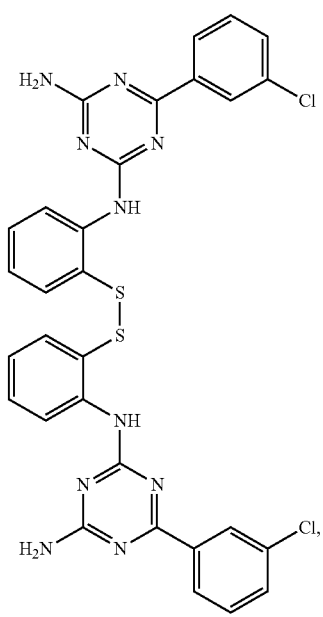

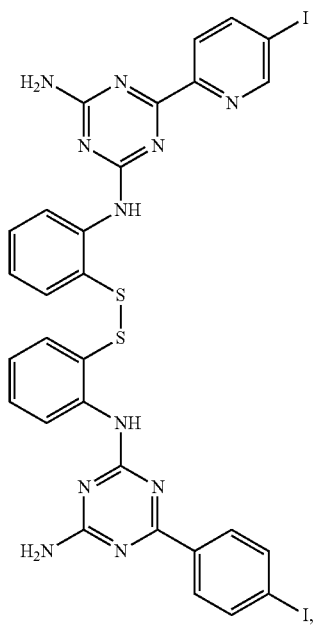
MTF 328
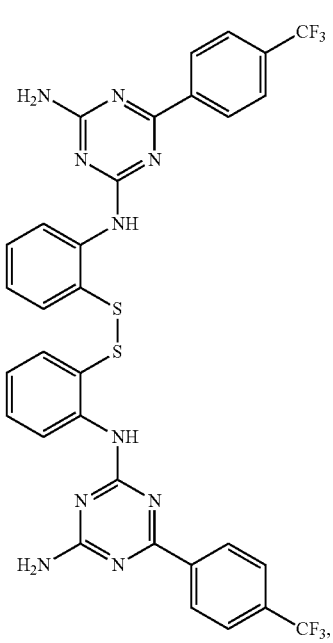
MTF 394
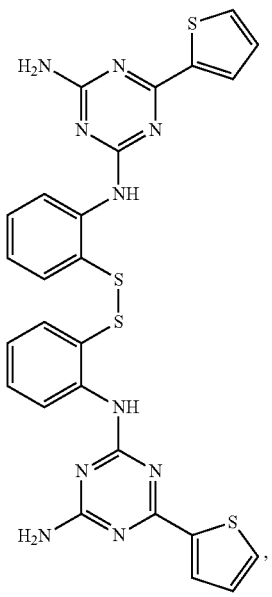
MTF 396
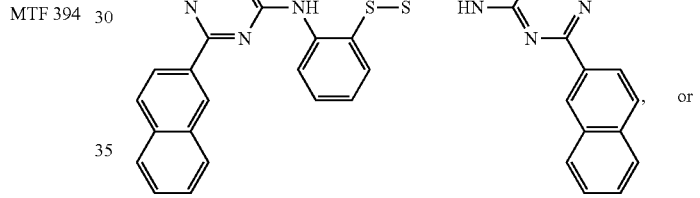
MTF 443
Molecular Weight: 688,8320
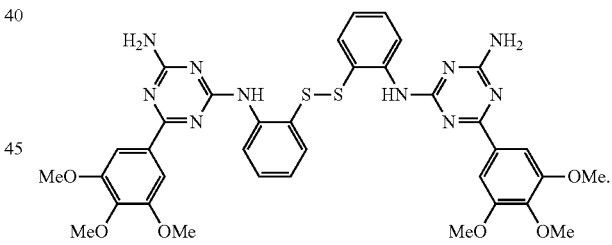
MTF 446
Molecular Weight: 768, 8680
5. A pharmaceutical composition comprising a compound of claim 1, and a pharmaceutically acceptable carrier.
* * * * *